United States Patent
Brown et al.

(10) Patent No.: US 9,790,498 B2
(45) Date of Patent: *Oct. 17, 2017

(54) PHASE CHANGING FORMULATIONS OF NUCLEIC ACID PAYLOADS

(71) Applicant: Dicerna Pharmaceuticals, Inc., Cambridge, MA (US)

(72) Inventors: Bob Dale Brown, Millington, NJ (US); Sujit Kumar Basu, Newton, MA (US)

(73) Assignee: DICERNA PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/957,073

(22) Filed: Dec. 2, 2015

(65) Prior Publication Data
US 2016/0083729 A1 Mar. 24, 2016

Related U.S. Application Data

(60) Division of application No. 14/105,956, filed on Dec. 13, 2013, now Pat. No. 9,217,146, which is a continuation of application No. PCT/US2012/042057, filed on Jun. 12, 2012.

(60) Provisional application No. 61/497,387, filed on Jun. 15, 2011.

(51) Int. Cl.
| | |
|---|---|
| *C12N 15/11* | (2006.01) |
| *C12N 15/113* | (2010.01) |
| *G01N 33/68* | (2006.01) |
| *A61K 31/713* | (2006.01) |
| *A61K 47/42* | (2017.01) |

(52) U.S. Cl.
CPC .......... *C12N 15/113* (2013.01); *A61K 31/713* (2013.01); *A61K 47/42* (2013.01); *C12N 15/111* (2013.01); *G01N 33/68* (2013.01); *C12N 2310/14* (2013.01); *C12N 2310/3513* (2013.01); *C12N 2320/30* (2013.01); *C12N 2320/32* (2013.01)

(58) Field of Classification Search
None
See application file for complete search history.

(56) References Cited

FOREIGN PATENT DOCUMENTS

| WO | WO 00/23113 A1 | 4/2000 | ............ A61K 47/48 |
|---|---|---|---|
| WO | WO 2004/020981 A2 | 3/2004 | |

OTHER PUBLICATIONS

Castanotto, et al., "The Promises and Pitfalls of RNA-Interference-Based Therapeutics," *Nature*, vol. 457, pp. 426-433, 2009.
Hällbrink, et al., "Prediction of Cell-Penetrating Peptides," *International Journal of Peptide Research and Therapeutics*, vol. 11, No. 4, pp. 249-259, Dec. 2005.
Lu, et al., "A Novel Mechanism Is Involved in Cationic Lipid-Mediated Functional siRNA Delivery," *Molecular Pharmaceutics*, vol. 6, No. 3, pp. 763-771, 2009.
Pujals, et al., "Mechanistic Aspects of CPP-Mediated Intracellular Drug Delivery: Relevance of CPp Self-Assembly," *Biochimica et Biophysica Acta*, vol. 1758, No. 3, pp. 264-279, Jan. 30, 2006.
Korean Patent Office Authorized Officer: Kim, Seung Beoin, International Search Report and Written Opinion; PCT/US2012/042057, 13 pages, dated Feb. 13, 2013.

*Primary Examiner* — Kate Poliakova-Georgantas
(74) *Attorney, Agent, or Firm* — MH2 Technology Law Group, LLP

(57) ABSTRACT

The present invention is based, at least in part, upon discovery of a process for identifying phase changing peptides. Such phase changing peptides are capable of enhancing in vitro and in vivo delivery of oligonucleotides (e.g., dsRNAs) in lipidic, vesicular, micellar and/or naked oligonucleotide formulations.

18 Claims, 4 Drawing Sheets

Figure 1. Process Flow Diagram for Design, Identification and Screen of Phase Changing dsRNA Formulations Figure 2. Schematic Representation of Different Formulations

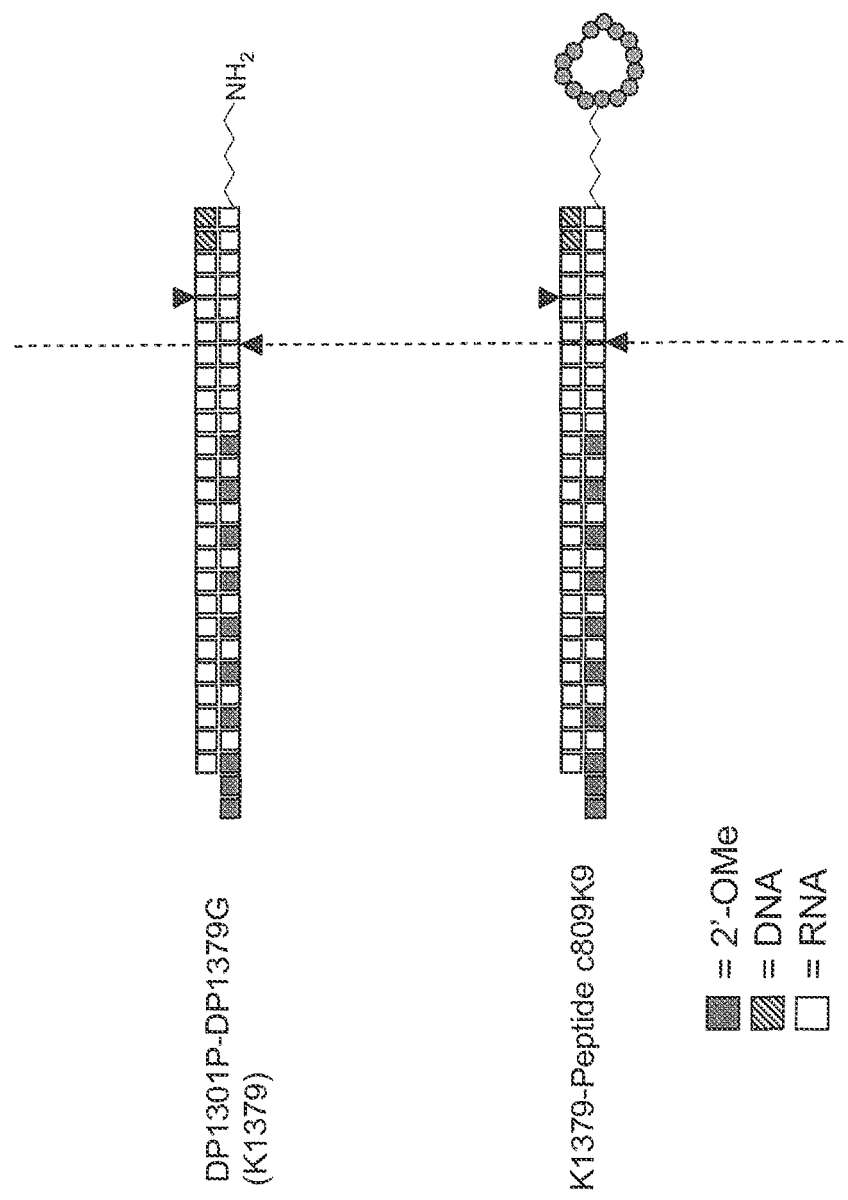

PHASE CHANGING FORMULATIONS OF NUCLEIC ACID PAYLOADS

CROSS-REFERENCE TO RELATED APPLICATION

This application is a divisional of U.S. application Ser. No. 14/105,956, filed Dec. 13, 2013 which is a Continuation application of PCT Application No. PCT/US2012/042057 filed Jun. 12, 2012, which claims priority to U.S. Provisional Application No. 61/497,387, filed Jun. 15, 2011, the entire contents of which are incorporated herein by reference.

SEQUENCE LISTING

The attached sequence listing, "3904_1044_seq_listing", 83 KB in size, was created on Dec. 2, 2015, and is hereby incorporated by reference.

FIELD OF THE INVENTION

The invention relates to the design of phase changing formulations containing nucleic acids, e.g., short RNA molecules, and their method of use.

BACKGROUND OF THE INVENTION

Oligonucleotides and short RNA molecules cannot easily cross cell membranes because of their size and their polyanionic nature resulting from the negative charge of the phosphate groups. Delivery has therefore been one of the major challenges for RNAi technology (Castanotto and Rossi, Nature 2009; 457: 426-433). To trigger RNAi following systemic administration, a formulation containing short RNA molecules not only requires (1) that the payload be protected from enzymatic and non-enzymatic degradation, and (2) that the appropriate serum half-life and biodistribution of the formulation be provided, but also requires (3) that cellular uptake or internalization of the formulation occurs and (4) and that once internalized, delivery to the cytoplasm of the cell is facilitated. Many formulations that excel in criteria (1) and (2) above show deficiency in criteria (3) and (4), i.e., many formulations show excellent biodistribution but no delivery of formulated agents. Since the oligonucleotides are either not internalized or, once internalized, not released to the cytoplasm, there is no knockdown of the target gene. Importantly, criteria (3) and (4) are equally critical for local delivery (e.g., tissue-specific delivery) as well. Moreover, Lu, Langer and Chen (Mol Pharm. 2009; 6(3):763-71) postulated that while endocytosis is the primary method of internalization for the nanoparticle formulations in the cell, most of the formulation and payload thus taken up by the cells do not reach cytoplasm and are therefore unable to trigger RNAi. That is, once the formulation is inside the cell, the oligonucleotides pass through the endocytic pathway, eventually being delivered to the lysosome, where the oligonucleotide undergoes lysosomal degradation.

The instant invention is directed to the discovery and design of phase changing charge-trapped peptides that are able to trigger structural changes in a formulation comprising the oligonucleotide and the phase changing charge-trapped peptide, where the structural changes increase release of the oligonucleotide (and, optionally, the peptide, if it is/remains conjugated to the oligonucleotide) to the cytoplasm. Though not being bound by theory, after endocytosis and entry into the endocytic pathway (e.g., the endosome and/or multi-vesicular bodies (MVBs)), the decreased pH of the compartments of the endocytic pathway induces protonation of the phase changing charge-trapped peptide, resulting in the release of the associated oligonucleotide, not only from whatever vesicle or micelle within which the oligonucleotide and associated peptide may optionally have been delivered, but also from the endocytic pathway compartment (e.g., endosome), thereby resulting in localization to the cytoplasm, where the oligonucleotide can be active as, e.g., an RNAi agent, as opposed to transiting to and being degraded within the lysosome.

BRIEF SUMMARY OF THE INVENTION

Disclosed herein is the discovery of a process for designing, identifying and screening phase changing charge-trapped peptides having the property of increasing cellular uptake and cytoplasmic delivery of oligonucleotides, such as dsRNA. The process involves designing candidate phase changing charge-trapped peptides, including designing amino acid consensus sequences with phase changing charge-trapped residues, providing a library of such peptides and screening the peptides for their efficacy in knocking down (i.e. inhibiting and/or reducing) the cellular expression of a target gene after being administered as a component in a formulation containing short oligonucleotides, such as double stranded RNA (dsRNA) molecules. The process includes one or more combinations of specific method steps: (a) designing a library of charge-trapped peptides, (b) synthesis of the peptides, (c) conjugation of charge-trapped peptides to fluorescent dye and/or dsRNAs, (d) formulation of dsRNA and peptide and/or dsRNA-peptide conjugates (formulation of dsRNA alone in the same formulation matrix is used as a control), (e) comparative measurements of cell internalization, (f) comparative measurement of induced formulation leakiness, (g) comparative measurement of target gene knockdown, and (h) comparative evaluation of efficacy of formulations (e.g., anti-tumor efficacy in animal tumor models). The design parameters and the screening process optimize phase change inducible disruption of the oligonucleotide/peptide, oligonucleotide/lipidic, oligonucleotide/polymer, peptide/peptide, peptide/lipidic, or peptide/polymer components of an oligonucleotide formulation, and thus achieve all the attributes of a formulation containing short RNA molecule specified above. Therefore, the resultant formulations provide protection of the payload from (1) degradation and (2) elimination, resulting in appropriate half-life and biodistribution of the formulation in the state in which they are administered, as well as, allow improved (3) cellular uptake/internalization and improved (4) delivery to the cytoplasm of the cell, which, in certain embodiments, particularly constitute the improvements mediated by the phase changing charge-trapped peptides of the formulation. There are several ways to induce phase change or change of structure to improve cell-formulation interaction and cellular delivery using phase changing charge-trapped peptides and/or peptide-oligonucleotide derivatives: pH change induced protonation/deprotonation, disulphide reduction, hydrolysis and enzymatic processing, e.g., proteolysis.

The invention therefore contemplates a method of identifying a phase changing peptide based on a peptide's efficacy in delivering an oligonucleotide to the cytoplasm of a cell in a subject after administration of a formulation comprising the oligonucleotide and the peptide, comprising the steps of:

(i) providing a test peptide, wherein the peptide is a charge-trapped peptide;

(ii) preparing a formulation comprising the oligonucleotide and the test peptide;

(iii) comparing the activity of the formulation with the activity of a control formulation which lacks the test peptide, in one or more of the following assays:

(a) an assay measuring/evaluating internalization of the oligonucleotide into the cell, (b) an assay measuring/evaluating leakiness of the cell induced by the formulation of step (ii), (c) an assay measuring/evaluating in vitro target knockdown, (d) an assay measuring/evaluating in vivo target knockdown, (e) an assay measuring/evaluating in vivo efficacy; and (iv) identifying the test peptide as a phase changing peptide if the formulation of step (ii) displays an increased activity in at least one of the assays (a)-(e) relative to the control formulation.

Preferably, the oligonucleotide is selected from the group consisting of a siRNA and a DsiRNA; the DsiRNA is a DsiRNA of 25-30 nucleotides; the DsiRNA is an extended DsiRNA.

Preferably, the formulation is selected from the group consisting of a lipid formulation and a polymer formulation; the formulation is selected from the group consisting of a vesicle based formulation and a micelle based formulation; the formulation comprises free oligonucleotide in solution.

Preferably, the peptide is selected from the group of peptides with an amino acid sequence consisting of SEQ ID NOs:1-47; the peptide is selected from the group of peptides with an amino acid sequence consisting of SEQ ID NOs: 48-105.

Preferably, the peptide is cyclized via a structure selected from the group consisting of a Citrulline-Valine (Cit-Val) structure, a Valine-Citrulline (Val-Cit) structure, and a repeat thereof.

Preferably, the peptide optionally further comprises a linker comprising one or more amino acids; the linker comprises a cysteine residue; the linker comprises a structure selected from the group consisting of a Citruline-Valine (Cit-Val) structure, a Valine-Citruline (Val-Cit) structure, and a repeat thereof; the linker is attached to the oligonucleotide Preferably, the peptide optionally further comprises spacer amino acids; the spacer amino acids comprise Glycine and/or Serine.

Preferably, the formulation optionally further comprises PEG; and the peptide is attached to PEG.

Preferably, the increased activity of the formulation comprising the oligonucleotide and the test peptide of step (iii) relative to the control formulation is an increase of at least 10%; the increased activity of the formulation comprising the oligonucleotide and the test peptide of step (iii) relative to the control formulation is an increase of at least 25%; the increased activity of the formulation comprising the oligonucleotide and the test peptide of step (iii) relative to the control formulation is an increase ranging from about 25% up to and including about 100%; the increased activity of the formulation comprising the oligonucleotide and the test peptide of step (iii) relative to the control formulation is an increase ranging from about 100% up to and including about 1000%; the increased activity of the formulation comprising the oligonucleotide and the test peptide of step (iii) relative to the control formulation is an increase of at least 1000%.

Preferably, the peptide is conjugated to the oligonucleotide; the oligonucleotide is a DsiRNA.

Preferably, the conjugated peptide is in the aqueous phase of the formulation; the conjugated peptide is in the lipid or polymer phase of the formulation; the oligonucleotide and the peptide are in the aqueous phase of the formulation.

Preferably, the oligonucleotide is released from a compartment of an intracellular vesicle-mediated delivery pathway selected from the group consisting of an endocytic delivery pathway compartment, an exocytic delivery pathway compartment and a lysosomal delivery pathways compartment via a structural or biochemical change in the phase-changing peptide; the structural or biochemical change in the phase-changing peptide comprises release of a cyclising linkage within the phase-changing peptide; the oligonucleotide is released from an endocytic pathway compartment selected from the group consisting of a clathrin-coated vesicle (CCV), caveolae, a macropinocytic or phagocytic cell membrane invagination, a phagosome, an early endosome, a multivesicular body (MVB), an endosomal carrier vesicle (ECV), a late endosome and a lysosome via a structural or biochemical change in the phase-changing peptide.

Preferably, linearization of the charge-trapped peptide produces an effect selected from the group consisting of (a) a change in the pI value of the peptide as compared to the cyclic form; (b) a change in the pKa value of the peptide as compared to the cyclic form; (c) a change in the pKa value of a formulation comprising the peptide as compared to the same formulation comprising the cyclic form of the peptide; (d) a change in the in vivo tolerability of the peptide as compared to the cyclic form; (e) a change in the in vivo tolerability of a formulation comprising the linearized form of the charge-trapped peptide as compared to the formulation comprising the cyclic form of the peptide; (f) altered levels of tumor cell growth inhibition in an in vitro cell growth assay as compared to the formulation comprising the cyclic form of the peptide; and (g) in a formulation, decreased cell viability in vitro in a cell viability assay than administration of a corresponding formulation possessing the cyclic form of the peptide; a change in the pI of the peptide or the formulation of 0.2 or greater is observed between cyclic and linearized peptide forms; a change in the pKa of the peptide or the formulation of 0.2 or greater is observed between cyclic and linearized peptide forms; the change in pKa occurs within the pH 5.0 to pH 7.0 range, optionally within the pH 5.5 to pH 6.5 range.

Preferably, the formulation is a lipid nanoparticle.

Preferably, tolerability is assessed by a method selected from the group consisting of: detection of increased target tissue toxicity in the linearized state versus little or no target tissue toxicity in the cyclic state; detection of increased body weight loss when administered in the linearized state versus the cyclic state; detection of increased liver and/or spleen weight when administered in the linearized state versus the cyclic state; detection of altered appearance of a target tissue when administered in the linearized state versus the cyclic state; detection of greater mortality and/or morbidity when administered in the linearized state versus the cyclic state; and any combination thereof.

Preferably, administration to a subject of a formulation comprising the charge-trapped peptide produces reduced tumor cell growth with increased tolerability and/or lower toxicity than administration of a corresponding formulation possessing a linear forms of the peptide.

The invention also relates to a method for reducing expression of a target gene in a cell of a subject, comprising:
contacting the cell with a formulation comprising dsRNA and the phase changing peptide recited in claims 8-18, in an amount effective to reduce expression of the target gene in the cell in comparison to a reference dsRNA.

The invention also relates to a method of disrupting a formulation or particle comprising:

preparing a formulation or particle comprising a cyclic charge-trapped peptide that is capable of linearizing when introduced into a reducing or low pH environment;

introducing the formulation or particle to a sufficiently reductive or low pH environment to linearize the cyclic peptide, wherein the linearization of the cyclic peptide disrupts the formulation or particle, thereby disrupting the formulation or particle.

Preferably, linearization of the cyclic peptide produces sufficient mechanical force to disrupt the formulation or particle; the formulation or particle is a lipid formulation; formulation or particle is selected from the group consisting of a vesicle based formulation and a micelle based formulation; linearization of the cyclic peptide exposes a membrane integration domain within the peptide; linearization of the cyclic peptide exposes a pore-forming peptide.

Preferably, the formulation or particle further comprises a dsRNA; the dsRNA is conjugated to the cyclic peptide; the formulation or particle further comprises a DsiRNA; the DsiRNA is conjugated to the cyclic peptide; the dsRNA is a dsRNA of 19-25 nucleotides; the DsiRNA is a dsiRNA of 25-30 nucleotides.

Preferably, the conjugated cyclic peptide is in the aqueous phase of the formulation; the conjugated cyclic peptide is in the lipid or polymer phase of the formulation; the dsiRNA and the conjugated cyclic peptide are in the aqueous phase of the formulation; the cyclic peptide comprises a linkage selected from the group consisting of a disulfide linkage and a Citrulline-Valine linkage, wherein disruption of the linkage cyclizes the peptide; the cyclic peptide comprises an amino acid sequence selected from the group consisting of SEQ ID NOs:1-105.

Preferably, reducing or low pH environment constitutes an endocytic pathway compartment; the endocytic pathway compartment is selected from the group consisting of a clathrin-coated vesicle (CCV), caveolae, a macropinocytic or phagocytic cell membrane invagination, a phagosome, an early endosome, a multivesicular body (MVB), an endosomal carrier vesicle (ECV), a late endosome and a lysosome.

Preferably, the formulation optionally further comprises PEG; the cyclic peptide is attached to PEG.

BRIEF DESCRIPTION OF THE DRAWINGS

FIG. 4 schematically depicts an exemplary DsiRNA-charge-trapped peptide conjugate of the invention. Arrowheads in schematics indicate projected dicer enzyme cleavage sites within the DsiRNA and DsiRNA-peptide conjugates. Shaded residues indicate 2'-O-methyl modified residues, while deoxyribonucleotide residues are indicated by cross-hatched residues.

DETAILED DESCRIPTION OF THE INVENTION

Figure 1:
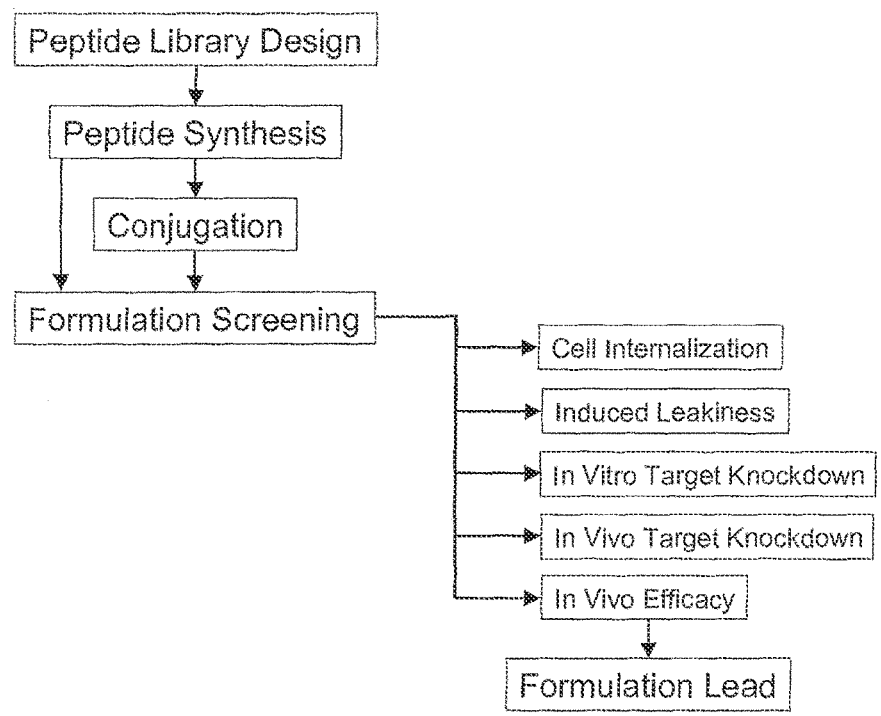
FIG. 1 is a Process Flow Diagram for Design, Identification and Screening of Phase changing charge-trapped dsRNA Formulations FIG. 2. Schematic Representation of Different Formulations
Figure 2:
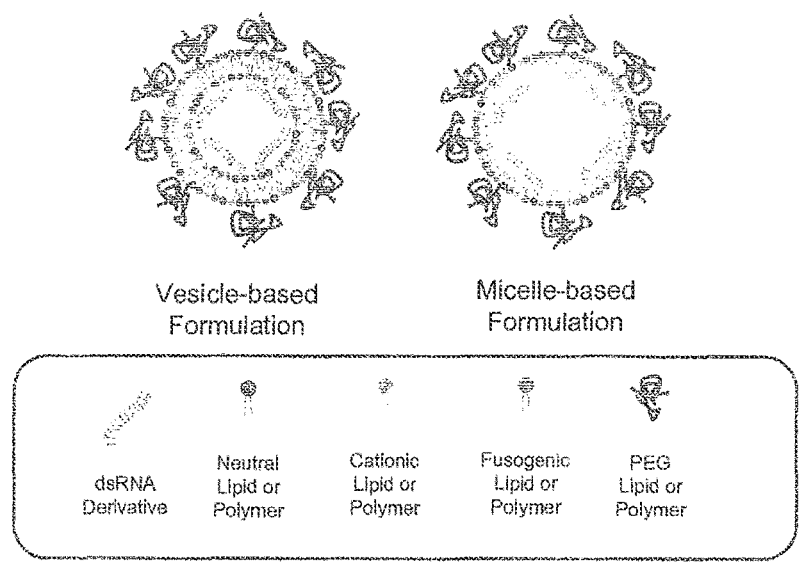

The present invention is directed to methods of identifying a phase changing charge-trapped peptide based on a peptide's efficacy in delivering an oligonucleotide to the cytoplasm of a cell in a subject after administration of a formulation comprising the oligonucleotide and the peptide. Formulations comprising a phase changing charge-trapped peptide are capable of enhancing both the entry of an oligonucleotide into a cell and its subsequent release into the cytoplasm as compared to formulations lacking the phase changing charge-trapped peptide as described herein.

The formulations optionally further comprise a lipid or polymer structure which aids in protecting the oligonucleotide from enzymatic and non-enzymatic degradation, and increasing the serum half-life of the oligonucleotide after systemic administration.

The present invention is also directed to methods of preparing the phase changing charge-trapped peptide as well as to methods of preparing the formulations comprising the peptides and oligonucleotides, and is further directed to the formulations themselves. In one instance, the oligonucleotides of these formulations are DsiRNAs that are capable of reducing the level and/or expression of genes in vivo or in vitro.

The invention provides for novel phase changing charge-trapped peptide:oligonucleotide conjugates, including phase changing charge-trapped peptide:DsiRNA conjugates for example.

The invention provides the following advantages. The invention provides for phase changing charge-trapped peptides that enhance delivery of an oligonucleotide, such as a DsiRNA, of the invention.

The charge-trapped peptides of the invention are also advantageous over the peptides known in the art because the charge-trapped peptides described herein do not need to be linked to the dsRNA via a cleavable linker but can be conjugated to a dsRNA via a stable linker, since dicer enzyme will process the dsRNA-peptides of the invention to produce the siRNA molecule suitable for processing in the RISC pathway. This is especially advantageous for pharmaceutical compositions due to improved stability of stable linkers (cleavable linkers may cleave during manufacturing and/or shelf storage thereby losing their functionality).

Definitions

The invention provides methods for identifying and using a phase changing charge-trapped peptide composition based on the charge-trapped peptides in delivering an oligonucleotide to the cytoplasm of a cell in a subject after administration of a formulation comprising the oligonucleotide and the charge-trapped peptide. The invention further provides formulations comprising the identified phase changing charge-trapped peptide(s) and an oligonucleotide, where the formulations optionally further comprise lipidic or polymeric components. The invention also provides for methods of making and using these formulations including methods for reducing expression of a target gene in a cell, involving contacting a cell which preferably comprises the target gene, with a formulation comprising a phase changing charge-trapped peptide and an isolated dsRNA in an amount effective to reduce expression of a target gene in a cell.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, a "phase changing residue" is an amino acid residue of a peptide that undergoes a structural or biochemical change upon exposure to conditions of altered pH (i.e., protonation or deprotonation state of the residue), altered redox state (oxidation or reduction state), or altered chemical (e.g., hydrolysis) or biochemical (e.g., enzymatic) cleavage or activation. In certain embodiments, a "phase changing residue" is an amino acid residue that undergoes a structural or biochemical change upon exposure to such a condition that occurs within an intracellular vesicle-mediated delivery pathway (e.g., endocytic, exocytic or lysosomal delivery pathways). In related embodiments, a "phase changing residue" is an amino acid residue that undergoes a structural or conformational change upon exposure to such a condition that occurs within a mammalian cellular endocytic pathway compartment. While it is appreciated that whether an amino is a phase changing residue will ultimately be influenced by the context within which such residue exists, exemplary amino acids for which there is a likelihood of being phase changing residues include the following: D, E, H, K, R and P.

The term "peptide" embraces a limited number of contiguous amino acids that are peptide bonded together, whether the peptide is a naturally occurring molecule or synthetic. (i.e. a naturally occurring molecule, or a chemically/physically modified variant thereof). A "peptide" as used herein can originate from a naturally occurring protein.

As used herein the term peptide means a linear peptide, a branched peptide or a cyclic peptide of at least 6 amino acids, or has 6-100 amino acids, for example, 6, 7, 8, 9, 10, 15, 20, 25, 30, 35, 40, 45, 50, 55, 60, 65, 70, 75, 80, 85, 90, 95 or 100, or has 10-50 amino acids (for example, 10, 15, 20, 25, 30, 35, 40, 45 or 50 amino acids) or has 15-30 amino acids (for example, 15, 16, 17, 18, 19, 20, 21, 22, 23, 24, 25, 26, 27, 28, 29 or 30 amino acids).

A "peptide" as used herein can be a synthetic peptide that is designed based on a structure-function relationship for a particular amino acid sequence and does not necessarily have homology to a natural sequence. A "peptide" as used herein can comprise different protein domains (for example a chimeric peptide).

A peptide that has no net charge means a "neutral peptide."

As used herein, a "neutral peptide" has a net charge that is approximately zero at neutral pH (for example pH 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4 or 8.5).

A "neutral peptide" also includes a peptide that has a net charge that is approximately zero at neutral pH and/or has an isoelectric point (pI) of about pH 7 (for example pH 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4 or 8.5).

Positively charged amino acids are Lysine (Lys, K), Arginine (Arg, R) and Histidine (His, H). Negatively charged amino acids are Aspartic acid or aspartate (Asp, D), Glutamic acid or glutamate (Glu, E). (Reference: Lehninger Principles of Biochemistry, $3^{rd}$ Ed., 2000. Edited by David L. Nelson and Michael M. Cox, Worth Publishers, New York, N.Y.)

As used herein, a "phase changing peptide" is a peptide which comprises sufficient phase changing residues to enable the peptide to efficiently effect uptake/internalization by a target cell and entry into the cytoplasm of an oligonucleotide which is associated or conjugated to the phase changing peptide, or composition thereof. In certain embodiments, the "phase changing peptide" undergoes a structural or biochemical change in response to reduction, protonation or cleavage (enzymatic or hydrolytic).

As used herein, a "charge-trapped peptide" is a cyclic peptide of at least seven amino acids residues in length comprising charged amino acid residues (i.e., D, E, H, K, R) at 15% or more residues of the peptide. In certain embodiments, the length of a "charge trapped peptide" of the invention is between about 10 and about 100 amino acid residues in length, optionally between about 12 and about 80 amino acid residues in length, and optionally between about 13 and about 40 amino acid residues in length. In some embodiments, a "charge-trapped peptide" of the invention comprises charged amino acid residues that are each of positive (i.e., H, K, R) or negative (i.e., D, E) charge. In other embodiments, a combination of charges is contained within a "charge-trapped peptide" of the invention. In certain embodiments, a "charge-trapped peptide" of the invention comprises charged amino acid residues at 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or all residues of the peptide (excluding, e.g., cysteine residues and/or citrulline-valine residues used to cyclise such peptides). In some embodiments, a "charge-trapped peptide" of the invention possesses three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, 21 or more, 22 or more, 23 or more, 24 or more, 25 or more, 30 or more, 35 or more, 40 or more, 45 or more or even 50 or more charged residues, optionally having such total number of positively charged residues, or of negatively charged residues. In many embodiments, a "charge trapped peptide" of the invention carries a net positive charge of +3 or greater, e.g., +3 or greater, +4 or greater, +5 or greater, +6 or greater, +7 or greater, +8 or greater, +9 or greater, +10 or greater, +11 or greater, +12 or greater, +13 or greater, +14 or greater, +15 or greater, +16 or greater, +17 or greater, +18 or greater, +19 or greater, +20 or greater, +21 or greater, +22 or greater, +23 or greater, +24 or greater or even +25 or greater. In such embodiments, exemplary ratios of positively charged residues to negatively charged residues include infinity, 50:1, 25:1, 10:1, 5:1, 4:1, 3:1, 2:1, and 3:2. In some embodiments, a "charge trapped peptide" may alternatively carry a net negative or even a net neutral charge. In such embodiments, exemplary ratios of negatively charged residues to positively charged residues include infinity, 50:1, 25:1, 10:1, 5:1, 4:1, 3:1, 2:1, 3:2 and 1:1.

Without wishing to be bound by theory, a "charge-trapped peptide" of the invention characteristically exhibits one or more of the following attributes:

(a) linearization of the "charge-trapped peptide" produces a change in pI value of the peptide between cyclic and processed linear forms (e.g., a change in pI of 0.2 or greater is observed between cyclic and processed linear peptide forms);

(b) linearization of the "charge-trapped peptide" produces a change in pKa value of the peptide between cyclic and processed linear forms (e.g., a change in pKa of 0.2 or greater is observed between cyclic and processed linear peptide forms; in certain embodiments, such changes occur within the pH 4.5 to pH 7.2 range, within the pH 5.0. to pH 6.9 range, or optionally within the pH 5.5 to pH 6.5 range);

(c) linearization of the "charge-trapped peptide" produces a change in pKa value of the formulation comprising the "charge-trapped peptide" between formulations (e.g., lipid nanoparticles) comprising cyclic and processed linear forms of the charge-trapped peptide(s) (e.g., a change in pKa of 0.2 or greater is observed between formulations comprising cyclic and processed linear peptide forms; in certain embodiments, such changes occur within the pH 4.5 to pH 7.2 range, within the pH 5.0. to pH 6.9 range, or optionally within the pH 5.5 to pH 6.5 range);

(d) linearization of the "charge-trapped peptide" produces a change in in vivo tolerability of the peptide as compared to the cyclic form (as assessed by, e.g., detection of increased target tissue toxicity in the linearized state versus little or no target tissue toxicity in the cyclic state; detection of increased body weight loss when administered in the linearized state versus the cyclic state; detection of increased liver and/or spleen weight when administered in the linearized state versus the cyclic state; detection of altered appearance of target tissues when administered in the linearized state versus the cyclic state; detection of greater mortality and/or morbidity when administered in the linearized state versus the cyclic state; etc., including any combination of the preceding);

(e) linearization of the "charge-trapped peptide" within a formulation (e.g., a lipid nanoparticle) produces a change in in vivo tolerability of the formulation as compared to the formulation comprising the cyclic form of the peptide (with formulation tolerability assessed by, e.g., detection of increased target tissue toxicity in the linearized state versus little or no target tissue toxicity in the cyclic state; detection of increased body weight loss when administered in the linearized state versus the cyclic state; detection of increased liver and/or spleen weight when administered in the linearized state versus the cyclic state; detection of altered appearance of target tissues when administered in the linearized state versus the cyclic state; detection of greater mortality and/or morbidity when administered in the linearized state versus the cyclic state; etc., including any combination of the preceding);

(f) linearization of the "charge-trapped peptide" within a formulation (e.g., a lipid nanoparticle) produces altered levels of tumor cell growth inhibition in an in vitro cell growth assay as compared to the formulation comprising the cyclic form of the peptide;

(g) in vitro administration of a formulation (e.g., a lipid nanoparticle) comprising a cyclic "charge-trapped peptide" produces increased cell viability in a cell viability assay than administration of a corresponding formulation possessing linear form(s) of the "charge-trapped peptide(s)";

(h) in vivo administration of a formulation (e.g., a lipid nanoparticle) comprising a "charge-trapped peptide" produces reduced tumor cell growth with increased tolerability and/or lower toxicity than administration of a corresponding formulation possessing linear forms of the "charge-trapped peptide(s)".

A "target cell" means any cell as defined herein, for example a cell derived from or present in any organ including but not limited to the brain, the adrenal or other sites outside the brain (e.g., an extracranial site) such as for example, the kidney, the liver, the pancreas, the heart, the spleen, the gastrointestinal (GI) tract (e.g., stomach, intestine, colon), the eyes, the lungs, skin, adipose, muscle, lymph nodes, bone marrow, the urinary and reproductive systems (ovary, breasts, testis, prostrate), placenta, blood cells and a combination thereof.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell. Within certain embodiments, the term "cell" refers specifically to mammalian cells, such as human cells, that contain one or more isolated oligonucleotides, such as a dsRNA. In particular embodiments, a cell processes dsRNAs or dsRNA-containing molecules resulting in RNA interference of target nucleic acids, and contains proteins and protein complexes required for RNAi, e.g., Dicer and RISC.

As used herein the term "formulation" is synonymous with composition. In one embodiment, a formulation comprising an oligonucleotide and a phase changing charge-trapped peptide further comprises additional components, e.g. a lipid vesicle or micelle, which provide the oligonucleotide and phase changing charge-trapped peptide increased pharmakinetics in terms of half life for example when systemically administered. Non limiting examples of additional components include a lipid formulation or a polymer formulation. In another embodiment, the formulation is a vesicle based formulation or a micelle based formulation. In another embodiment, the formulation comprises free oligonucleotide in solution.

Polymeric nanocapsules or microcapsules facilitate transport and release of the encapsulated or bound dsRNA into the cell. They include the self-assembly micelle-like nanoparticles based on phosphlipid-polyethyleneimine conjugates as described by Ko et al. (2009) Journal of Controlled Release 133:132-138). They also include vesicle based formulations such as the stable nucleic acid lipid particles (SNALP) comprising synthetic cholesterol, 1,2,-distearoyl-sn-glycero-3-phosphocholine, PEG-cDMA and 1,2-dilinoleyloxy-3-(N,N-dimethyl)aminopropane (DLinDMA) as described by Zimmerman et al. ((2006) Nature 441:111-114) and the liposomal siRNA delivery vehicle LNP201 as described by Abrams et al. ((2009) The American Society of Gene & Cell Therapy). They also include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

As used herein the term "associated" in reference to the phase changing charge-trapped peptide and the oligonucleotide means that the phase changing charge-trapped peptide and the oligonucleotide are present together in a formulation, such as a formulation comprising a lipid vesicle or micelle, though the phase changing charge-trapped peptide and the oligonucleotide are not necessarily conjugated to each other.

The methods of screening for a phase changing charge-trapped peptide include screening peptides individually or from a library of peptides, such as a phage display library, (see, e.g., Smith, 1985, Science 228: 1315; Scott & Smith, 1990, Science 249: 386; McCafferty et al., 1990, Nature 348: 552), where the peptides in a library each follow the formula of a defined consensus sequence or variants thereof. As used herein, the term "variant" when applied to a phase changing charge-trapped peptide or a phase changing charge-trapped peptide candidate is produced by mutagenizing a peptide with a consensus sequence by substituting or inserting one or more of the amino acid residues histidine, aspartic acid and glutamic acid. The amino acid residues may be substituted and/or inserted at the terminal end(s) of the peptide or internal to the phase changing charge-trapped peptide or the phase changing charge-trapped peptide candidate.

In libraries or repertoires as described herein, the preferred vectors are expression vectors that enable the expression of a nucleotide sequence corresponding to a polypeptide library member. Thus, selection is performed by separate propagation and expression of a single clone expressing the polypeptide library member or by use of any selection display system. As described above, a preferred selection display system uses bacteriophage display. Thus, phage or phagemid vectors can be used. Preferred vectors are phagemid vectors, which have an *E. coli* origin of replication (for double stranded replication) and also a phage origin of replication (for production of single-stranded DNA). The manipulation and expression of such vectors is well known in the art Briefly, the vector contains a β-lactamase or other selectable marker gene to confer selectivity on the phagemid, and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tags (for detection), optionally, one or more TAG stop codons and the phage protein pIII. In one embodiment, the vector encodes, rather than the pelB leader sequence, a eukaryotic GAS1 leader sequence which serves to direct the secretion of the fusion polypeptide to the periplasmic space in *E. coli* or to the medium in eukaryotic cell systems. Using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only, or produce phage, some of which contain at least one copy of the polypeptide-pIII fusion on their surface.

As used herein, a "mammalian cellular endocytic pathway compartment" refers to any component of the mammalian cellular endocytic pathway involved in transit between the cell membrane and the lysosome. Such compartments include, but are not necessarily limited to, clathrin-coated vesicles (CCVs), caveolae, macropinocytic or phagocytic cell membrane invaginations, phagosomes, early endosomes, multivesicular bodies (MVB), endosomal carrier vesicles (ECVs), late endosomes and lysosomes.

The term "efficacy" when used in the phrase "peptide's efficacy in delivering an oligonucleotide to the cytoplasm of a cell" is a relative term with respect the amount of oligonucleotide delivered to the cytoplasm under identical conditions but in the absence of the phase changing charge-trapped peptide.

As used herein, the term "oligonucleotide" includes any short single stranded or double stranded nucleic acid polymer. The oligonucleotide can be a siRNA, dsRNA, a DsiRNA or an antisense oligonucleotide. In certain embodiments, the DsiRNA can contain 25-30 nucleotides. In another embodiment the oligonucleotide is an extended DsiRNA, which can contain, e.g., 30-49 nucleotides or even 30-70 nucleotides or more. A DsiRNA can be cleaved by Dicer enzyme and can inhibit expression of a target RNA.

As used herein, the term "siRNA" refers to a double stranded nucleic acid in which each strand comprises RNA, RNA analog(s) or RNA and DNA. The siRNA comprises between 19 and 23 nucleotides or comprises 21 nucleotides. The siRNA typically has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the target gene/RNA. By "target nucleic acid" is meant a nucleic acid sequence whose expression, level or activity is to be modulated. The target nucleic acid can be DNA or RNA By "subject" is meant an organism, which is a donor or recipient of explanted cells or the cells themselves. "Subject" also refers to an organism to which the DsiRNA agents of the invention can be administered. A subject can be a mammal or mammalian cells, including a human or human cells.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA compositions may be micellar structures, such as a liposomes, capsids, capsoids, polymeric nanocapsules, or polymeric microcapsules.

Administration of the formulation comprising a phase changing oligonucleotide and an oligonucleotide can be administered in a suitably formulated pharmaceutical compositions by means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

As used herein the term "test peptide" refers to a peptide that is being assessed for its ability to meet the criteria of a phase changing peptide.

As used herein the phrase "measuring/evaluating internalization of the oligonucleotide" means assessing the rate or amount of oligonucleotide internalization (e.g. by direct penetration or by an endocytic pathway that requires endosome formation and is also referred to as receptor-mediated endocytosis.)

As used herein, the phrase "measuring/evaluating leakiness of the cell" has its art-recognized meaning as described, for example, by van Rossenberg et al., *J Biol Chem*. 2002; 277(48):45803-10.

As used herein, the phrase "measuring/evaluating in vitro target knockdown" means assessing the amount of decreased expression of a target gene in a cell that is mediated by an oligonucleotide such as a dsRNA in vitro.

As used herein, the phrase "measuring/evaluating in vivo target knockdown" means assessing the amount of decreased expression of a target gene in a cell that is mediated by an oligonucleotide such as a dsRNA, after systemically or tissue-specifically administering a composition comprising the oligonucleotide to an animal.

As used herein, the phrase "measuring/evaluating in vivo efficacy" refers to assessing the effect on a biological process such as tumor growth that is mediated by an oligonucleotide such as a dsRNA, after systemically or tissue-specifically administering a composition comprising the oligonucleotide to an animal.

As used herein, the phrase "increased activity in at least one of the assays (a)-(e) described above relative to the control formulation" means that the achieved improvement of functionalization of the phase changing charge-trapped peptide:oligonucleotide formulation compared to the oligonucleotide formulation alone is at least about 10%. In certain embodiments, the increase can range from about 10% up to about 25%. In additional embodiments, the increase can range from about 25% up to and including about 100%, up to and including 1000% and, in certain embodiments, can also be at least 1000%. In other words, the increase can be from about 1.1-fold to 1.5-fold, 1.5-fold to 2-fold, 2-fold up to 5-fold, up to about 10-fold, up to about 100-fold, up to about 1,000-fold, or more. In certain embodiments, these increases apply to formulations containing a dsRNA and non-covalently conjugated peptide, compared to a dsRNA formulation alone.

As used herein, "increases" also includes the concept that a phase changing charge-trapped peptide-oligonucleotide formulation requires less oligonucleotide (a lower dose of oligonucleotide) as compared to the amount or dose of an identical oligonucleotide formulation lacking the phase changing charge-trapped peptide to achieve an equivalent level of activity in the above assays, such as internalization, as determined by the $IC_{50s}$ in the assays described herein below. For example, the $IC_{50}$ for a dsRNA-phase changing charge-trapped peptide formulation that is required to achieve a 50% reduction in RNA/gene expression is decreased as compared to the $IC_{50}$ for an identical dsRNA formulation that does not contain the phase changing charge-trapped peptide, as measured in vivo or in vitro (see for example Hefner et al. J Biomol Tech. 2008 September: 19(4) 231-237; Zimmermann et al. Nature. 2006 May 4: 441(7089):111-114; Durcan et al. Mol Pharm. 2008 July-August; 5(4):559-566; Heidel et al. Proc Natl Acad Sci USA. 2007 Apr. 3: 104(14):5715-5721).

Various methodologies of the instant invention include step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent (e.g., DsiRNA) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A "phase changing charge-trapped peptide: oligonucleotide conjugate" according to the invention means that the phase changing charge-trapped peptide can be attached to the 5' or 3' end of the first strand or the 5' or 3' end of the second strand or to the 5' end of the first strand and the 5' end of the second strand, to the 5' end of the first strand and the 3' end of the second strand, to the 3' end of the first strand and the 5' end of the second strand or to the 3' end of the first strand and the 3' end of the second strand of a double stranded oligonucleotide, such as a dsRNA.

A phase changing charge-trapped peptide according to the invention can also be attached internally to an oligonucleotide, for example via a specific functional group on the amino acid residue (e.g., —SH group on Cys or amino group of Lys), to the first and/or second strand of the oligonucleotide.

In one embodiment, more than one phase changing peptide, for example a dimer, a trimer or a multitude of phase changing peptides or combination of phase changing peptides and non-phase changing peptides are attached to an oligonucleotide such as dsRNA. The non-phase changing peptides can for example function as targeting peptides.

As used herein, a "dimer" means two peptides that are conjugated to each other and wherein one of the two peptides is also conjugated to an oligonucleotide such as dsRNA. A dimer also means two peptides wherein each peptide is conjugated to a unique site on an oligonucleotide such as dsRNA.

As used herein, a "trimer" means three peptides that are conjugated to each other and wherein one of the three peptides is conjugated to an oligonucleotide such as dsRNA. A trimer also means three peptides wherein each peptide is conjugated to a unique site on an oligonucleotide such as dsRNA. A trimer also means three peptides wherein two of the three peptides are conjugated to each other and wherein one of the two peptides is also conjugated to an oligonucleotide such as dsRNA and a third peptide is conjugated to a unique site on an oligonucleotide such as dsRNA.

As used herein, a "multitude" means more than one peptide, for example 2, 3, 4, 5, 6, 7, 8, 9, 10 or more. The invention provides for an oligonucleotide such as a dsRNA that is conjugated to multiple peptides wherein the peptides are of the same or different sequences. In one embodiment, a multitude of peptides means one or more phase changing peptides and optionally one or more non phase changing peptides, such as targeting peptides.

A phase changing charge-trapped peptide of the invention optionally may be conjugated to an oligonucleotide such as a dsRNA. As used herein, conjugated means attached via any covalent or non-covalent association known in the art.

A phase changing charge-trapped peptide of the invention can be conjugated to an oligonucleotide such as a dsRNA via any amino acid residue in the peptide, e.g., the C-terminal amino acid of the C-terminus via the carboxyl group of the C-terminal amino acid or the N-terminal amino acid of the N-terminus via the α-amino group of the N-terminal amino acid or to a specific functional group on the amino acid residue (e.g., —SH group on Cys or amino group of Lys).

A phase changing charge-trapped peptide of the invention can be conjugated to an oligonucleotide such as a dsRNA of the invention via any amino acid residue internal in the phase changing charge-trapped peptide sequence, e.g., via the amino group of Lysine residues in the middle of the phase changing charge-trapped peptide sequence.

A phase changing charge-trapped peptide according to the invention can be conjugated to an oligonucleotide such as a dsRNA of the invention via a stable covalent linkage including but not limited to a zero-length linker, homobifunctional linker, heterobifunctional linker or a trifunctional linker (References: Bioconjugate Techniques, 1996. Greg T. Hermanson, Academic Press, San Diego, Calif.; Chemistry of Protein Conjugation and Cross-linking, 1991. Shan S. Wong, CRC Press, Boca Raton, Fla.).

As used herein, a "zero-length linker" means conjugation via a reaction where the reactants (e.g., the reactive groups on the oligonucleotides such as dsRNAs and the functional groups on the phase changing charge-trapped peptides, such as reactive groups on the amino acid side chains, free amino and carboxyl groups of the terminal amino acid residues, etc.) are condensed to form a conjugated molecule without a linker. A "zero-length linker" is formed, for example, by reacting a reactant of a phase changing peptide with the terminal reactant of an oligonucleotide such as a dsRNA. Examples of zero-length linking includes but are not limited to disulfides, amides, esters, thioesters, etc.

As used herein, a "homobifunctional linker" means conjugation with a linker having two similar functional groups. Examples of homobifunctional linkers include but are not limited to amino directed, carboxyl directed, sulfhydryl directed, etc.

As used herein, a "heterobifunctional linker" means conjugation with a linker having two dissimilar functional groups of different specificities. Examples of heterobifunctional linkers include but are not limited to combinations of amino and sulfhydryl directed, amino and carboxyl directed, carboxyl and sulfhydryl directed, etc.

As used herein, a "trifunctional linker" means conjugation with a linker having three reactive functional groups. Examples of trifunctional linkers include but are not limited to 4-azido-2-nitrophenylbiocytin-4-nitrophenyl ester (ABNP), sulfosuccinimidyl-2-[6-(biotinamido)-2-(p-azidobenzamido)hexanoamido]ethyl-1,3'-dithiopropionate (sulfo-SBED), other biocytin based molecules, etc.

A phase changing charge-trapped peptide according to the invention can also be conjugated to an oligonucleotide such as a dsRNA via a cleavable linker including but not limited to a disulfide, an ester, a glycol, a diazo, and a sulfone linker.

A phase changing charge-trapped peptide according to the invention can be conjugated to an oligonucleotide such as a dsRNA by a carbon linker, for example a carbon linker that is 1 or more carbons, for example, 1, 2, 3, 4, 5, 6, 7, 8, 9, 10, 11, 12, 13, 14, 15, 16, 17, 18, 19, 20, 21, 22, 23, 24, 25 or more carbons.

A phase changing charge-trapped peptide according to the invention can be conjugated to an oligonucleotide such as a dsRNA using a prosthetic group. Prosthetic groups include but are not limited to metal ions, porphyrin groups, coenzymes and other nonpeptidyl moieties, e.g., carbohydrates or oligosaccharides (Wong, S. S. (1991), Chemistry of protein conjugation and cross-linking, CRC Press).

In one embodiment, a phase changing charge-trapped peptide and an oligonucleotide such as a dsRNA are conjugated by expression as a fusion construct.

A "phase changing charge-trapped peptide" may be attached to an oligonucleotide such as a dsRNA by any conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press.

A "phase changing charge-trapped peptide" may be conjugated to an oligonucleotide such as a dsRNA non-covalently via ionic interactions.

As used herein, a "phase changing charge-trapped peptide-oligonucleotide conjugate" means a phase changing charge-trapped peptide that is conjugated to an oligonucleotide such as a dsRNA by a method including but not limited to the methods of attachment/conjugation described herein.

In one embodiment a phase changing charge-trapped peptide-oligonucleotide conjugate further comprises one or more dye molecules.

As used herein, a "dye molecule" includes but is not limited to a polyaromatic dye or a fluorescent dye, for example Cy3, Cy5, Cy5.5, Alexa Fluor® (e.g, Alexa Fluor 488, Alexa Fluor 555, Alexa Fluor 647, etc.)

In one embodiment, a phase changing charge-trapped peptide-oligonucleotide conjugate further comprises a delivery peptide, as defined herein.

In one embodiment, a phase changing charge-trapped peptide-oligonucleotide conjugate further comprises a therapeutic agent, for example, an anticancer agent or an agent that treats a metabolic disease or disorder. Anticancer agents include but are not limited to antiviral agents (Fiume et al. FEBS Lett. 1983; 153(1):6-10), cisplatin (Mukhopadhyay S et al., Bioconjug Chem. 2008; 19(1):39-49), doxorubicin (Guan H et al., Bioconjug Chem. 2008; 19(9):1813-21), paclitaxel (Dubikovskaya E A et al., Proc Natl Acad Sci USA. 2008; 105(34):12128-33, Rëgina A et al., Br J Pharmacol. 2008; 155(2):185-97), tamoxifen (Rickert et al. Biomacromolecules. 2007; 8(11):3608-3612) and vinblastine (DeFeo-Jones D et al., Mol Cancer Ther. 2002; 1(7): 451-459).

A "phase changing charge-trapped peptide-oligonucleotide conjugate" refers to a molecule wherein both of the peptide and the oligonucleotide retain their function.

As used herein, a test phase changing charge-trapped peptide means a peptide that when present as a component of a formulation comprising an oligonucleotide, such as an dsRNA, is a candidate peptide to be assessed for its properties relating to increasing cellular internalization and/or cytoplasmic release of an oligonucleotide such as a dsRNA As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this embodiment is meant nucleotide bases other than adenine, guanine, cytosine and uracil at 1' position or their equivalents.

An oligonucleotide according to the invention is a polymer of nucleotides, and can be single stranded or double stranded.

As used herein, dsRNA includes dsRNA molecules that are modeled to enter the RNAi pathway as substrates of the Dicer enzyme, at least in part due the strand lengths of such compositions, are also referred to as Dicer substrate siRNA ("DsiRNA") agents herein. The "DsiRNA agent" compositions of the instant invention comprise dsRNA which is a precursor molecule for Dicer enzyme processing, i.e., the DsiRNA of the present invention is processed in vivo to produce an active siRNA. Specifically, the DsiRNA is processed by Dicer to an active siRNA which is incorporated into RISC. This precursor molecule, primarily referred to as a "DsiRNA agent" or "DsiRNA molecule" herein, can also be referred to as a precursor RNAi molecule herein. As used herein, the term "active siRNA" refers to a double stranded nucleic acid in which each strand comprises RNA, RNA analog(s) or RNA and DNA. The siRNA comprises between 19 and 23 nucleotides or comprises 21 nucleotides. The active siRNA typically has 2 bp overhangs on the 3' ends of each strand such that the duplex region in the siRNA comprises 17-21 nucleotides, or 19 nucleotides.

In certain embodiments, dsRNAs of the invention include but are not limited to dsRNAs comprising first and second strands comprising between 16 and 50, 19 and 35, 19 and 24, 25 and 30, 25 and 35, 26 and 30, 21 and 23 nucleotides in length.

A DsiRNA agent of the instant invention has a length sufficient such that it is processed by Dicer to produce a siRNA. In certain embodiments, a suitable DsiRNA agent contains one oligonucleotide sequence, a first sequence, that is at least 25 nucleotides in length and no longer than about 35 nucleotides. This sequence of RNA can be between about 26 and 35, 26 and 34, 26 and 33, 26 and 32, 26 and 31, 26 and 30, and 26 and 29 nucleotides in length. This sequence can be about 27 or 28 nucleotides in length or 27 nucleotides in length. The second sequence of the DsiRNA agent can be any sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotides sequence will have about 21 or more complementary base pairs, or about 25 or more complementary base pairs with the first oligonucleotide sequence. In one embodiment, the second sequence is the same length as the first sequence, and the DsiRNA agent is blunt ended. In another embodiment, the ends of the DsiRNA agent have one or more overhangs. In certain embodiments, wherein the second sequence is the same length as the first sequence, the ultimate residue of the 3' terminus of the first strand and the ultimate residue of the 5' terminus of the second strand form a mismatched base pair. In other embodiments, wherein the second sequence is the same length as the first sequence, the ultimate residue of the 5' terminus of the first strand and the ultimate residue of the 3' terminus of the second strand form a mismatched base pair. In other embodiments, wherein the second sequence is the same length as the first sequence, the ultimate and penultimate residues of the 3' terminus of the first strand and the ultimate and penultimate residues of the 5' terminus of the second strand form two mismatched base pairs. In still other embodiments, wherein the second sequence is the same length as the first sequence, the ultimate and penultimate residues of the 5' terminus of the first strand and the ultimate and penultimate residues of the 3' terminus of the second strand form two mismatched base pairs.

In certain embodiments, the first and second oligonucleotide sequences of the DsiRNA agent exist on separate oligonucleotide strands that can be and typically are chemically synthesized. In some embodiments, both strands are between 26 and 35 nucleotides in length. In other embodiments, both strands are between 25 and 30 or 26 and 30 nucleotides in length. In one embodiment, both strands are 27 nucleotides in length, are completely complementary and have blunt ends. In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. In certain embodiments of the instant invention, the DsiRNA agent is comprised of two oligonucleotide strands of differing lengths, with the DsiRNA possessing a blunt end at the 3' terminus of a first strand (sense strand) and a 3' overhang at the 3' terminus of a second strand (antisense strand). The DsiRNA can also contain one or more deoxyribonucleic acid (DNA) base substitutions.

In certain embodiments, the DsiRNA can be a dsRNA molecule possessing strand lengths longer than 30 nucleotides in length. Such "extended DsiRNA" molecules (oligonucleotides) can have strand lengths of 30-70 or more nucleotides in length, e.g., 30-49 nucleotides in length (e.g., 30, 31, 32, 33, 34, 35, 36, 37, 38, 39, 40, 41, 42, 43, 44, 45, 46, 47, 48 or 49 nucleotide strand lengths), 30-60 nucleotides in length (e.g., including 50, 51, 52, 53, 54, 55, 56, 57, 58, 59 and 60 nucleotide strand lengths) or even dsRNAs possessing strand lengths of 61, 62, 63, 64, 65, 66, 67, 68, 69, 70 or more nucleotides in length. In certain embodiments, such "extended DsiRNA" molecules comprise one or more DNA:DNA base pairs within those regions of the "extended DsiRNA" molecule that are located outside of the region of the "extended DsiRNA" molecule that becomes an "active siRNA" following Dicer cleavage of the "extended DsiRNA" molecule, with such DNA:DNA base pairs also generally positioned three or more nucleotides upstream or downstream of the projected Dicer enzyme cleavage site(s) of the "extended DsiRNA" molecule. In certain other embodiments the "extended DsiRNA" molecule comprises four or more deoxynucleotide residues upon one or both strands of the "extended" regions of the "extended DsiRNA" molecule. As above, such "extended" regions are those that are located outside of the region of the "extended DsiRNA" molecule that becomes an "active siRNA" following Dicer cleavage of the "extended DsiRNA" molecule, and such deoxyribonucleotides of the "extended" region are also generally positioned three or more nucleotides upstream or downstream of the projected Dicer enzyme cleavage site(s) of the "extended DsiRNA" molecule.

As used herein, a dsRNA, e.g., DsiRNA or siRNA, having a sequence "sufficiently complementary" to a target RNA or cDNA sequence means that the dsRNA has a sequence sufficient to trigger the destruction of the target RNA (where a cDNA sequence is recited, the RNA sequence corresponding to the recited cDNA sequence) by the RNAi machinery (e.g., the RISC complex) or process. The dsRNA molecule can be designed such that every residue of the antisense strand is complementary to a residue in the target molecule. Alternatively, substitutions can be made within the molecule to increase stability and/or enhance processing activity of the molecule. Substitutions can be made within the strand or can be made to residues at the ends of the strand. In certain embodiments, substitutions and/or modifications are made at specific residues within a DsiRNA agent. Such substitutions and/or modifications can include, e.g., deoxy-modifications at one or more residues of positions 1, 2 and 3 when numbering from the 3' terminal position of the sense strand of a DsiRNA agent; deoxy-modifications at one or more residues of positions 1, 2, 3 or 4 when numbering from the 5' terminal position of the antisense strand of a DsiRNA agent and introduction of 2'-O-alkyl (e.g., 2'-O-methyl) modifications at the 3' terminal residue of the antisense strand of DsiRNA agents, with such modifications also or alternatively being present at overhang positions of the 3' portion of the antisense strand and/or throughout the DsiRNA agent, for example at alternating residues or in pairs of residues of the antisense strand of the DsiRNA that are included within the region of a DsiRNA agent that is processed to form an active siRNA agent. The preceding modifications are offered as exemplary, and are not intended to be limiting in any manner. Further consideration of the structure of preferred DsiRNA agents, including further description of the modifications and substitutions that can be performed upon the DsiRNA agents of the instant invention, can be found below.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, a DsiRNA molecule of the invention comprises about 19 to about 30 (e.g., about 19, 20, 21, 22, 23, 24, 25, 26, 27, 28, 29, or 30 or more) nucleotides that are complementary to one or more target nucleic acid molecules or a portion thereof.

The phrase "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region.

Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

Single-stranded nucleic acids that base pair over a number of bases are the to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (°

C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | Vender | Cat# | Lot# | m.w./Stock | To make 50 mL solution |
|---|---|---|---|---|---|---|
| NaCl | 100 mM | Sigma | S-5150 | 41K8934 | 5M | 1 mL |
| KCl | 80 mM | Sigma | P-9541 | 70K0002 | 74.55 | 0.298 g |
| MgCl$_2$ | 8 mM | Sigma | M-1028 | 120K8933 | 1M | 0.4 mL |
| sucrose | 2% w/v | Fisher | BP220-212 | 907105 | 342.3 | 1 g |
| Tris-HCl | 16 mM | Fisher | BP1757-500 | 12419 | 1M | 0.8 mL |
| NaH$_2$PO$_4$ | 1 mM | Sigma | S-3193 | 52H-029515 | 120.0 | 0.006 g |
| EDTA | 0.02 mM | Sigma | E-7889 | 110K89271 | 0.5M | 2 µL |
| H$_2$O pH = 7.0 at 20° C. | | Sigma | W-4502 | 51K2359 adjust with HCl | | to 50 mL |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

Certain dsRNAs of this invention can be chimeric double-stranded ribonucleic acids (dsRNAs). "Chimeric dsRNAs" or "chimeras", in the context of this invention, are dsRNAs which contain two or more chemically distinct regions, each made up of at least one nucleotide. These dsRNAs typically contain at least one region primarily comprising ribonucleotides (optionally including modified ribonucleotides) that form a Dicer substrate siRNA ("DsiRNA") molecule. This DsiRNA region can be covalently attached to a second region comprising base paired deoxyribonucleotides (a "dsDNA region") on either flank of the ribonucleotide duplex region, which can confer one or more beneficial properties (such as, for example, increased efficacy, e.g., increased potency and/or duration of DsiRNA activity, function as a recognition domain or means of targeting a chimeric dsNA to a specific location, for example, when administered to cells in culture or to a subject, functioning as an extended region for improved attachment of functional groups, payloads, detection/detectable moieties, functioning as an extended region that allows for more desirable modifications and/or improved spacing of such modifications, etc.). This second region, e.g., comprising base paired deoxyribonucleotides may also include modified or synthetic nucleotides and/or modified or synthetic deoxyribonucleotides.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide. As used herein, the term "deoxyribonucleotide" also includes a modified ribonucleotide that does not permit Dicer cleavage of a dsRNA agent, e.g., a 2'-O-methyl ribonucleotide, a phosphorothioate-modified ribonucleotide residue, etc., that does not permit Dicer cleavage to occur at a bond of such a residue.

As used herein, the term "PS-NA" refers to a phosphorothioate-modified nucleotide residue. The term "PS-NA" therefore encompasses both phosphorothioate-modified ribonucleotides ("PS-RNAs") and phosphorothioate-modified deoxyribonucleotides ("PS-DNAs").

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments about 19-25 nucleotides long, usually with a two-base overhang on the 3' end. With respect to the dsRNAs of the invention, the duplex formed by a dsRNA region of a dsRNA of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP_085124, hereby incorporated by reference.

Dicer "cleavage" is determined as follows (e.g., see Collingwood et al., Oligonucleotides 18:187-200 (2008)). In a Dicer cleavage assay, RNA duplexes (100 pmol) are incubated in 20 µL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-30 bp, dsRNA, preferably 26-30 bp dsRNA) is cleaved to a shorter dsRNA (e.g., 19-23 bp dsRNA, preferably, 21-23 bp dsRNA).

As used herein, "Dicer cleavage site" refers to the sites at which Dicer cleaves a dsRNA (e.g., the dsRNA region of a dsRNA of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae I, et al. (2006). "*Structural basis for double-stranded RNA processing by Dicer*". Science 311 (5758): 195-8.). Dicer is projected to cleave certain double-stranded nucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsRNA molecules distinct from those are known in the art or may be similarly identified via art-recognized methods, including those described in Macrae et al. Dicer cleavage of a dsRNA (e.g., DsiRNA) can result in generation of Dicer-processed siRNA lengths of 19 to 23 nucleotides in length. Indeed, in one embodiment of the invention that is described in greater detail below, a double stranded DNA region is included within a dsRNA for purpose of directing prevalent Dicer excision of a typically non-preferred 19 mer siRNA.

As used herein, "overhang" refers to unpaired nucleotides, in the context of a duplex having one, two, three, four or five free ends at either the 5' terminus or 3' terminus of a dsRNA. In certain embodiments, the overhang is a 3' or 5' overhang on the antisense strand or sense strand.

As used herein, the term "DmiRNA" refers to a species of Dicer substrate siRNA ("DsiRNA") that possesses at least one mismatch nucleotide within the antisense (guide) strand of the DmiRNA agent, specifically within the region of the antisense strand that functions as an RNA interference agent and is believed to hybridize with the sequence of a target RNA. Such mismatch nucleotide can exist either with respect to the sense (passenger) strand, with respect to the target RNA sequence to which the antisense strand of the DmiRNA is believed to hybridize, or with respect to both.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by any of several endo- or exonucleases (e.g., RNase III, RNase P, RNase T1, RNase A (1, 2, 3, 4/5), oligonucleotidase, etc.).

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the DsiRNA agents of the instant invention contemplates the possibility of using such DsiRNA agents not only against target RNAs of interest possessing perfect complementarity with the presently described DsiRNA agents, but also against target RNAs of interest possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to the DsiRNA agents. Similarly, it is contemplated that the presently described DsiRNA agents of the instant invention might be readily altered by the skilled artisan to enhance the extent of complementarity between the DsiRNA agents and a target RNA of interest, e.g., of a specific allelic variant (e.g., an allele of enhanced therapeutic interest). Indeed, DsiRNA agent sequences with insertions, deletions, and single point mutations relative to the target sequence of interest can also be effective for inhibition (possibly believed to act via microRNA-like translational inhibition, rather than destruction, of targeted transcripts; accordingly, such DsiRNA agents can be termed "DmiRNAs"). Alternatively, DsiRNA agent sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions ×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the DsiRNA antisense strand and a portion of the RNA sequence of interest is preferred. Alternatively, the DsiRNA may be defined functionally as a nucleotide sequence (or oligonucleotide sequence) that is capable of hybridizing with a portion of the RNA of interest (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (° C.)=81.5+ 16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4. The length of the identical nucleotide sequences may be at least about 10, 12, 15, 17, 20, 22, 25, 27 or 30 bases.

By "sense region" is meant a nucleotide sequence of a DsiRNA molecule having complementarity to an antisense region of the DsiRNA molecule. In addition, the sense region of a DsiRNA molecule can comprise a nucleic acid sequence having homology with a target nucleic acid sequence.

By "antisense region" is meant a nucleotide sequence of a DsiRNA molecule having complementarity to a target nucleic acid sequence. In addition, the antisense region of a DsiRNA molecule comprises a nucleic acid sequence having complementarity to a sense region of the DsiRNA molecule.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA.

As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least duplex with the antisense strand.

As used herein, "guide strand" refers to a single stranded nucleic acid molecule of a dsRNA or dsRNA-containing molecule, which has a sequence sufficiently complementary to that of a target RNA to result in RNA interference. After cleavage of the dsRNA or dsRNA-containing molecule by Dicer, a fragment of the guide strand remains associated with RISC, binds a target RNA as a component of the RISC complex, and promotes cleavage of a target RNA by RISC. As used herein, the guide strand does not necessarily refer to a continuous single stranded nucleic acid and may comprise a discontinuity, preferably at a site that is cleaved by Dicer. A guide strand is an antisense strand.

As used herein, "passenger strand" refers to an oligonucleotide strand of a dsRNA or dsRNA-containing molecule, which has a sequence that is complementary to that of the guide strand. As used herein, the passenger strand does not necessarily refer to a continuous single stranded nucleic acid and may comprise a discontinuity, preferably at a site that is cleaved by Dicer. A passenger strand is a sense strand.

By "target nucleic acid" is meant any nucleic acid sequence whose expression, level or activity is to be modulated. The target nucleic acid can be DNA or RNA. Levels of expression may also be targeted via targeting of upstream effectors of the target of interest, or the effects of a modulated or misregulated target may also be modulated by targeting molecules downstream of, for example, the signaling pathway of a target of interest.

As is known, RNAi methods are applicable to a wide variety of genes in a wide variety of organisms and the disclosed compositions and methods can be utilized in each of these contexts. Examples of genes which can be targeted by the disclosed compositions and methods include endogenous genes which are genes that are native to the cell or to genes that are not normally native to the cell. Without limitation these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

More specifically, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), ApoB100 and HPRT1.

In one embodiment, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Pathogens include RNA viruses such as flaviviruses, picornaviruses, rhabdoviruses, filoviruses, retroviruses, including lentiviruses, or DNA viruses such as adenoviruses, poxviruses, herpes viruses, cytomegaloviruses, hepadnaviruses or others. Additional pathogens include bacteria, fungi, helminths, schistosomes and trypanosomes. Other kinds of pathogens can include mammalian transposable elements. Alternatively, the protein may be a tumor-associated protein or an autoimmune disease-associated protein.

The target gene may be derived from or contained in any organism. The organism may be a plant, animal, protozoa, bacterium, virus or fungus. See e.g., U.S. Pat. No. 6,506, 559, incorporated herein by reference.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the DsiRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent (e.g., DsiRNA) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

In certain embodiments, suitable controls for methods involving the charge-trapped peptides of the invention can include the following: (a) for charge-trapped peptide-oligonucleotide conjugates, suitable controls for assessment of the characteristics of a charge-trapped peptide-oligonucleotide conjugate can include the oligonucleotide (e.g., dsRNA) in the absence of charge-trapped peptide, the oligonucleotide in the presence of unattached charge-trapped peptide, the charge-trapped peptide in the absence of oligonucleotide, and/or, optionally, in any of the preceding three contexts, an appropriate control for the cyclic charge-trapped peptide may involve substitution of the cyclic charge-trapped peptide with a corresponding linear form of the peptide, with a corresponding cyclic form of the peptide having protected residues in place of one or all of the charged residues of the charge-trapped peptide, or other suitable control; (b) for charge-trapped peptides in formulation, one or more controls recited in (a) can be "Treatment", or "treating" as used herein, is defined as the application or administration of a therapeutic agent (e.g., a DsiRNA agent or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment. The invention encompasses the identification of and use of a phase changing charge-trapped peptide, as defined herein, to provide an oligonucleotide-phase changing charge-trapped peptide conjugate, e.g., a dsRNA-phase changing charge-trapped peptide conjugate. The phase changing charge-trapped peptide enhances the cellular uptake and/or cytoplasmic release of an oligonucleotide as compared to the same oligonucleotide in the absence of the phase changing charge-trapped peptide. To be effective, the phase changing charge-trapped peptide is not required to be conjugated to the oligonucleotide. Compositions and formulations comprising the phase changing charge-trapped peptide and oligonucleotides can be used in one embodiment to modulate the levels of an RNA or encoded protein of interest.

Without wishing to be bound by theory, it is appreciated in the context of the instant invention that any discharge of energy (e.g., mechanical energy, dispersion of trapped charge) from a peptide of the instant invention in response to a change in the peptide's context (e.g., introduction of the peptide to a reducing environment, e.g., within an endocytic pathway of a cell) can be harnessed to disrupt or otherwise alter the structure of a formulation particle comprising such a peptide. In certain embodiments, therefore, a charge-trapped peptide of the invention is cyclized by any available cyclization method—such cyclization methods include, but are not limited to, Cys-Cys linkages, Citruline-Valine (Cit-Val) or (Val-Cit) linkages, and other cyclization methods including both amino acid- and non-amino acid-reliant means of joining the ends of a peptide sequence. Examples of Cys-Cys cyclized peptides of the instant invention include, but are not limited to, the following:

$$c[CK[(K)_aH(K)_b]_n(K)_cH(K)_dC] \quad \text{(SEQ ID NO: 1)}$$

where c[ ] indicates cyclic peptide through Cys-Cys disulfide linkage and a, b, c, d and n are independently 0-5

$$c[CR[(R)_aH(R)_b]_n(R)_cH(R)_dC] \quad \text{(SEQ ID NO: 2)}$$

where c[ ] indicates cyclic peptide through Cys-Cys disulfide linkage and a, b, c, d and n are independently 0-5

$$c[C[(K)_aH(K)_b]_nC] \quad \text{(SEQ ID NO: 3)}$$

where c[ ] indicates cyclic peptide through Cys-Cys disulfide linkage and a, b are independently 0-5 and n is 1-10

$$c[C[(R)_aH(R)_b]_nC] \quad \text{(SEQ ID NO: 4)}$$

where c[ ] indicates cyclic peptide through Cys-Cys disulfide linkage and a, b are independently 0-5 and n is 1-10

$$c[C[(K)_ax(K)_by(K)_cz]_nC] \quad \text{(SEQ ID NO: 5)}$$

where c[ ] indicates cyclic peptide through Cys-Cys disulfide linkage and a, b, c are independently 0-5 and n is 1-5; x, y, and z are any amino acid except Lysine $$c[C[(R)_ax(R)_by(R)_cz]_nC] \quad \text{(SEQ ID NO: 6)}$$

where c[ ] indicates cyclic peptide through Cys-Cys disulfide linkage and a, b, c are independently 0-5 and n is 1-5; x, y, and z are any amino acid except Arginine
Specific exemplary cyclized peptides of the invention also include the following:

TABLE 2

Exemplary Cyclized Peptides of the Invention

| | | |
|---|---|---|
| c809 | c[CGRRRRRRRRRSC] | (SEQ ID NO: 7) |
| c810 | c[CGRHRHRHRHRSC] | (SEQ ID NO: 8) |
| c811 | c[CGRHDRHDRHDSC] | (SEQ ID NO: 9) |
| c812 | c[CGRKKRRQRRRPPQSC] | (SEQ ID NO: 10) |
| c813 | c[CGRHKHRQRHRPPQSC] | (SEQ ID NO: 11) | where c[ ] indicates cyclic peptide through Cys-Cys disulfide linkage.

Cyclization can also be performed upon non-cyclized peptides synthesized by combining one or more sequences from infra (e.g., cyclize a peptide with sequence from the N-terminal to the C-terminal of c[C-SEQ ID NO:7-SEQ ID NO:8-C], c[C-SEQ ID NO:8-SEQ ID NO:7-C]; etc.). It is also appreciated that cyclization can be performed upon a peptide such as those of the instant invention in a manner that involves joining of non-terminal residues of the peptide (by way of example, Cys residues shown in the above peptides may be migrated to internal regions of the same peptides for purpose of cyclizing shorter regions of the same peptides via joining of a non-terminal Cys residue with, e.g., either a terminal or other non-terminal Cys residue).

Without wishing to be bound by theory, cyclization of the peptides of the instant invention is appreciated as advantageous as allowing for "trapping" of the charged residues of a peptide within one structure upon synthesis (e.g., under non-reducing and/or high pH conditions), with release of the "trapped" charges within such a cyclized peptide then occurring upon introduction of the peptide to conditions under which the cyclizing linkage is released (e.g., a reducing and/or low pH environment, e.g., within the endocytic pathway of a cell). By way of example, it is also appreciated that poly-lysine and/or poly-arginine rich peptides of the instant invention can be made to possess altered $pK_a$s within a charge "trapping", cyclized form, versus a relaxed, non-cyclized form (with such effect modeled as attributable to packing of charges into confined proximity in the cyclized state of such a peptide). Accordingly, cyclization of charged peptides of the invention can be used to store potential energy in the form of such "trapped" charges (optionally in addition to storage of mechanical and/or other forms of potential energy within such peptides of the instant invention). Indeed, also without wishing to be bound by theory, in certain aspects of the invention, the use of highly charged peptide sequences for cyclization enhances the release of mechanical energy triggered at the moment of breakage of the cyclizing bond of such peptides, due to release of electrostatic repulsive forces, which in turn translates into mechanical energy.

Thus, the cyclic structure of the peptides of the invention can allow for potential energy to be stored within phase-changing charge-trapped peptides in a number of distinct manners. By way of example, in the cyclized peptides of Table 2 above, the act of cyclization effectively traps mechanical and charge energy within the cyclized peptide.

The peptide may also harbor membrane-integrating and/or disrupting potential energy in the form of, e.g., a kink modeled to exist within the peptide that is critical for membrane insertion. Introduction of such a peptide into a reducing and/or low pH environment is modeled to release trapped energy via disruption of the disulfide (or other method)-mediated cyclization imposed upon the peptide at synthesis, as well as via proper exposure of the modeled kink within the peptide contributing to membrane integration and/or particle disruption.

Also without wishing to be bound by theory, in addition to trapping electrostatic/mechanical potential energy, the cyclic structures of the charge-trapped peptides of the invention are also believed to be capable of reducing toxicity of such highly charged "pore forming" peptides, relative to a linear peptide possessing the same sequence, as breakage of the cyclizing bond within, e.g., a low pH environment (e.g., the endosome), is required for realization of the "pore forming" effect of such peptides (modeled to be active as "pore forming" only when linearized), meaning that the linearized form of such peptides would be preferentially exposed to e.g., endosomal membranes, and not non-specifically to all membranes. Thus, to the extent that "pore forming" peptides are toxic when systemically administered as linear peptides, such toxicity can be reduced via cyclization of such peptides with a pH sensitive linker (e.g., a disulfide).

In certain embodiments, the cyclic charge-trapped peptides of the invention are included as formulation components in the absence of attachment to payload or other formulation components. In some embodiments, a cyclic charge-trapped peptide of the invention is attached to a payload or other formulation component via a non-covalent or covalent linkage. In one embodiment, a cyclic charge-trapped peptide of the invention is attached to the 5'-terminus of the guide strand of a DsiRNA payload (or, optionally, to any other terminus of guide or passenger strand of a DsiRNA payload) via a covalent linker. In such embodiments, it may be desirable to insert a lysine (K) residue at a site within a cyclic peptide sequence as exemplified herein (e.g., cyclic peptides of SEQ ID NOs: 2, 4, 6 and cyclic peptides of Table 2), for purpose of providing a site of linker attachment that also carries positive charge. For example, an extra lysine residue can be introduced into the "c809" cyclic peptide of Table 2 above (forming sequence "c809K9"—see Table 3 below) for purpose of attaching a covalently-linked DsiRNA, e.g., as depicted graphically in FIG. 4. It is noted with respect to FIG. 4 that in certain embodiments, the linker that joins a charge-trapped peptide of the invention and a DsiRNA is independently cleavable, i.e., de-cyclization (linearization) of charge-trapped peptide and release of the charge-trapped peptide from DsiRNA can be either dependent or independent events.

Exemplary cyclic charge-trapped peptide sequences presenting additional lysine residues include the following:

TABLE 3

Additional Exemplary Charge-Trapped Peptides for Covalent Attachment

| c809K2 | c[CKGRRRRRRRRRSC] (SEQ ID NO: 12) |
| c809K3 | c[CGKRRRRRRRRRSC] (SEQ ID NO: 13) |
| c809K4 | c[CGRKRRRRRRRRSC] (SEQ ID NO: 14) |
| c809K5 | c[CGRRKRRRRRRRSC] (SEQ ID NO: 15) |
| c809K6 | c[CGRRRKRRRRRRSC] (SEQ ID NO: 16) |
| c809K7 | c[CGRRRRKRRRRRSC] (SEQ ID NO: 17) |
| c809K8 | c[CGRRRRRKRRRRSC] (SEQ ID NO: 18) |
| c809K9 | c[CGRRRRRRKRRRSC] (SEQ ID NO: 19) |

TABLE 3-continued

Additional Exemplary Charge-Trapped Peptides for Covalent Attachment

| c809K10 | c[CGRRRRRRRKRRSC] (SEQ ID NO: 20) |
| c809K11 | c[CGRRRRRRRRKRSC] (SEQ ID NO: 21) |
| c809K12 | c[CGRRRRRRRRRKSC] (SEQ ID NO: 22) |
| c809K13 | c[CGRRRRRRRRRSKC] (SEQ ID NO: 23) |
| c810K2 | c[CKGRHRHRHRHRSC] (SEQ ID NO: 24) |
| c810K3 | c[CGKRHRHRHRHRSC] (SEQ ID NO: 25) |
| c810K4 | c[CGRKHRHRHRHRSC] (SEQ ID NO: 26) |
| c810K5 | c[CGRHKRHRHRHRSC] (SEQ ID NO: 27) |
| c810K6 | c[CGRHRKHRHRHRSC] (SEQ ID NO: 28) |
| c810K7 | c[CGRHRHKRHRHRSC] (SEQ ID NO: 29) |
| c810K8 | c[CGRHRHRKHRHRSC] (SEQ ID NO: 30) |
| c810K9 | c[CGRHRHRHKRHRSC] (SEQ ID NO: 31) |
| c810K10 | c[CGRHRHRHRKHRSC] (SEQ ID NO: 32) |
| c810K11 | c[CGRHRHRHRHKRSC] (SEQ ID NO: 33) |
| c810K12 | c[CGRHRHRHRHRKSC] (SEQ ID NO: 34) |
| c810K13 | c[CGRHRHRHRHRSKC] (SEQ ID NO: 35) |
| c811K2 | c[CKGRHDRHDRHDSC] (SEQ ID NO: 36) |
| c811K3 | c[CGKRHDRHDRHDSC] (SEQ ID NO: 37) |
| c811K4 | c[CGRKHDRHDRHDSC] (SEQ ID NO: 38) |
| c811K5 | c[CGRHKDRHDRHDSC] (SEQ ID NO: 39) |
| c811K6 | c[CGRHDKRHDRHDSC] (SEQ ID NO: 40) |
| c811K7 | c[CGRHDRKHDRHDSC] (SEQ ID NO: 41) |
| c811K8 | c[CGRHDRHKDRHDSC] (SEQ ID NO: 42) |
| c811K9 | c[CGRHDRHDKRHDSC] (SEQ ID NO: 43) |
| c811K10 | c[CGRHDRHDRKHDSC] (SEQ ID NO: 44) |
| c811K11 | c[CGRHDRHDRHKDSC] (SEQ ID NO: 45) |
| c811K12 | c[CGRHDRHDRHDKSC] (SEQ ID NO: 46) |
| c811K13 | c[CGRHDRHDRHDSKC] (SEQ ID NO: 47) | where c[ ] indicates cyclic peptide through Cys-Cys disulfide linkage.

As noted above, cyclization of the above peptides can also be performed via other art-recognized methods, e.g., Citrulline-Valine linkage. Accordingly, in such embodiments, the terminal cysteine residues of the above peptides are not required. Such peptides can therefore be represented as follows:

(SEQ ID NO: 48)
$c[K[(K)_aH(K)_b]_n(K)_cH(K)_d]$ where c[ ] indicates cyclic peptide through any art recognized linkage (e.g., Citrulline-Valine) and a, b, c, d and n are independently 0-5

$$c[R[(R)_aH(R)_b]_n(R)_cH(R)_d] \quad \text{(SEQ ID NO: 49)}$$

where c[ ] indicates cyclic peptide through any art recognized linkage (e.g., Citrulline-Valine) and a, b, c, d and n are independently 0-5

$$c[[(K)_aH(K)_b]_n] \quad \text{(SEQ ID NO: 50)}$$

where c[ ] indicates cyclic peptide through any art recognized linkage (e.g., Citrulline-Valine) and a, b are independently 0-5 and n is 1-10

$$c[[(R)_aH(R)_b]_n] \quad \text{(SEQ ID NO: 51)}$$

where c[ ] indicates cyclic peptide through any art recognized linkage (e.g., Citrulline-Valine) and a, b are independently 0-5 and n is 1-10

$$c[[(K)_ax(K)_bY(K)_cz]n] \quad \text{(SEQ ID NO: 52)}$$

where c[ ] indicates cyclic peptide through any art recognized linkage (e.g., Citrulline-Valine) and a, b, c are independently 0-5 and n is 1-5; x, y, and z are any amino acid except Lysine $$c[[(R)_ax(R)_bY(R)_cz]_n] \quad \text{(SEQ ID NO: 53)}$$

where c[ ] indicates cyclic peptide through any art recognized linkage (e.g., Citrulline-Valine) and a, b, c are independently 0-5 and n is 1-5; x, y, and z are any amino acid except Arginine Specific exemplary cyclized peptides of the invention also include the following:

TABLE 4

Exemplary Cyclized Peptides of the Invention

| c809 | c[GRRRRRRRRRS] (SEQ ID NO: 54) |
|---|---|
| c810 | c[GRHRHRHRHRS] (SEQ ID NO: 55) |
| c811 | c[GRHDRHDRHDS] (SEQ ID NO: 56) |
| c812 | c[GRKKRRQRRRPPQS] (SEQ ID NO: 57) |
| c813 | c[GRHKHRQRHRPPQS] (SEQ ID NO: 58) | where c[ ] indicates cyclic peptide through any art recognized linkage (e.g., Citrulline-Valine).

TABLE 5

Further Exemplary Charge-Trapped Peptides, Readily Covalently Attached

| c809K2a | c[KGRRRRRRRRRS] (SEQ ID NO: 59) |
|---|---|
| c809K3a | c[GKRRRRRRRRRS] (SEQ ID NO: 60) |
| c809K4a | c[GRKRRRRRRRRS] (SEQ ID NO: 61) |
| c809K5a | c[GRRKRRRRRRRS] (SEQ ID NO: 62) |
| c809K6a | c[GRRRKRRRRRRS] (SEQ ID NO: 63) |
| c809K7a | c[GRRRRKRRRRRS] (SEQ ID NO: 64) |
| c809K8a | c[GRRRRRKRRRRS] (SEQ ID NO: 65) |
| c809K9a | c[GRRRRRRKRRRS] (SEQ ID NO: 66) |
| c809K10a | c[GRRRRRRRKRRS] (SEQ ID NO: 67) |
| c809K11a | c[GRRRRRRRRKRS] (SEQ ID NO: 68) |
| c809K12a | c[GRRRRRRRRRKS] (SEQ ID NO: 69) |
| c809K13a | c[GRRRRRRRRRSK] (SEQ ID NO: 70) |
| c810K2a | c[KGRHRHRHRHRS] (SEQ ID NO: 71) |
| c810K3a | c[GKRHRHRHRHRS] (SEQ ID NO: 72) |
| c810K4a | c[GRKHRHRHRHRS] (SEQ ID NO: 73) |
| c810K5a | c[GRHKRHRHRHRS] (SEQ ID NO: 74) |
| c810K6a | c[GRHRKHRHRHRS] (SEQ ID NO: 75) |
| c810K7a | c[GRHRHKRHRHRS] (SEQ ID NO: 76) |
| c810K8a | c[GRHRHRKHRHRS] (SEQ ID NO: 77) |
| c810K9a | c[GRHRHRHKRHRS] (SEQ ID NO: 78) |
| c810K10a | c[GRHRHRHRKHRS] (SEQ ID NO: 79) |
| c810K11a | c[GRHRHRHRHKRS] (SEQ ID NO: 80) |
| c810K12a | c[GRHRHRHRHRKS] (SEQ ID NO: 81) |
| c810K13a | c[GRHRHRHRHRSK] (SEQ ID NO: 82) |
| c811K2a | c[KGRHDRHDRHDS] (SEQ ID NO: 83) |
| c811K3a | c[GKRHDRHDRHDS] (SEQ ID NO: 84) |
| c811K4a | c[GRKHDRHDRHDS] (SEQ ID NO: 85) |
| c811K5a | c[GRHKDRHDRHDS] (SEQ ID NO: 86) |
| c811K6a | c[GRHDKRHDRHDS] (SEQ ID NO: 87) |
| c811K7a | c[GRHDRKHDRHDS] (SEQ ID NO: 88) |
| c811K8a | c[GRHDRHKDRHDS] (SEQ ID NO: 89) |
| c811K9a | c[GRHDRHDKRHDS] (SEQ ID NO: 90) |
| c811K10a | c[GRHDRHDRKHDS] (SEQ ID NO: 91) |
| c811K11a | c[GRHDRHDRHKDS] (SEQ ID NO: 92) |
| c811K12a | c[GRHDRHDRHDKS] (SEQ ID NO: 93) |
| c811K13a | c[GRHDRHDRHDSK] (SEQ ID NO: 94) | where c[ ] indicates cyclic peptide through any art recognized linkage (e.g., Citrulline-Valine).

Additional exemplary charge-trapped peptides of the invention include the following peptides, which are also predicted to be pore-forming peptides:

Cyclic Melitin and Derivatives:

$$c[GIGAVLKVLTTGLPALISWIKRKRQQ] \quad \text{(SEQ ID NO: 95)}$$

where c[ ] indicates cyclic peptide through any art recognized linkage (e.g., Cys-Cys, Citrulline-Valine, etc.).

Cyclic Defensin and Derivatives:

(SEQ ID NO: 96)
c[ATCDLLSGTGINHSACAAHCLLRGNRGGYCNGKGVCVCRN]

where c[ ] indicates cyclic peptide through any art recognized linkage (e.g., Cys-Cys, Citrulline-Valine, etc.).

(SEQ ID NO: 97)
c[GFGCPLNQGACHRHCRSIRRRGGYCAGFFKQTCTCYRN]

where c[ ] indicates cyclic peptide through any art recognized linkage (e.g., Cys-Cys, Citrulline-Valine, etc.).
Cyclic Pilosulin and Derivatives:

(SEQ ID NO: 98)
c[GLGSVFGRLARILGRVIPKVAKKLGPKVAKVLPKVMKEAIPMAVEMAK

SQEEQQPQ]

where c[ ] indicates cyclic peptide through any art recognized linkage (e.g., Cys-Cys, Citrulline-Valine, etc.).
Cyclic Magainin and Derivatives:

(SEQ ID NO: 99)
c[GIGKFLHSAKKFGKAFVGEIMNS]

where c[ ] indicates cyclic peptide through any art recognized linkage (e.g., Cys-Cys, Citrulline-Valine, etc.).
Cyclic Lycotoxin and Derivatives:

(SEQ ID NO: 100)
c[KIKWFKTMKSIAKFIAKEQMKKFILGGE]

where c[ ] indicates cyclic peptide through any art recognized linkage (e.g., Cys-Cys, Citrulline-Valine, etc.).
Cyclic NK-Lysin and Derivatives:

(SEQ ID NO: 101)
c[GYFCESCRKIIQKLEDMVGPQPNEDTVTQAASQVCDKLKILRGLCKKI

MRSFLRRISWDILTGKKPQAICVDIKICKE]

where c[ ] indicates cyclic peptide through any art recognized linkage (e.g., Cys-Cys, Citrulline-Valine, etc.).
Cyclic PrP and Derivatives:

(SEQ ID NO: 102)
c[KTNMKHMAGAAAAGAVVGGLG]

where c[ ] indicates cyclic peptide through any art recognized linkage (e.g., Cys-Cys, Citrulline-Valine, etc.).
Cyclic AβP and Derivatives:

(SEQ ID NO: 103)
c[DAEFRHDSGYEVHHQKLVFFAEDVGSNKGAIIGLMVGGVV]

where c[ ] indicates cyclic peptide through any art recognized linkage (e.g., Cys-Cys, Citrulline-Valine, etc.).
Cyclic Amylin and Derivatives:

(SEQ ID NO: 104)
c[KCNTATCATQRLANFLVHSSNNFGAILSSTNVGSNTY]

where c[ ] indicates cyclic peptide through any art recognized linkage (e.g., Cys-Cys, Citrulline-Valine, etc.).

Cyclic Lys-Leu Peptides and Derivatives:

(SEQ ID NO: 105)
c[KLLKLLLKLLKLLLKLLLKLLK]

where c[ ] indicates cyclic peptide through any art recognized linkage (e.g., Cys-Cys, Citrulline-Valine, etc.).

In certain embodiments, the exemplary cyclic peptides recited herein include derivatives of such peptides, with derivatives of such peptides defined as peptides that are truncated forms of the peptides presented herein, peptides that include internal and/or terminal additions of amino acids/peptides, peptides possessing significant levels of homology/identity with those recited herein (e.g., at least 50% identity, at least 75% identity, at least 80% identity, at least 85% identity, at least 90% identity, at least 95% identity or more, as compared to a peptide sequence recited herein), peptides that include one or more internal and/or terminal conjugation sequence(s) (e.g., Cys, Lys, PEG, alkyl amine, alkyl sulfhydryl, etc.).

It is noted that certain charge-trapped peptides described herein (e.g., above peptides SEQ ID NOs:95-105) are designed to exhibit reduced toxicity when formulated in particles (e.g., lipid nanoparticles) as compared to a formulation comprising the linear peptide, or as compared to a free-peptide that is not encapsulated in particles.

Without wishing to be bound by theory, linearization of a charge-trapped peptide of the invention releases potential energy and may impact the conformation of a single peptide in isolation or a population of associated peptides, lipids, or other molecules present within or in the environs of a formulation comprising the charge-trapped peptide. Such release of trapped potential energy (here, "charge-trapped" potential energy) is associated with induction of a phase-change of the composition/formulation that is, in turn, associated with improved delivery of a payload associated with the charge-trapped peptide.

Libraries comprising expression vectors encoding species of one or more of the above consensus sequences of phase changing charge-trapped peptides can be used to screen for those phase changing charge-trapped peptides most effective in cytoplasmically releasing the oligonucleotide of the administered formulation comprising the oligonucleotide and the phase changing charge-trapped peptide.

Peptide Synthesis

There are at least four ways to obtain a peptide: (1) purification from biological system (e.g., tissue, serum, urine, etc.); (2) purification of peptide fragment after digestion of a protein; (3) genetic engineering and recombinant technologies and (4) direct chemical synthesis. The first two approaches are often impractical due to the lack of control over the peptide sequences. The first approach also suffers from low concentration of peptide in biological samples that requires significant concentrating steps prior to purification. Typically, therefore, for shorter peptides direct chemical synthesis is an attractive option, whereas, for larger peptide recombinant technology is a better choice.

Traditional synthetic approaches of organic chemistry are generally impractical for peptides with more than four or five amino acid residues due to the complexities of amino acids and peptides. The problems include multiple reactive groups in the peptide and purifying the product after each step or synthesizing a series of different peptide mixtures that are impurity to the peptide of interest.

The advent of solid phase peptide synthesis (Merrifield, 1962) in which peptide is synthesized while keeping it attached at one end to a solid support provided the major breakthrough in the direct chemical synthesis of peptides. Today, most solid phase peptide syntheses involve FMOC chemistry. Briefly, chemical synthesis proceeds from the carboxyl terminus (C terminus) to the amino terminus (N terminus). The solid phase support is an insoluble polymer or resin. The 9-fluorenyl-methoxycarbonyl (FMOC) group prevents unwanted reactions at the α-amino group of the amino acid residue. The peptide is built on a resin support one amino acid at a time using a standard set of reactions in a repeating cycle. First, the C-terminal amino acid with it α-amino group protected by FMOC group is attached to the reactive group on the resin. The protecting group on the α-amino group of the amino acid attached to the resin is removed, generally with a mild organic base. Now, the resin with the C-terminal amino acid is ready to receive the second amino acid of the peptide. Each amino acid is received protected with different chemistries at the α-amino group (FMOC) and carboxyl group (generally, Dicyclohexylcarbodiimide, DCC). The carboxyl group of the second amino acid is activated by removing DCC and reacted with the deprotected α-amino group of the first amino acid on the solid support to form the peptide bond.

At each successive step in the cycle, protective chemical groups block unwanted reactions and the sequence of (i) deprotection of the α-amino group on the nascent peptide; (ii) activation of the carboxyl group on the next amino acid and (iii) reaction to form peptide bond continues until the entire peptide sequence is synthesized. When the peptide synthesis is complete, the linkage between the resin and the peptide is cleaved off to obtain the final peptide. The state-of-the-art solid phase peptide synthesis technology is automated, and several kinds of commercial instruments are now available.

Since the solid phase synthesis is a stepwise process for longer peptides it has the important limitation of lower overall yield and therefore increased cost. For example, with a 96% stepwise yield, the overall yield for 21 mer, 51 mer and 100 mer peptides are 44%, 13% and 1.7%, respectively. Similarly, with a 99.8% stepwise yield, the overall yield for 21 mer, 51 mer and 100 mer peptides are 96%, 90% and 82%, respectively. Therefore, for longer peptides it is more cost- and time-effective to genetically engineer the sequence in an expression cassette and express them in appropriate expression system (e.g., microbial expression system such as E. coli or yeast) or mammalian expression system (cell culture). For smaller peptides, however, the cost of genetically engineering the sequence and expressing and purifying the peptides are generally not cost- and time-effective compared to the solid phase peptide synthesis.

In certain embodiments, the "charge-trapped" peptides of the instant invention are initially synthesized with protected amino acid residues (e.g., Fmoc-amino acids, Boc-amino acids, etc.), wherein cyclic forms are produced prior to de-protection. Such a process of initial synthesis/cyclization in a protected state allows for greater charge-trapping within individual cyclic peptides of the invention, as the full extent of charge-trapping is only realized upon deprotection of such residues, resulting in a cyclic peptide possessing greater charge density than might otherwise be achieved in the absence of such synthesis scheme (protection, cyclization/steric hindrance of protected amino acid residues, de-protection).

Peptide for the current invention could be synthesized, expressed or purified using the methods described above or other methods of synthesis, expression or purification known in the art.

Peptide Charge

Positively charged amino acids are Lysine (Lys, K), Arginine (Arg, R) and Histidine (His, H). Negatively charged amino acids are Aspartic acid or aspartate (Asp, D), Glutamic acid or glutamate (Glu, E). Overall isoelectric point (pI) value of the peptide depends on the primary sequence and especially the presence, number and location of the above mentioned charged amino acid residues.

Histidine, an essential amino acid, has a positively charged imidazole functional group. The imidazole makes it a common participant in enzyme catalyzed reactions. The unprotonated imidazole is nucleophilic and can serve as a general base, while the protonated form can serve as a general acid. The residue can also serve a role in inducible structures of peptides and proteins. The imidazole sidechain of histidine has a pKa of approximately 6, and overall, the amino acid has a pKa of 7.6. This means that at physiologically relevant pH values, relatively small shifts in pH will change its average charge. In the endocytic vesicles, as pH falls below a pH of 6, the imidazole ring becomes protonated as described by the Henderson-Hasselbalch equation. When protonated, the imidazole ring bears two NH bonds and has a positive charge. The positive charge is equally distributed between both nitrogens and can be represented with two equally important resonance structures (Lehninger Principles of Biochemistry, 3rd Ed., 2000. Edited by David L. Nelson and Michael M. Cox, Worth Publishers, New York, N.Y.).

Conjugation Chemistry

Conjugation is performed either on the sense or antisense strands or both and either on the 3' end or 5' end or both. Conjugation is performed to any amino acid residues in the peptide, e.g., the C-terminal or N-terminal amino acid residues with either terminal α-amino group, carboxyl group or to specific function group on the amino acid residue (e.g., —SH group on Cys).

Any conjugation chemistry for peptide or protein known in the art maybe utilized with appropriate end group choice on the dsRNAs.

In one embodiment 5' end of the antisense strand is synthesized with the —(CH$_2$)$_6$—NH$_2$ linker and conjugated to the —SH group of Cys using maleimide chemistry to form a stable conjugate. In another embodiment 3' end of the sense strand is synthesized—(CH$_2$)$_6$—SH linker and conjugated to the —SH group of Cys via disulfide exchange to form a cleavable conjugate. dsRNA-peptide conjugates are purified and characterized for identity and purity with standard analytical methods.

Formulation of RNA and RNA Derivatives

Formulation of oligonucleotides in "vesicle-based" particle (Judge et al., 2009 and references therein; Noble et al., 2009 and references therein); Abrams et al., 2009 and references therein) and other particulate/liposomal/micellar formulations (Ko et al., 2009 and references therein; Mangala et al., 2009 and references therein) are described in literature and known in the art. For dsRNA formulation containing peptide that is not covalently attached to the dsRNA (referred throughout the text as dsRNA and peptide formulation), formulations are prepared with both dsRNA and peptide in the aqueous phase of the formulation. For dsRNA-peptide conjugation formulation, test articles are prepared with both dsRNA and peptide in the aqueous phase of the formulation.

Exemplary DsiRNA Structures

In certain embodiments, the charge-trapped peptides of the instant invention are conjugated and/or formulated with a DsiRNA oligonucleotide (a.k.a. a "DsiRNA molecule" or "DsiRNA agent"). Exemplary DsiRNA structures include the following.

In one such embodiment, the DsiRNA comprises:

wherein "X"=RNA and "Y" is an overhang domain comprised of 1-4 RNA monomers that are optionally 2'-O-methyl RNA monomers. In a related embodiment, the DsiRNA comprises:

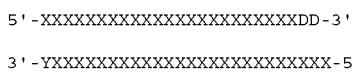

wherein "X"=RNA, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand.

DsiRNAs of the invention can carry a broad range of modification patterns (e.g., 2'-O-methyl RNA patterns, e.g., within extended DsiRNA agents). Certain modification patterns of the second strand of DsiRNAs of the invention are presented below.

In one embodiment, the DsiRNA comprises:

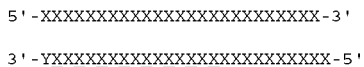

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

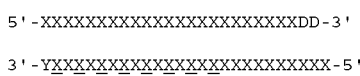

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers, and "D"=DNA. The top strand is the sense strand, and the bottom strand is the antisense strand.

In another such embodiment, the DsiRNA comprises:

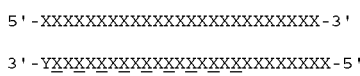

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

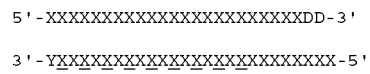

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another such embodiment, the DsiRNA comprises:

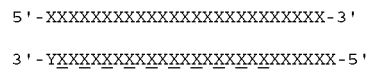

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

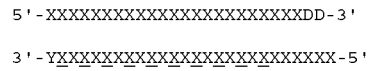

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In further embodiments, the DsiRNA comprises:

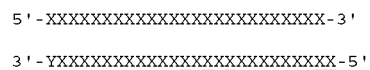

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

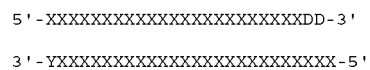

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

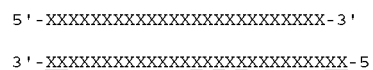

wherein "X"=RNA and "X"=2'-O-methyl RNA. In a further related embodiment, the DsiRNA comprises:

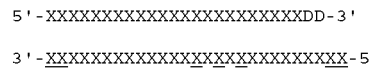

wherein "X"=RNA, "X̲"=2'-O-methyl RNA, and "D"=DNA. The top strand is the sense strand, and the bottom strand is the antisense strand. This modification pattern is also referred to herein as the "AS-M7" or "M7" modification pattern.

In additional embodiments, the DsiRNA comprises:

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

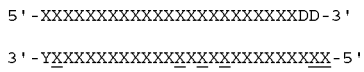

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. The top strand is the sense strand, and the bottom strand is the antisense strand. In another related embodiment, the DsiRNA comprises:

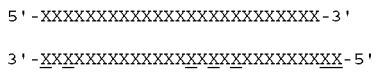

wherein "X"=RNA and "X̲"=2'-O-methyl RNA. The top strand is the sense strand, and the bottom strand is the antisense strand. In a further related embodiment, the DsiRNA comprises:

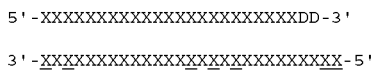

wherein "X"=RNA, "X̲"=2'-O-methyl RNA, and "D"=DNA. The top strand is the sense strand, and the bottom strand is the antisense strand. This modification pattern is also referred to herein as the "AS-M6" or "M6" modification pattern.

In other embodiments, the DsiRNA comprises:

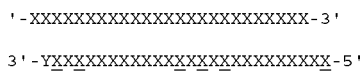

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

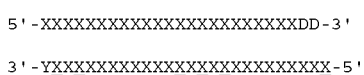

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

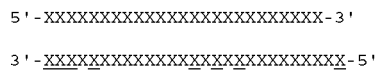

wherein "X"=RNA and "X̲"=2'-O-methyl RNA. The top strand is the sense strand, and the bottom strand is the antisense strand. In another related embodiment, the DsiRNA comprises:

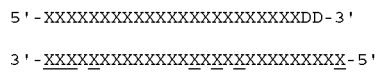

wherein "X"=RNA, "X̲"=2'-O-methyl RNA, and "D"=DNA. The top strand is the sense strand, and the bottom strand is the antisense strand. This modification pattern is also referred to herein as the "AS-M5" or "M5" modification pattern.

In further embodiments, the DsiRNA comprises:

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

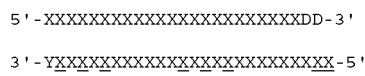

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

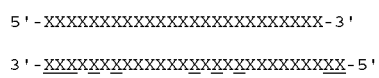

wherein "X"=RNA and "X̲"=2'-O-methyl RNA. The top strand is the sense strand, and the bottom strand is the antisense strand. In a further related embodiment, the DsiRNA comprises:

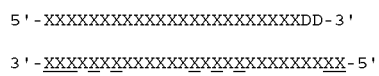

wherein "X"=RNA, "X̲"=2'-O-methyl RNA, and "D"=DNA. The top strand is the sense strand, and the bottom strand is the antisense strand. This modification pattern is also referred to herein as the "AS-M4" or "M4" modification pattern.

In additional embodiments, the DsiRNA comprises:

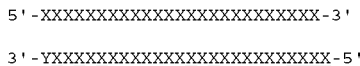

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

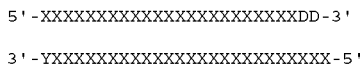

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

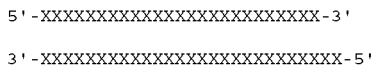

wherein "X"=RNA and "X"=2'-O-methyl RNA. The top strand is the sense strand, and the bottom strand is the antisense strand. In a further related embodiment, the DsiRNA comprises:

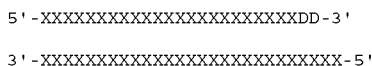

wherein "X"=RNA, "X"=2'-O-methyl RNA, and "D"=DNA. The top strand is the sense strand, and the bottom strand is the antisense strand. This modification pattern is also referred to herein as the "AS-M8" or "M8" modification pattern.

In other embodiments, the DsiRNA comprises:

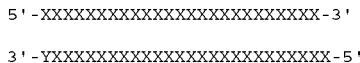

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

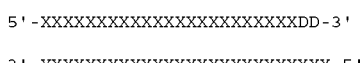

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

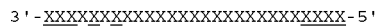

wherein "X"=RNA and "X"=2'-O-methyl RNA. The top strand is the sense strand, and the bottom strand is the antisense strand. In a further related embodiment, the DsiRNA comprises:

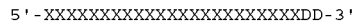
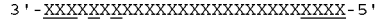

wherein "X"=RNA, "X"=2'-O-methyl RNA, and "D"=DNA. The top strand is the sense strand, and the bottom strand is the antisense strand. This modification pattern is also referred to herein as the "AS-M3" or "M3" modification pattern.

In additional embodiments, the DsiRNA comprises:

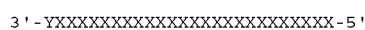

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

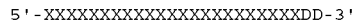
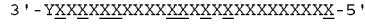

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

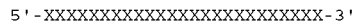

wherein "X"=RNA and "X"=2'-O-methyl RNA. The top strand is the sense strand, and the bottom strand is the antisense strand. In a further related embodiment, the DsiRNA comprises:

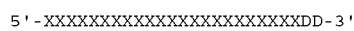
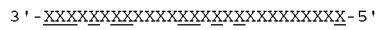

wherein "X"=RNA, "X"=2'-O-methyl RNA, and "D"=DNA. The top strand is the sense strand, and the bottom strand is the antisense strand. This modification pattern is also referred to herein as the "AS-M2" or "M2" modification pattern.

In further embodiments, the DsiRNA comprises:

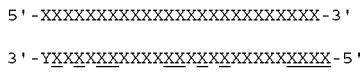

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

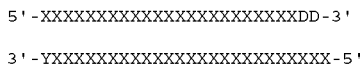

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

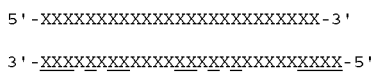

wherein "X"=RNA and "X"=2'-O-methyl RNA. The top strand is the sense strand, and the bottom strand is the antisense strand. In a further related embodiment, the DsiRNA comprises:

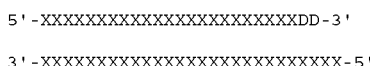

wherein "X"=RNA, "X"=2'-O-methyl RNA, and "D"=DNA. The top strand is the sense strand, and the bottom strand is the antisense strand. This modification pattern is also referred to herein as the "AS-M1" or "M1" modification pattern.

In additional embodiments, the DsiRNA comprises:

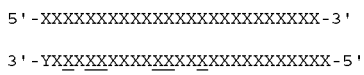

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

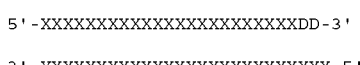

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

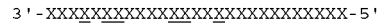

wherein "X"=RNA and "X"=2'-O-methyl RNA. The top strand is the sense strand, and the bottom strand is the antisense strand. In a further related embodiment, the DsiRNA comprises:

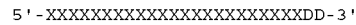

wherein "X"=RNA, "X"=2'-O-methyl RNA, and "D"=DNA. The top strand is the sense strand, and the bottom strand is the antisense strand. This modification pattern is also referred to herein as the "AS-M9" or "M9" modification pattern.

In other embodiments, the DsiRNA comprises:

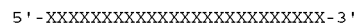
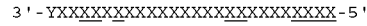

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

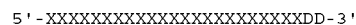
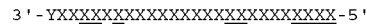

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

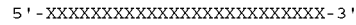
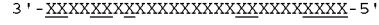

wherein "X"=RNA and "X"=2'-O-methyl RNA. The top strand is the sense strand, and the bottom strand is the antisense strand. In a further related embodiment, the DsiRNA comprises:

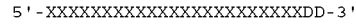
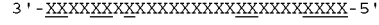

wherein "X"=RNA, "X"=2'-O-methyl RNA, and "D"=DNA. The top strand is the sense strand, and the bottom strand is the antisense strand. This modification pattern is also referred to herein as the "AS-M10" or "M10" modification pattern.

In further embodiments, the DsiRNA comprises:

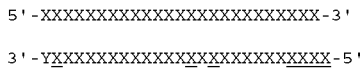

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

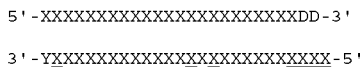

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

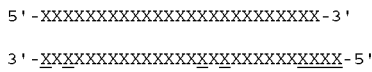

wherein "X"=RNA and "X"=2'-O-methyl RNA. The top strand is the sense strand, and the bottom strand is the antisense strand. In a further related embodiment, the DsiRNA comprises:

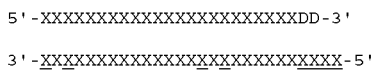

wherein "X"=RNA, "X"=2'-O-methyl RNA, and "D"=DNA. The top strand is the sense strand, and the bottom strand is the antisense strand. This modification pattern is also referred to herein as the "AS-M11" or "M11" modification pattern.

In additional embodiments, the DsiRNA comprises:

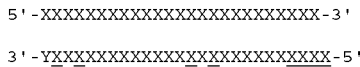

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

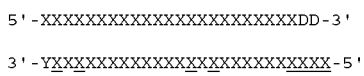

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

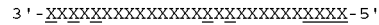

wherein "X"=RNA and "X"=2'-O-methyl RNA. The top strand is the sense strand, and the bottom strand is the antisense strand. In a further related embodiment, the DsiRNA comprises:

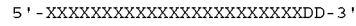
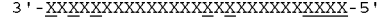

wherein "X"=RNA, "X"=2'-O-methyl RNA, and "D"=DNA. The top strand is the sense strand, and the bottom strand is the antisense strand. This modification pattern is also referred to herein as the "AS-M12" or "M12" modification pattern.

In further embodiments, the DsiRNA comprises:

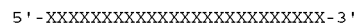
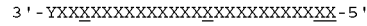

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

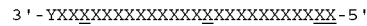

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

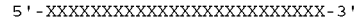
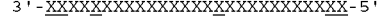

wherein "X"=RNA and "X"=2'-O-methyl RNA. The top strand is the sense strand, and the bottom strand is the antisense strand. In a further related embodiment, the DsiRNA comprises:

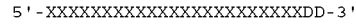
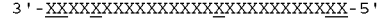

wherein "X"=RNA, "X"=2'-O-methyl RNA, and "D"=DNA. The top strand is the sense strand, and the bottom strand is the antisense strand. This modification pattern is also referred to herein as the "AS-M13" or "M13" modification pattern.

In other embodiments, the DsiRNA comprises:

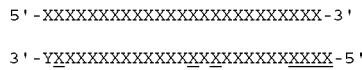

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In another related embodiment, the DsiRNA comprises:

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

wherein "X"=RNA and "X"=2'-O-methyl RNA. The top strand is the sense strand, and the bottom strand is the antisense strand. In a further related embodiment, the DsiRNA comprises:

wherein "X"=RNA, "X"=2'-O-methyl RNA, and "D"=DNA. The top strand is the sense strand, and the bottom strand is the antisense strand. This modification pattern is also referred to herein as the "AS-M21" or "M21" modification pattern.

In further embodiments, the DsiRNA comprises:

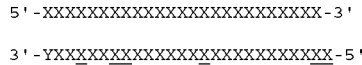

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

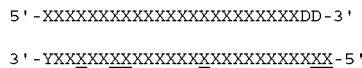

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

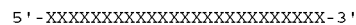
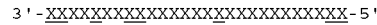

wherein "X"=RNA and "X"=2'-O-methyl RNA. The top strand is the sense strand, and the bottom strand is the antisense strand. In a further related embodiment, the DsiRNA comprises:

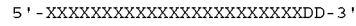
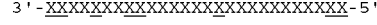

wherein "X"=RNA, "X"=2'-O-methyl RNA, and "D"=DNA. The top strand is the sense strand, and the bottom strand is the antisense strand. This modification pattern is also referred to herein as the "AS-M14" or "M14" modification pattern.

In additional embodiments, the DsiRNA comprises:

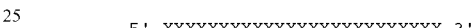
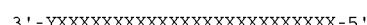

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

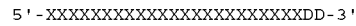
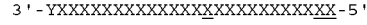

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

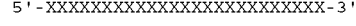
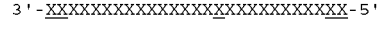

wherein "X"=RNA and "X"=2'-O-methyl RNA. The top strand is the sense strand, and the bottom strand is the antisense strand. In a further related embodiment, the DsiRNA comprises:

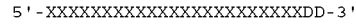
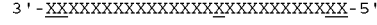

wherein "X"=RNA, "X"=2'-O-methyl RNA, and "D"=DNA. The top strand is the sense strand, and the bottom strand is the antisense strand. This modification pattern is also referred to herein as the "AS-M15" or "M15" modification pattern.

In further embodiments, the DsiRNA comprises:

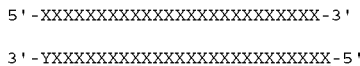

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

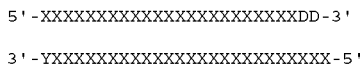

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

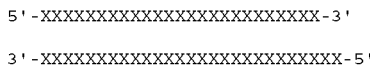

wherein "X"=RNA and "X̲"=2'-O-methyl RNA. The top strand is the sense strand, and the bottom strand is the antisense strand. In a further related embodiment, the DsiRNA comprises:

wherein "X"=RNA, "X̲"=2'-O-methyl RNA, and "D"=DNA. The top strand is the sense strand, and the bottom strand is the antisense strand. This modification pattern is also referred to herein as the "AS-M16" or "M16" modification pattern.

In additional embodiments, the DsiRNA comprises:

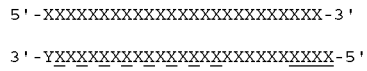

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

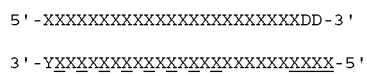

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

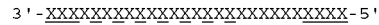

wherein "X"=RNA and "X̲"=2'-O-methyl RNA. The top strand is the sense strand, and the bottom strand is the antisense strand. In a further related embodiment, the DsiRNA comprises:

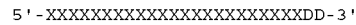

wherein "X"=RNA, "X̲"=2'-O-methyl RNA, and "D"=DNA. The top strand is the sense strand, and the bottom strand is the antisense strand. This modification pattern is also referred to herein as the "AS-M17" or "M17" modification pattern.

In further embodiments, the DsiRNA comprises:

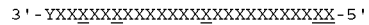

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

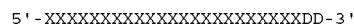
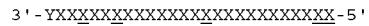

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

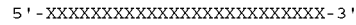
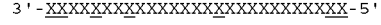

wherein "X"=RNA and "X̲"=2'-O-methyl RNA. The top strand is the sense strand, and the bottom strand is the antisense strand. In a further related embodiment, the DsiRNA comprises:

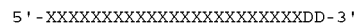
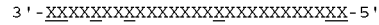

wherein "X"=RNA, "X̲"=2'-O-methyl RNA, and "D"=DNA. The top strand is the sense strand, and the bottom strand is the antisense strand. This modification pattern is also referred to herein as the "AS-M18" or "M18" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M19" or "M19" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M20" or "M20" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M22" or "M22" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M24" or "M24" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M25" or "M25" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M26" or "M26" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M27" or "M27" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M29" or "M29" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M30" or "M30" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M31" or "M31" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M32" or "M32" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M34" or "M34" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

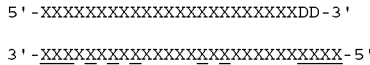

wherein "X"=RNA, "X̲"=2'-O-methyl RNA, and "D"=DNA. The top strand is the sense strand, and the bottom strand is the antisense strand. This modification pattern is also referred to herein as the "AS-M35" or "M35" modification pattern.

In further embodiments, the DsiRNA comprises:

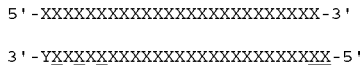

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

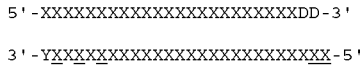

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

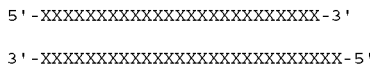

wherein "X"=RNA and "X̲"=2'-O-methyl RNA. The top strand is the sense strand, and the bottom strand is the antisense strand. In a further related embodiment, the DsiRNA comprises:

wherein "X"=RNA, "X̲"=2'-O-methyl RNA, and "D"=DNA. The top strand is the sense strand, and the bottom strand is the antisense strand. This modification pattern is also referred to herein as the "AS-M37" or "M37" modification pattern.

In additional embodiments, the DsiRNA comprises:

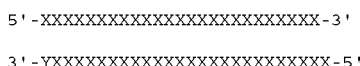

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

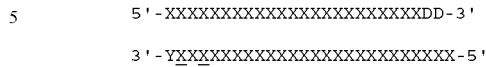

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

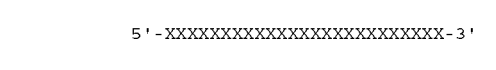

wherein "X"=RNA and "X̲"=2'-O-methyl RNA. The top strand is the sense strand, and the bottom strand is the antisense strand. In a further related embodiment, the DsiRNA comprises:

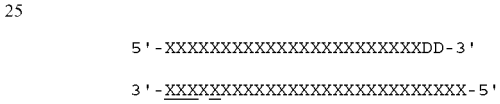

wherein "X"=RNA, "X̲"=2'-O-methyl RNA, and "D"=DNA. The top strand is the sense strand, and the bottom strand is the antisense strand. This modification pattern is also referred to herein as the "AS-M38" or "M38" modification pattern.

In further embodiments, the DsiRNA comprises:

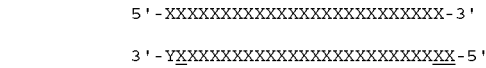

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

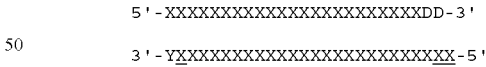

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

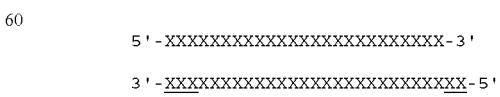

wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M40" or "M40" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M41" or "M41" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M7*" or "M7*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M6*" or "M6*" modification pattern.

In other embodiments, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In another related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M5*" or "M5*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M4*" or "M4*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M8*" or "M8*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M2*" or "M2*" modification pattern.

In other embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M10*" or "M10*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M11*" or "M11*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M13*" or "M13*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M14*" or "M14*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

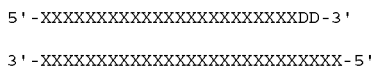

wherein "X"=RNA, "X̲"=2'-O-methyl RNA, and "D"=DNA. The top strand is the sense strand, and the bottom strand is the antisense strand. This modification pattern is also referred to herein as the "AS-M15*" or "M15*" modification pattern.

In further embodiments, the DsiRNA comprises:

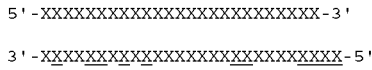

wherein "X"=RNA and "X̲"=2'-O-methyl RNA. The top strand is the sense strand, and the bottom strand is the antisense strand. In a further related embodiment, the DsiRNA comprises:

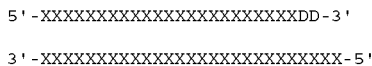

wherein "X"=RNA, "X̲"=2'-O-methyl RNA, and "D"=DNA. The top strand is the sense strand, and the bottom strand is the antisense strand. This modification pattern is also referred to herein as the "AS-M16*" or "M16*" modification pattern.

In additional embodiments, the DsiRNA comprises:

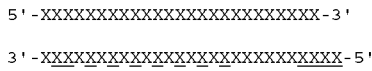

wherein "X"=RNA and "X̲"=2'-O-methyl RNA. The top strand is the sense strand, and the bottom strand is the antisense strand. In a further related embodiment, the DsiRNA comprises:

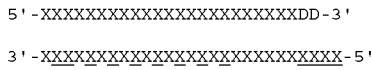

wherein "X"=RNA, "X̲"=2'-O-methyl RNA, and "D"=DNA. The top strand is the sense strand, and the bottom strand is the antisense strand. This modification pattern is also referred to herein as the "AS-M17*" or "M17*" modification pattern.

In further embodiments, the DsiRNA comprises:

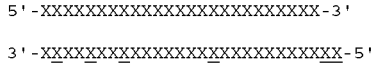

wherein "X"=RNA and "X̲"=2'-O-methyl RNA. The top strand is the sense strand, and the bottom strand is the antisense strand. In a further related embodiment, the DsiRNA comprises:

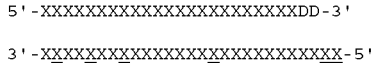

wherein "X"=RNA, "X̲"=2'-O-methyl RNA, and "D"=DNA. The top strand is the sense strand, and the bottom strand is the antisense strand. This modification pattern is also referred to herein as the "AS-M18*" or "M18*" modification pattern.

In additional embodiments, the DsiRNA comprises:

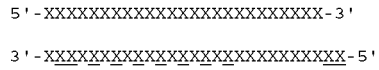

wherein "X"=RNA and "X̲"=2'-O-methyl RNA. The top strand is the sense strand, and the bottom strand is the antisense strand. In a further related embodiment, the DsiRNA comprises:

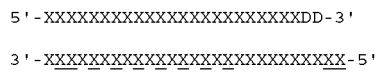

wherein "X"=RNA, "X̲"=2'-O-methyl RNA, and "D"=DNA. The top strand is the sense strand, and the bottom strand is the antisense strand. This modification pattern is also referred to herein as the "AS-M19*" or "M19*" modification pattern.

In further embodiments, the DsiRNA comprises:

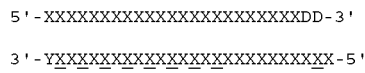

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

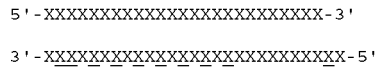

wherein "X"=RNA and "X̲"=2'-O-methyl RNA. The top strand is the sense strand, and the bottom strand is the antisense strand. In a further related embodiment, the DsiRNA comprises:

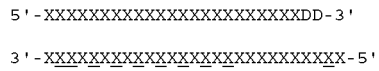

wherein "X"=RNA, "X̲"=2'-O-methyl RNA, and "D"=DNA. The top strand is the sense strand, and the bottom strand is the antisense strand. This modification pattern is also referred to herein as the "AS-M20*" or "M20*" modification pattern.

In additional embodiments, the DsiRNA comprises:

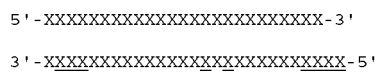

wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M22*" or "M22*" modification pattern.

In further embodiments the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M24*" or "M24*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M25*" or "M25*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M26*" or "M26*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M27*" or "M27*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M28*" or "M28*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M29*" or "M29*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M34*" or "M34*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M35*" or "M35*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M37*" or "M37*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M38*" or "M38*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M40*" or "M40*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M41*" or "M41*" modification pattern.

In certain embodiments, the sense strand of a DsiRNA of the invention is modified—specific exemplary forms of sense strand modifications are shown below, and it is contemplated that such modified sense strands can be substituted for the sense strand of any of the DsiRNAs shown above to generate a DsiRNA comprising a below-depicted sense strand that anneals with an above-depicted antisense strand. Exemplary sense strand modification patterns include:

```
5'-XXXXXXXXXXXXXXXXXXXXXXXXXDD-3'    "SM1"
5'-XXXXXXXXXXXXXXXXXXXXXXXXXDD-3'    "SM2"
5'-XXXXXXXXXXXXXXXXXXXXXXXXXDD-3'    "SM3"
5'-XXXXXXXXXXXXXXXXXXXXXXXXXDD-3'    "SM4"
5'-XXXXXXXXXXXXXXXXXXXXXXXXXDD-3'    "SM5"
5'-XXXXXXXXXXXXXXXXXXXXXXXXXDD-3'    "SM6"
5'-XXXXXXXXXXXXXXXXXXXXXXXXXDD-3'    "SM7"
5'-XXXXXXXXXXXXXXXXXXXXXXXXXDD-3'    "SM8"
5'-XXXXXXXXXXXXXXXXXXXXXXXXXDD-3'    "SM9"
5'-XXXXXXXXXXXXXXXXXXXXXXXXXDD-3'    "SM10"
5'-XXXXXXXXXXXXXXXXXXXXXXXXXDD-3'    "SM11"
5'-XXXXXXXXXXXXXXXXXXXXXXXXXDD-3'    "SM12"
5'-XXXXXXXXXXXXXXXXXXXXXXXXXDD-3'    "SM13"
5'-XXXXXXXXXXXXXXXXXXXXXXXXXDD-3'    "SM14"
5'-XXXXXXXXXXXXXXXXXXXXXXXXXDD-3'    "SM15"
5'-XXXXXXXXXXXXXXXXXXXXXXXXXDD-3'    "SM16"
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
``` where "X"=RNA, "$\underline{X}$"=2'-O-methyl RNA, and "D"=DNA.

The above modification patterns can also be incorporated into, e.g., the extended DsiRNA structures and mismatch and/or frayed DsiRNA structures described below.

In another embodiment, the DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary 27 mer DsiRNA agent with two terminal mismatched residues is shown:

```
5'-pXXXXXXXXXXXXXXXXXXXXXXXXXM M M-3'
3'-XXXXXXXXXXXXXXXXXXXXXXXXXX M Mp-5'
``` wherein "X"=RNA, "p"=a phosphate group, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand is the sense strand, and the bottom strand is the antisense strand. Alternatively, the bottom strand is the sense strand and the top strand is the antisense strand.

In certain additional embodiments, the present invention provides compositions for RNA interference (RNAi) that possess one or more base paired deoxyribonucleotides within a region of a double stranded ribonucleic acid (dsRNA) that is positioned 3' of a projected sense strand Dicer cleavage site and correspondingly 5' of a projected antisense strand Dicer cleavage site. The compositions of the invention comprise a dsRNA which is a precursor molecule, i.e., the dsRNA of the present invention is processed in vivo to produce an active small interfering nucleic acid (siRNA). The dsRNA is processed by Dicer to an active siRNA which is incorporated into RISC.

In certain embodiments, the DsiRNA agents of the invention can have the following exemplary structures (noting that any of the following exemplary structures can be combined, e.g., with the bottom strand modification patterns of the above-described structures—in one specific example, the bottom strand modification pattern shown in any of the above structures is applied to the 27 most 3' residues of the bottom strand of any of the following structures; in another specific example, the bottom strand modification pattern shown in any of the above structures upon the 23 most 3' residues of the bottom strand is applied to the 23 most 3' residues of the bottom strand of any of the following structures):

In one embodiment, the DsiRNA comprises the following (an exemplary "right-extended", "DNA extended" DsiRNA):

```
5'-XXXXXXXXXXXXXXXXXXXXXXXXX_{N*}D_{N}DD-3'
3'-YXXXXXXXXXXXXXXXXXXXXXXXXX_{N*}D_{N}XX-5'
``` wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

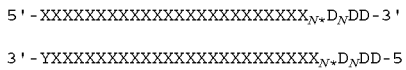

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In another embodiment, the DsiRNA comprises:

wherein "X"=RNA, "$\underline{X}$"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

wherein "X"=RNA, "$\underline{X}$"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

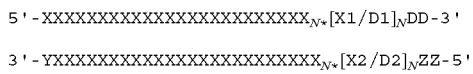

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In the structures depicted herein, the 5' end of either the sense strand or antisense strand can optionally comprise a phosphate group.

In another embodiment, the DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

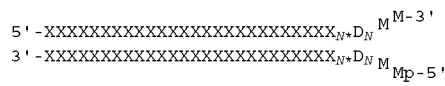

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-8 or 1-10. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In one embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. An exemplary structure for such a molecule is shown:

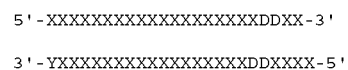

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21 mer duplex as its primary post-processing form. In embodiments where the bottom strand of the above structure is the antisense strand, the positioning of two deoxyribonucleotide residues at the ultimate and penultimate residues of the 5' end of the antisense strand is likely to reduce off-target effects (as prior studies have shown a 2'-O-methyl modification of at least the penultimate position from the 5' terminus of the antisense strand to reduce off-target effects; see, e.g., US 2007/0223427).

In one embodiment, the DsiRNA comprises the following (an exemplary "left-extended", "DNA extended" DsiRNA):

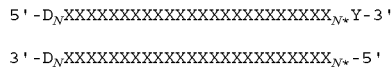

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

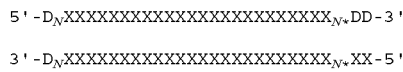

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In another embodiment, the DsiRNA comprises:

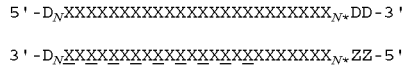

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

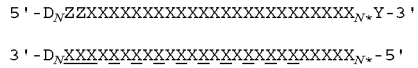

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

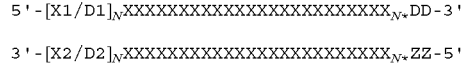

wherein "X"=RNA, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

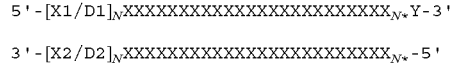

wherein "X"=RNA, "D"=DNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "N"=1 to 50 or more, but is optionally 1-8 or 1-10, where at least one D1$_N$ is present in the top strand and is base paired with a corresponding D2$_N$ in the bottom strand. Optionally, D1$_N$ and D1$_{N+1}$ are base paired with corresponding D2$_N$ and D2$_{N+1}$; D1$_N$, D1$_{N+1}$ and D1$_{N+2}$ are base paired with corresponding D2$_N$, D1$_{N+1}$ and D1$_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

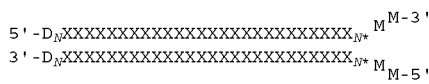

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-8 or 1-10. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In another embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. An exemplary structure for such a molecule is shown:

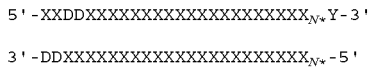

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21 mer duplex as its primary post-processing form. In embodiments where the bottom strand of the above structure is the antisense strand, the positioning of two deoxyribonucleotide residues at the ultimate and penultimate residues of the 5' end of the antisense strand is likely to reduce off-target effects (as prior studies have shown a 2'-O-methyl modification of at least the penultimate position from the 5' terminus of the antisense strand to reduce off-target effects; see, e.g., US 2007/0223427).

In certain embodiments, the "D" residues of the above structures include at least one PS-DNA or PS-RNA. Optionally, the "D" residues of the above structures include at least one modified nucleotide that inhibits Dicer cleavage.

While the above-described "DNA-extended" DsiRNA agents can be categorized as either "left extended" or "right extended", DsiRNA agents comprising both left- and right-extended DNA-containing sequences within a single agent (e.g., both flanks surrounding a core dsRNA structure are dsDNA extensions) can also be generated and used in similar manner to those described herein for "right-extended" and "left-extended" agents.

In some embodiments, the DsiRNA of the instant invention further comprises a linking moiety or domain that joins the sense and antisense strands of a DNA:DNA-extended DsiRNA agent. Optionally, such a linking moiety domain joins the 3' end of the sense strand and the 5' end of the antisense strand. The linking moiety may be a chemical (non-nucleotide) linker, such as an oligomethylenediol linker, oligoethylene glycol linker, or other art-recognized linker moiety. Alternatively, the linker can be a nucleotide linker, optionally including an extended loop and/or tetralloop.

In one embodiment, the DsiRNA agent has an asymmetric structure, with the sense strand having a 25-base pair length, and the antisense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxynucleotides at the 3' end of the sense strand.

In another embodiment, the DsiRNA agent has an asymmetric structure, with the antisense strand having a 25-base pair length, and the sense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxynucleotides at the 3' end of the antisense strand.

In certain embodiments, the DsiRNA agent can also be further attached to an aptamer (e.g., a delivery aptamer).

Selection Methods/Functionality Assay

Cell Uptake or Internalization dsRNAs, dsRNA and peptide and dsRNA-peptide conjugate formulations containing fluorescent tag are incubated in vitro in cell culture models to establish comparative uptake or internalization of different formulation. Appropriate cell culture models are utilized. Fluorescently-labeled peptides, either formulated or as naked molecules with or without transfection reagents are transfected in vitro in cell culture models to screen peptides for their phase changing properties.

Induced Leakiness

Formulations are prepared as previously described. Leakiness of the formulations is measured at different pH and different oxidation-reduction conditions by monitoring the release of calcein (van Rossenberg et al., J Biol Chem. 2002; 277(48):45803-10) using a fluorescence plate reader. Complete release of calcein from formulations is achieved by adding Triton X-100 to a final concentration of 0.25%.

Delivery dsRNAs, dsRNA and peptide and dsRNA-peptide conjugate formulations are transfected in vitro in cell culture models to establish comparative uptake or delivery of the dsRNAs, dsRNA and peptide and dsRNA-peptide conjugates. Appropriate cell culture models are utilized and end point measurements include, but not limited to, one or more of the following: (i) mRNA quantification using qPCR; (ii) protein quantification using Western blot; (iii) labelled cell internalization of dsRNAs, dsRNA and peptide and dsRNA-peptide conjugate formulations. Comparative uptake or deliveries of the dsRNAs, dsRNA and peptide and dsRNA-peptide conjugate formulations are assessed for both the extent and duration of the above mentioned end points.

In one example, transfection is performed in 24- or 48-well plates for transfecting dsRNAs or dsRNA-peptide conjugates into HeLa cells. Prior to application, dsRNAs, dsRNA and peptide and dsRNA-peptide conjugate formulations are diluted to the cell culture media at room temperature for about 30 min. For dose-response experiments, the final concentration of dsRNAs, dsRNA and peptide and dsRNA-peptide conjugate formulations applied are varied within a range of 0 to 50 nM. For the time-course experiment, an optimum concentration from the dose-experiment is studied for various incubation times, e.g., 30 min to 7 days.

Functionality of peptide, dsRNA, dsRNA and peptide and dsRNA-peptide conjugate formulations are also tested by differentially labeling the peptide and the dsRNA with fluorescent tags and performing fluorescent colocalization studies. Peptide is tagged with a green fluorescent dye and the dsRNAs tagged with red florescent dye. Using this methodology, and comparison with the free (i.e., unconjugated) dsRNA formulations confirm the ability of the peptide to facilitate internalize both the peptide alone, peptide as an excipient to the dsRNA formulation and dsRNA-peptide conjugate formulations. Peptides ability to deliver fluorescent label attached or dsRNAs conjugated are measured by both measuring the total fluorescence inside the cell, measuring the fluorescent that is not stably associated with endosomal or lysosomal compartment as dsRNAs need to not only reach inside the cell, but also to reach cytoplasm of the cell to trigger RNAi. Conducting fluorescent localization and cellular trafficking studies are described in the art (Lu, Langer and Chen. Mol Pharm. 2009; McNaughton et al., Proc Natl Acad Sci USA. 2009).

Effective phase changing charge-trapped peptides are in one embodiment those that achieved improvement of functionalization of the dsRNA-peptide conjugate formulation compared to dsRNA formulation alone is about 25%. In another embodiment the achieved improvement of functionalization of the dsRNA-peptide conjugate formulation compared to dsRNA formulation alone is about 100%, i.e., the dsRNA-peptide conjugate formulation show about 2-fold delivery compared to dsRNA formulation alone. In another embodiment the dsRNA-peptide conjugate formulation show about 5-fold delivery compared to dsRNA formulation alone. In another embodiment the dsRNA-peptide conjugate formulation show about 10-fold delivery compared to dsRNA formulation alone. In another embodiment the dsRNA-peptide conjugate formulation show about 100-fold delivery compared to dsRNA formulation alone. In another embodiment the dsRNA-peptide conjugate formulation show about 1,000-fold or more delivery compared to dsRNA formulation alone. These specifications are also applicable for formulation containing dsRNA and non-covalently conjugated peptide, compared to dsRNA formulation alone.

EXAMPLES

The present invention is described by reference to the following Examples, which are offered by way of illustration and are not intended to limit the invention in any manner. Standard techniques well known in the art or the techniques specifically described below were utilized.

Example 1

Preparation of Double-Stranded RNA Oligonucleotides

Oligonucleotide Synthesis and Purification dsRNA (e.g., DsiRNA) molecules can be designed to interact with various sites in the RNA message, for example, target sequences within the RNA sequences described herein. Exemplified dsRNA molecules were chemically synthesized using methods described herein. For exemplified DsiRNAs, such constructs were synthesized using solid phase oligonucleotide synthesis methods as described for 19-23 mer siRNAs (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086).

Individual RNA strands were synthesized and HPLC purified according to standard methods (Integrated DNA Technologies, Coralville, Iowa). For example, RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, 1993, *Methods Mol Biol* 20: 81-114; Wincott et al., 1995, *Nucleic Acids Res* 23: 2677-84). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min step-linear gradient. The gradient varied from 90:10 Buffers A:B to 52:48 Buffers A:B, where Buffer A was 100 mM Tris pH 8.5 and Buffer B was 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 µm inner diameter and contains ssDNA 100R Gel (Beckman-Coulter). Typically, about 0.6 nmole of oligonucleotide was injected into a capillary, run in an electric field of 444 V/cm and detected by UV absorbance at 260 nm. Denaturing Tris-Borate-7 M-urea running buffer was purchased from Beckman-Coulter. Oligoribonucleotides were obtained that are at least 90% pure as assessed by CE for use in experiments described below. Compound identity was verified by matrix-assisted laser desorption ionization time-of-flight (MALDI-TOF) mass spectroscopy on a Voyager DE™ Biospectometry Work Station (Applied Biosystems, Foster City, Calif.) following the manufacturer's recommended protocol. Relative molecular masses of all oligomers were obtained, often within 0.2% of expected molecular mass.

Preparation of Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5' in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Nomenclature

For consistency, the following nomenclature has been employed in the instant specification. Names given to duplexes indicate the length of the oligomers and the presence or absence of overhangs. A "25/27" is an asymmetric duplex having a 25 base sense strand and a 27 base antisense strand with a 2-base 3'-overhang. A "27/25" is an asymmetric duplex having a 27 base sense strand and a 25 base antisense strand.

Cell Culture and RNA Transfection

HeLa cells were obtained from ATCC and maintained in Dulbecco's modified Eagle medium (HyClone) supplemented with 10% fetal bovine serum (HyClone) at 37° C. under 5% $CO_2$. For RNA transfections, HeLa cells were transfected with DsiRNAs as indicated at a final concentration of 1 nM or 0.1 nM using Lipofectamine™ RNAiMAX (Invitrogen) and following manufacturer's instructions. Briefly, 2.5 µL of a 0.2 µM or 0.02 µM stock solution of each DsiRNA (or DsiRNA-peptide conjugate) were mixed with 46.5 µL of Opti-MEM I (Invitrogen) and 1 µL of Lipofectamine™ RNAiMAX. The resulting 50 µL mix was added into individual wells of 12 well plates and incubated for 20 min at RT to allow DsiRNA:Lipofectamine™ RNAiMAX complexes to form. Meanwhile, HeLa cells were trypsinized and resuspended in medium at a final concentration of 367 cells/µL. Finally, 450 µL of the cell suspension were added to each well (final volume 500 µL) and plates were placed into the incubator for 24 hours.

Assessment of Inhibition

Target gene knockdown was determined by qRT-PCR, with values normalized to HPRT expression control treatments, including Lipofectamine™ RNAiMAX alone (Vehicle control) or untreated.

RNA Isolation and Analysis

Cells were washed once with 2 mL of PBS, and total RNA was extracted using RNeasy Mini Kit™ (Qiagen) and eluted in a final volume of 3 µL. 1 µg of total RNA was reverse-transcribed using Transcriptor 1$^{st}$ Strand cDNA Kit™ (Roche) and random hexamers following manufacturer's instructions. One-thirtieth (0.66 µL) of the resulting cDNA was mixed with 5 µL of IQ Multiplex Powermix (Bio-Rad) together with 3.33 µL of $H_2O$ and 1 µL of a 3 µM mix containing primers and probes specific for human genes HPRT-1 (accession number NM_000194) and KRAS target sequences.

Quantitative RT-PCR

A CFX96 Real-time System with a C1000 Thermal cycler (Bio-Rad) was used for the amplification reactions. PCR conditions are: 95° C. for 3 min; and then cycling at 95° C., 10 sec; 55° C., 1 min for 40 cycles. Each sample was tested in triplicate. Relative HPRT mRNA levels were normalized to target mRNA levels and compared with mRNA levels obtained in control samples treated with the transfection reagent alone, or untreated. Data was analyzed using Bio-Rad CFX Manager version 1.0 software.

Example 2

Preparation of Charge-Trapped Peptide-dsRNA Conjugates

Oligonucleotide-charge-trapped peptide conjugates of the present invention are synthesized with chemistry based on the conjugation of HyNic (6-Hydrazinonicotinamide)-modified peptides to 4FB (4-Formylbenzamide)-modified oligonucleotides. Other peptide synthesis methods and conjugation procedures known in the art are also applicable.

HyNic moieties are incorporated on a peptide at either N- or C-termini using 6-Boc-HyNic or FMOC-Lys-($\epsilon$-6-BocHyNic)OH, respectively. Cleavage from resin is accomplished using TFA/acetone/water/triisopropylsilane (TIS)/water (92.5/2.5/2.5/2.5) for 2 hours. The presence of the acetone forms a hydrazone with the deprotected hydrazine moiety in situ blocking any trifluoroacetamide formation from the reaction of TFA with the strongly nucleophilic hydrazine. Crude peptides are analyzed by HPLC and ES-MS. Products are isolated by RP-HPLC using a gradient method. For Pegylated peptides, polyethylene glycol synthons are directly added during solid phase peptide synthesis. In some instances, additional polyethylene glycol spacers are also added to the oligonucleotide termini using polyethylene glycol oligonucleotide synthons.

Amino-modified oligonucleotides are converted to 5'-4FB-oligonucleotides. Linking of HyNic-peptides to 4FB-modified oligonucleotides is performed at a 2-5 mole excess of HyNic-peptide and generally produced >80% conjugate yield. Hydrazone bond formation is catalyzed and reaction kinetics improved 10-100-fold via inclusion of aniline, generally leading to conjugation yields >95%. Optimal conjugation kinetics (formation of the hydrazone bond) is achieved between pH 4.5-5.0. However, the reaction also can proceed at higher pH, albeit at a slower rate. The optimum pH for each conjugation is determined empirically, also taking into account the solubility of the different peptide sequences. The degree of conjugation can be monitored spectrophotometrically. Formation of the bis-aryl hydrazone bond is utilized both to trace and to quantify progress of the conjugation reaction, using the known molar extinction coefficient (29,000 @ 354 nm). Diafiltration is used to remove excess peptide, yielding the oligonucleotide-peptide conjugates. To produce HyNic-quenched peptides, HyNic-peptides are reacted with 2-Sulfobenzaldehyde to inactivate the HyNic reactive moiety on the peptide.

Cell-Free Dicing Assay

DsiRNA or peptide-conjugated DsiRNA (final concentration at 5 µM) are incubated with recombinant human dicer enzyme mixture (Genlantis, #T52002) at 37° C. for 2 hrs, and the reaction is stopped with stop solution. This final solution is mixed with gel loading buffer (Bio-Rad, #161-0767). Dicer-cleaved dsRNAs and intact DsiRNAs are resolved by 18% native polyacrylamide gel electrophoresis. Gel images are obtained using the Bio-Rad VersaDoc™ imaging system (model #4000MP).

Serum Stability Assay

DsiRNA or peptide-conjugated DsiRNA (2 µM final concentration) are incubated in 90% (v/v) mouse serum (Sigma #M5905) at 37° C. At different time points (0, 2, 4, 8, 1, 10 & 25 hours), 10 µL sample is mixed with 2 µL $H_2O$ and 3 µL gel loading buffer (Bio-Rad #161-0767) and is immediately flash frozen in an alcohol-dry ice bath. Samples are electrophoresed on an 18% native polyacrylamide gel (Bio-Rad #161-1216). Resolved siRNA bands are quantified using the Bio-Rad VersaDoc™ imaging system (Bio-Rad model #4000MP). The half-life of individual dsRNAs in 90% serum is calculated by plotting the change in dsRNA band intensity over time.

HPRT1- and KRAS-Targeting DsiRNAs

Figure 3:
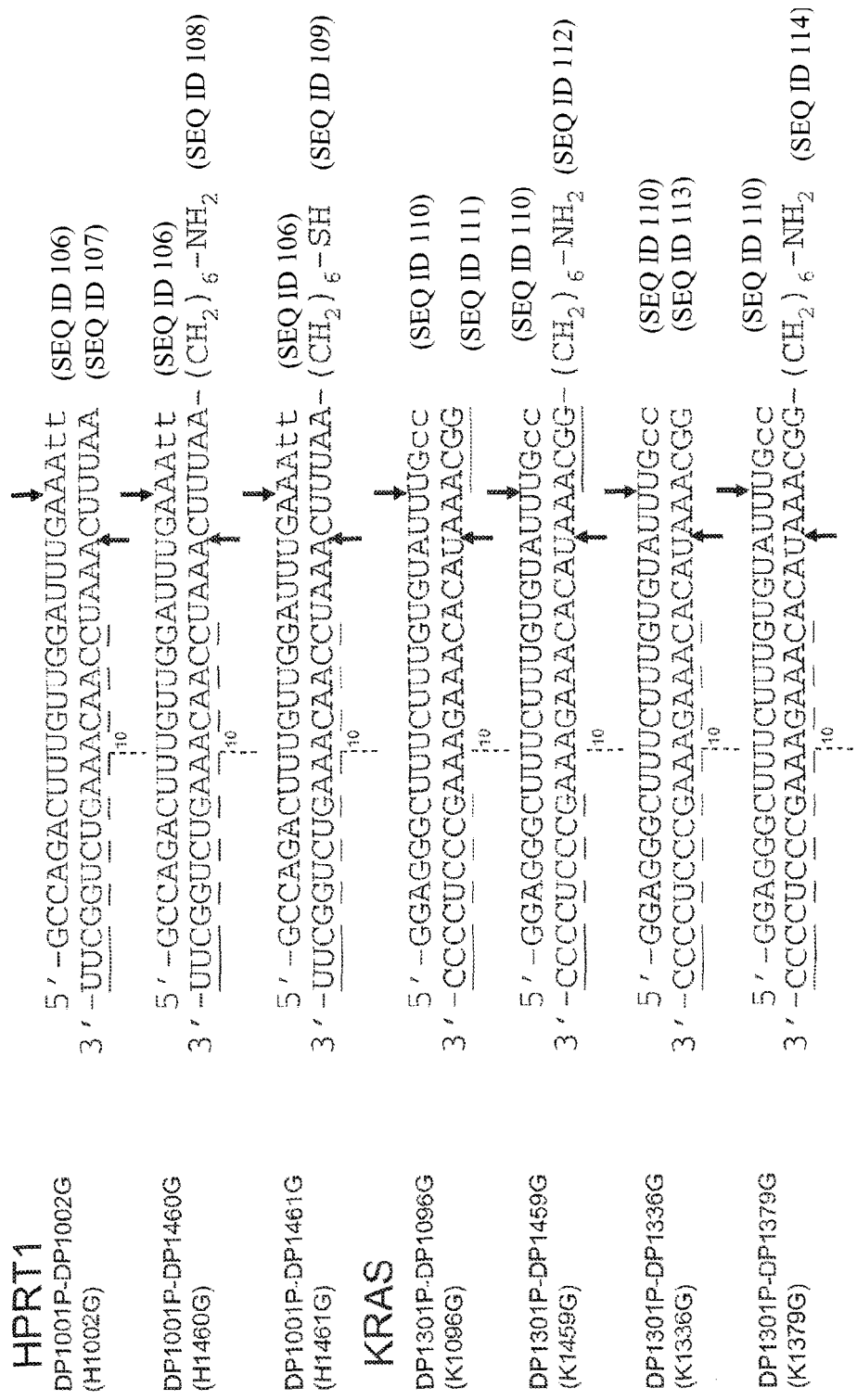
FIG. 3 shows exemplary sequences of HPRT1- and KRAS-targeting dsRNAs of the invention. Underlined residues indicate positions of 2'-O-methyl modifications. Arrows indicate projected sites of dicer enzyme cleavage within the dsRNAs, while dashed lines indicate the projected position of Argonaute2-mediated cleavage within a corresponding target RNA sequence.

Exemplary DsiRNAs directed against HPRT1 and KRAS target genes are synthesized as described herein, with DsiRNAs possessing the oligonucleotide sequences, 2'-O-methyl and end modifications shown in FIG. 3.

Conjugated Phase-Changing Charge-Trapped Peptides

Exemplary phase-changing charge-trapped peptides used or capable of use in conjugation with DsiRNAs in the conjugates of the instant invention are listed above.

As schematically depicted in FIG. 4, conjugation of phase-changing charge-trapped peptides is performed via HyNic (6-Hydrazinonicotinamide) at the 5'-terminal residue of guide strands of KRAS-targeting DsiRNAs. Successful synthesis of various peptide-DsiRNA conjugates is confirmed via observation of the increased size (and, therefore, retarded electrophoretic mobility) associated with a successful conjugation.

Example 3

Transfected dsRNA-Charge-Trapped Peptide Conjugates Reduced Expression of Target Gene Levels in a Cell Cell Culture and RNA Transfection HeLa cells are obtained from ATCC and maintained in Dulbecco's modified Eagle medium (HyClone) supplemented with 10% fetal bovine serum (HyClone) at 37° C. under 5% $CO_2$. For dsRNA and dsRNA-phase changing peptide conjugate transfections, HeLa cells are transfected with the unconjugated or conjugated DsiRNAs at indicated final concentrations (e.g., 1 nM or 0.1 nM) in the presence of Lipofectamine™ RNAiMAX (Invitrogen). In certain examples, unconjugated DsiRNAs are also used as positive controls. In certain examples, 2.5 µL of a 0.2 µM or 0.02 µM stock solution of each DsiRNA is mixed with 47.5 µL of Opti-MEM I (Invitrogen). For Lipofectamine™ controls, 2.5 µL of a 0.2 µM or 0.02 µM stock solution of each DsiRNA is mixed with 46.54, of Opti-MEM I (Invitrogen) and 1 µL of Lipofectamine™ RNAiMAX. The resulting 50 µL mix is added into individual wells of 12 well plates and incubated for 20 minutes at room temperature to allow DsiRNA:Lipofectamine™ RNAiMAX complexes to form. Meanwhile, HeLa cells are trypsinized and resuspended in medium at a final concentration of about 367 cells/pt. Finally, 45 µL of the cell suspension is added to each well (final volume 500 µL) and plates are placed into the incubator for 24 hours. For dose-response studies, the concentrations of transfected DsiRNAs are varied from initially 1 pM to 1 nM. For dose-response studies involving DsiRNA-peptide conjugates administered to cells in the absence of transfection vehicle, the concentrations of administered DsiRNAs and DsiRNA-peptide conjugates are varied from approximately 5 nM to approximately 5 µM. Time course studies can also be performed, with incubation times of about 4 hours to about 72 hours studied.

Assessment of Inhibition

Target gene knockdown is determined by qRT-PCR, with values normalized to HPRT expression control treatments ("Cell Only" control).

RNA Isolation and Analysis

Cells are washed once with 2 mL of PBS, and total RNA is extracted using RNeasy Mini Kit™ (Qiagen) and eluted in a final volume of 30 µL. 1 µg of total RNA is reverse-transcribed using Transcriptor $1^{st}$ Strand cDNA Kit™ (Roche) and random hexamers following manufacturer's instructions. One-thirtieth (0.66 µL) of the resulting cDNA is mixed with 5 µL of IQ Multiplex Powermix (Bio-Rad) together with 3.33 µL of $H_2O$ and 1 µL of a 3 µM mix containing primers and probes specific for human genes HPRT-1 (accession number NM_000194) and KRAS target sequences.

Quantitative RT-PCR

A CFX96 Real-time System with a C1000 Thermal cycler (Bio-Rad) is used for the amplification reactions. PCR conditions are: 95° C. for 3 min; and then cycling at 95° C., 10 sec; 55° C., 1 min for 40 cycles. Each sample is tested in duplicate (with duplicate experiments performed for each agent). Relative HPRT mRNA levels are normalized to target mRNA levels and compared with mRNA levels obtained in control samples treated with the transfection reagent alone, or untreated. Data are analyzed using Bio-Rad CFX Manager version 1.0 software. Expression data are presented as a comparison of the expression under the treatment of an unconjugated dsRNA or that of dsRNA-phase changing peptide conjugates, versus that of a "Cell Only" control.

Exemplary DsiRNA-peptide conjugates are examined for the ability to inhibit target KRAS mRNA levels in a cell when administered via transfection.

Example 4

Use of dsRNA-Peptide Conjugate Formulation to Reduce Expression of a Target Gene in a Subcutaneous Animal Tumor Model In order to assess the efficiency of delivery and subsequent functionality of the dsRNAs, dsRNA and peptide and dsRNA-peptide conjugate formulations, subcutaneous (s.c.) tumor models (Judge et al., J Clin Invest. 2009; 119(3):661-73) are utilized. Hep3B tumors are established in female SCID/beige mice by s.c. injection of $3\times10^6$ cells in 50 µL PBS into the left-hind flank. Mice are randomized into treatment groups 10-17 days after seeding as tumors became palpable. Formulations of dsRNA, peptide and dsRNA-peptide conjugates or vehicle control is administered by standard intravenous (i.v.) injection via the lateral tail vein, calculated based on a mg dsRNAs/kg body weight basis according to individual animal weights. Tumors are measured in 2 dimensions (width×length) to assess tumor growth using digital calipers. Tumor volume is calculated using the equation $x*y*y/2$, where x=largest diameter and y=smallest diameter, and is expressed as group mean±SD. Tumor tissues are also removed from the animals of different treatment groups and gene knockdown is confirmed. Tumor volume, survival and RNA expression data are presented as a comparison between the treatments of dsRNA versus dsRNA and peptide and dsRNA-peptide conjugate formulations.

Example 5

Use of a dsRNA-Peptide Conjugate to Reduce Expression of a Target Gene in an Orthotopic Animal Tumor Model In order to assess the efficiency of targeting and subsequent functionality of the dsRNAs, dsRNA and peptide and dsRNA-charge-trapped peptide conjugate formulations, intrahepatic tumor models (Judge et al., J Clin Invest. 2009; 119(3):661-73) are utilized. Liver tumors are established in mice by direct intrahepatic injection of Hep3B or Neuro2a tumor cells. Female SCID/beige mice and male A/J mice are used as hosts for the Hep3B and Neuro2a tumors, respectively. Maintaining the mice under gas anesthesia, a single 1.5-cm incision across the midline is made below the sternum, and the left lateral hepatic lobe is exteriorized. $1 \times 10^6$ Hep3B cells or $1 \times 10^5$ Neuro2a cells suspended in 25 μL PBS are injected slowly into the lobe at a shallow angle using a Hamilton syringe and a 30-gauge needle. A swab is then applied to the puncture wound to stop any bleeding prior to suturing. Mice are allowed to recover from anesthesia in a sterile cage and monitored closely for 2-4 hours before being returned to conventional housing. Eight to eleven days after tumor implantation, mice are randomized into treatment groups: dsRNA, dsRNA and peptide and dsRNA-peptide conjugate formulations or vehicle control is administered by standard intravenous (i.v.) injection via the lateral tail vein, calculated based on a mg dsRNAs/kg body weight basis according to individual animal weights. Body weights are monitored throughout the duration of the study as an indicator of developing tumor burden and treatment tolerability. For efficacy studies, defined humane end points are determined as a surrogate for survival. Assessments are made based on a combination of clinical signs, weight loss, and abdominal distension to define the day of euthanization due to tumor burden. Tumor tissues are removed from the animals of different treatment groups and gene knockdown is confirmed.

Functionality of dsRNA, dsRNA and charge-trapped peptide and dsRNA-charge-trapped peptide conjugate formulations for tumor cell uptake are also tested by labeling the peptide and/or dsRNA with fluorescent tags and performing fluorescent biodistribution studies using a live-animal imaging system (Xenogen or BioRad) (Eguchi et al., Nat Biotechnol. 2009; 27(6):567-71). Using this methodology, and by comparing with dsRNA formulation alone the ability of the charge-trapped peptide to facilitate tumor cell internalization for both the dsRNA and peptide and dsRNA-charge-trapped peptide conjugate formulations is confirmed. By contrast, dsRNA formulation alone, used as a control in this study, is unable to be taken up and delivered to the same extent to tumor surface. Efficacy end points, RNA expression and biodistribution data are presented as a comparison between the treatments of dsRNA versus dsRNA and charge-trapped peptide and dsRNA-charge-trapped peptide conjugate formulations.

REFERENCES

1. Castanotto and Rossi, Nature 2009; 457: 426-433.
2. Lehninger Principles of Biochemistry, 3rd Ed., 2000. Edited by David L. Nelson and Michael M. Cox, Worth Publishers, New York, N.Y.
3. Moschos et al., Bioconjug Chem. 2007; 18(5):1450-1459.
4. Nishina et al., Mol Ther. 2008; 16(4):734-40).
5. Lu, Langer and Chen. Mol Pharm. 2009; 6(3):763-71.
6. McNaughton et al., Proc Natl Acad Sci USA. 2009 Apr. 14; 106(15):6111-6116.
7. Judge et al., J. Clin. Invest. 2009; 119(3):661-673.
8. Eguchi et al., Nat Biotechnol. 2009; 27(6):567-71.
9. Abrams et al., Mol Ther. 2009 Sep. 8. [Epub ahead of print].
10. Ko et al., J Control Release. 2009 Jan. 19; 133(2): 132-8.
11. Noble et al., Cancer Chemother Pharmacol. 2009; 64(4):741-51.
12. Mangala et al., Methods Mol Biol. 2009; 555:29-42.
13. van Rossenberg et al., J Biol Chem. 2002; 277(48): 45803-10.

We claim:

1. A method for reducing expression of a target gene in a cell of a subject, comprising:
   contacting said cell with a formulation comprising a DsiRNA and a phase changing peptide, wherein said peptide comprises an amino acid sequence selected from the group consisting of SEQ ID NOs.: 1-50, in an amount effective to reduce expression of said target gene in said cell in comparison to a reference dsRNA.

2. The method of claim 1, wherein said DsiRNA is a DsiRNA of 25-30 nucleotides.

3. The method of claim 1, wherein said DsiRNA is a DsiRNA of 30-70 nucleotides.

4. The method of claim 1, wherein said formulation is selected from the group consisting of a lipid formulation and a polymer formulation.

5. The method of claim 1, wherein said formulation is selected from the group consisting of a vesicle based formulation and a micelle based formulation.

6. The method of claim 1, wherein said formulation comprises free DsiRNA in solution.

7. The method of claim 1, wherein said peptide further comprises a linker comprising one or more amino acids.

8. The method of claim 7, wherein said linker comprises a cysteine residue.

9. The method of claim 7, wherein said linker comprises a structure selected from the group consisting of a Citruline-Valine (Cit-Val) structure, a Valine-Citruline (Val-Cit) structure, and a repeat thereof.

10. The method of claim 7, wherein said linker is attached to said DsiRNA.

11. The method of claim 10, wherein said peptide further comprises spacer amino acids.

12. The method of claim 11, wherein said spacer amino acids comprise Glycine and/or Serine.

13. The method of claim 1, wherein said formulation further comprises PEG.

14. The method of claim 1, wherein said peptide is attached to PEG.

15. The method of claim 1, wherein said peptide is conjugated to said DsiRNA.

16. The method of claim 15, wherein said conjugated peptide is in the aqueous phase of the formulation.

17. The method of claim 15, wherein said conjugated peptide is in the lipid or polymer phase of the formulation.

18. The method of claim 1, wherein said formulation is a lipid nanoparticle.

* * * * *

SEQUENCE LISTING

```
<160> NUMBER OF SEQ ID NOS: 114

<210> SEQ ID NO 1
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (3)..(7)
<223> OTHER INFORMATION: This region may encompass 0 to 5 residues
<220> FEATURE:
<221> NAME/KEY: misc_feature
<222> LOCATION: (9)..(13)
<223> OTHER INFORMATION: This region may encompass 0 to 5 residues
<220> FEATURE:
<221> NAME/KEY: misc_feature
<222> LOCATION: (3)..(13)
<223> OTHER INFORMATION: This region may or may not be present in its
      entirety
<220> FEATURE:
<221> NAME/KEY: misc_feature
<222> LOCATION: (14)..(18)
<223> OTHER INFORMATION: This region may encompass 0 to 5 residues
<220> FEATURE:
<221> NAME/KEY: misc_feature
<222> LOCATION: (20)..(24)
<223> OTHER INFORMATION: This region may encompass 0 to 5 residues
<220> FEATURE:
```

```
<221> NAME/KEY: misc_feature
<222> LOCATION: (14)..(24)
<223> OTHER INFORMATION: This region may or may not be present in its
      entirety
<220> FEATURE:
<221> NAME/KEY: misc_feature
<222> LOCATION: (25)..(29)
<223> OTHER INFORMATION: This region may encompass 0 to 5 residues
<220> FEATURE:
<221> NAME/KEY: misc_feature
<222> LOCATION: (31)..(35)
<223> OTHER INFORMATION: This region may encompass 0 to 5 residues
<220> FEATURE:
<221> NAME/KEY: misc_feature
<222> LOCATION: (25)..(35)
<223> OTHER INFORMATION: This region may or may not be present in its
      entirety
<220> FEATURE:
<221> NAME/KEY: misc_feature
<222> LOCATION: (36)..(40)
<223> OTHER INFORMATION: This region may encompass 0 to 5 residues
<220> FEATURE:
<221> NAME/KEY: misc_feature
<222> LOCATION: (42)..(46)
<223> OTHER INFORMATION: This region may encompass 0 to 5 residues
<220> FEATURE:
<221> NAME/KEY: misc_feature
<222> LOCATION: (36)..(46)
<223> OTHER INFORMATION: This region may or may not be present in its
      entirety
<220> FEATURE:
<221> NAME/KEY: misc_feature
<222> LOCATION: (47)..(51)
<223> OTHER INFORMATION: This region may encompass 0 to 5 residues
<220> FEATURE:
<221> NAME/KEY: misc_feature
<222> LOCATION: (53)..(57)
<223> OTHER INFORMATION: This region may encompass 0 to 5 residues
<220> FEATURE:
<221> NAME/KEY: misc_feature
<222> LOCATION: (47)..(57)
<223> OTHER INFORMATION: This region may or may not be present in its
      entirety
<220> FEATURE:
<221> NAME/KEY: misc_feature
<222> LOCATION: (58)..(62)
<223> OTHER INFORMATION: This region may encompass 0 to 5 residues
<220> FEATURE:
<221> NAME/KEY: misc_feature
<222> LOCATION: (64)..(68)
<223> OTHER INFORMATION: This region may encompass 0 to 5 residues
<220> FEATURE:
<221> NAME/KEY: DISULFID
<222> LOCATION: (1)..(69)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 1

Cys Lys Lys Lys Lys Lys Lys His Lys Lys Lys Lys Lys Lys Lys
1               5                   10                  15

Lys Lys His Lys Lys Lys Lys Lys Lys Lys Lys Lys His Lys Lys
                20                  25                  30

Lys Lys Lys Lys Lys Lys Lys His Lys Lys Lys Lys Lys Lys Lys
            35                  40                  45

Lys Lys Lys His Lys Lys Lys Lys Lys Lys Lys Lys Lys His Lys
        50                  55                  60

Lys Lys Lys Lys Cys
65

<210> SEQ ID NO 2
<211> LENGTH: 69
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (3)..(7)
<223> OTHER INFORMATION: This region may encompass 0 to 5 residues
<220> FEATURE:
<221> NAME/KEY: misc_feature
<222> LOCATION: (9)..(13)
<223> OTHER INFORMATION: This region may encompass 0 to 5 residues
<220> FEATURE:
<221> NAME/KEY: misc_feature
<222> LOCATION: (3)..(13)
<223> OTHER INFORMATION: This region may or may not be present in its
      entirety
<220> FEATURE:
<221> NAME/KEY: misc_feature
<222> LOCATION: (14)..(18)
<223> OTHER INFORMATION: This region may encompass 0 to 5 residues
<220> FEATURE:
<221> NAME/KEY: misc_feature
<222> LOCATION: (20)..(24)
<223> OTHER INFORMATION: This region may encompass 0 to 5 residues
<220> FEATURE:
<221> NAME/KEY: misc_feature
<222> LOCATION: (14)..(24)
<223> OTHER INFORMATION: This region may or may not be present in its
      entirety
<220> FEATURE:
<221> NAME/KEY: misc_feature
<222> LOCATION: (25)..(29)
<223> OTHER INFORMATION: This region may encompass 0 to 5 residues
<220> FEATURE:
<221> NAME/KEY: misc_feature
<222> LOCATION: (31)..(35)
<223> OTHER INFORMATION: This region may encompass 0 to 5 residues
<220> FEATURE:
<221> NAME/KEY: misc_feature
<222> LOCATION: (25)..(35)
<223> OTHER INFORMATION: This region may or may not be present in its
      entirety
<220> FEATURE:
<221> NAME/KEY: misc_feature
<222> LOCATION: (36)..(40)
<223> OTHER INFORMATION: This region may encompass 0 to 5 residues
<220> FEATURE:
<221> NAME/KEY: misc_feature
<222> LOCATION: (42)..(46)
<223> OTHER INFORMATION: This region may encompass 0 to 5 residues
<220> FEATURE:
<221> NAME/KEY: misc_feature
<222> LOCATION: (36)..(46)
<223> OTHER INFORMATION: This region may or may not be present in its
      entirety
<220> FEATURE:
<221> NAME/KEY: misc_feature
<222> LOCATION: (47)..(51)
<223> OTHER INFORMATION: This region may encompass 0 to 5 residues
<220> FEATURE:
<221> NAME/KEY: misc_feature
<222> LOCATION: (53)..(57)
<223> OTHER INFORMATION: This region may encompass 0 to 5 residues
<220> FEATURE:
<221> NAME/KEY: misc_feature
<222> LOCATION: (47)..(57)
<223> OTHER INFORMATION: This region may or may not be present in its
      entirety
<220> FEATURE:
<221> NAME/KEY: misc_feature
<222> LOCATION: (58)..(62)
<223> OTHER INFORMATION: This region may encompass 0 to 5 residues
<220> FEATURE:
<221> NAME/KEY: misc_feature
<222> LOCATION: (64)..(68)
<223> OTHER INFORMATION: This region may encompass 0 to 5 residues
<220> FEATURE:
```

```
<221> NAME/KEY: DISULFID
<222> LOCATION: (1)..(69)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 2

Cys Arg Arg Arg Arg Arg His Arg Arg Arg Arg Arg Arg Arg Arg
1               5                   10                  15

Arg Arg His Arg Arg Arg Arg Arg Arg Arg Arg Arg His Arg Arg
            20                  25                  30

Arg Arg Arg Arg Arg Arg Arg His Arg Arg Arg Arg Arg Arg Arg
        35                  40                  45

Arg Arg Arg His Arg Arg Arg Arg Arg Arg Arg Arg Arg His Arg
    50                  55                  60

Arg Arg Arg Arg Cys
65

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(6)
<223> OTHER INFORMATION: This region may encompass 0 to 5 residues
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: misc_feature
<222> LOCATION: (2)..(12)
<223> OTHER INFORMATION: This region may or may not be present in its
      entirety
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: misc_feature
<222> LOCATION: (19)..(23)
<223> OTHER INFORMATION: This region may encompass 0 to 5 residues
<220> FEATURE:
<221> NAME/KEY: misc_feature
<222> LOCATION: (13)..(23)
<223> OTHER INFORMATION: This region may or may not be present in its
      entirety
<220> FEATURE:
<221> NAME/KEY: misc_feature
<222> LOCATION: (24)..(28)
<223> OTHER INFORMATION: This region may encompass 0 to 5 residues
<220> FEATURE:
<221> NAME/KEY: misc_feature
<222> LOCATION: (30)..(34)
<223> OTHER INFORMATION: This region may encompass 0 to 5 residues
<220> FEATURE:
<221> NAME/KEY: misc_feature
<222> LOCATION: (24)..(34)
<223> OTHER INFORMATION: This region may or may not be present in its
      entirety
<220> FEATURE:
<221> NAME/KEY: misc_feature
<222> LOCATION: (35)..(39)
<223> OTHER INFORMATION: This region may encompass 0 to 5 residues
<220> FEATURE:
<221> NAME/KEY: misc_feature
<222> LOCATION: (41)..(45)
<223> OTHER INFORMATION: This region may encompass 0 to 5 residues
```

```
<220> FEATURE:
<221> NAME/KEY: misc_feature
<222> LOCATION: (35)..(45)
<223> OTHER INFORMATION: This region may or may not be present in its
      entirety
<220> FEATURE:
<221> NAME/KEY: misc_feature
<222> LOCATION: (46)..(50)
<223> OTHER INFORMATION: This region may encompass 0 to 5 residues
<220> FEATURE:
<221> NAME/KEY: misc_feature
<222> LOCATION: (52)..(56)
<223> OTHER INFORMATION: This region may encompass 0 to 5 residues
<220> FEATURE:
<221> NAME/KEY: misc_feature
<222> LOCATION: (46)..(56)
<223> OTHER INFORMATION: This region may or may not be present in its
      entirety
<220> FEATURE:
<221> NAME/KEY: misc_feature
<222> LOCATION: (57)..(61)
<223> OTHER INFORMATION: This region may encompass 0 to 5 residues
<220> FEATURE:
<221> NAME/KEY: misc_feature
<222> LOCATION: (63)..(67)
<223> OTHER INFORMATION: This region may encompass 0 to 5 residues
<220> FEATURE:
<221> NAME/KEY: misc_feature
<222> LOCATION: (57)..(67)
<223> OTHER INFORMATION: This region may or may not be present in its
      entirety
<220> FEATURE:
<221> NAME/KEY: misc_feature
<222> LOCATION: (68)..(72)
<223> OTHER INFORMATION: This region may encompass 0 to 5 residues
<220> FEATURE:
<221> NAME/KEY: misc_feature
<222> LOCATION: (74)..(78)
<223> OTHER INFORMATION: This region may encompass 0 to 5 residues
<220> FEATURE:
<221> NAME/KEY: misc_feature
<222> LOCATION: (68)..(78)
<223> OTHER INFORMATION: This region may or may not be present in its
      entirety
<220> FEATURE:
<221> NAME/KEY: misc_feature
<222> LOCATION: (79)..(83)
<223> OTHER INFORMATION: This region may encompass 0 to 5 residues
<220> FEATURE:
<221> NAME/KEY: misc_feature
<222> LOCATION: (85)..(89)
<223> OTHER INFORMATION: This region may encompass 0 to 5 residues
<220> FEATURE:
<221> NAME/KEY: misc_feature
<222> LOCATION: (79)..(89)
<223> OTHER INFORMATION: This region may or may not be present in its
      entirety
<220> FEATURE:
<221> NAME/KEY: misc_feature
<222> LOCATION: (90)..(94)
<223> OTHER INFORMATION: This region may encompass 0 to 5 residues
<220> FEATURE:
<221> NAME/KEY: misc_feature
<222> LOCATION: (96)..(100)
<223> OTHER INFORMATION: This region may encompass 0 to 5 residues
<220> FEATURE:
<221> NAME/KEY: misc_feature
<222> LOCATION: (90)..(100)
<223> OTHER INFORMATION: This region may or may not be present in its
      entirety
<220> FEATURE:
<221> NAME/KEY: misc_feature
<222> LOCATION: (101)..(105)
<223> OTHER INFORMATION: This region may encompass 0 to 5 residues
<220> FEATURE:
<221> NAME/KEY: misc_feature
<222> LOCATION: (107)..(111)
<223> OTHER INFORMATION: This region may encompass 0 to 5 residues
<220> FEATURE:
```

```
<221> NAME/KEY: misc_feature
<222> LOCATION: (101)..(111)
<223> OTHER INFORMATION: This region may or may not be present in its
      entirety
<220> FEATURE:
<221> NAME/KEY: DISULFID
<222> LOCATION: (1)..(112)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 3

Cys Lys Lys Lys Lys Lys His Lys Lys Lys Lys Lys Lys Lys Lys
1               5                   10                  15

Lys His Lys Lys Lys Lys Lys Lys Lys Lys Lys His Lys Lys Lys
        20                  25                  30

Lys Lys Lys Lys Lys Lys Lys His Lys Lys Lys Lys Lys Lys Lys
        35                  40                  45

Lys Lys His Lys Lys Lys Lys Lys Lys Lys Lys Lys His Lys Lys
        50                  55                  60

Lys Lys Lys Lys Lys Lys Lys His Lys Lys Lys Lys Lys Lys Lys
65              70                  75                  80

Lys Lys Lys His Lys Lys Lys Lys Lys Lys Lys Lys Lys His Lys
            85                  90                  95

Lys Lys Lys Lys Lys Lys Lys Lys His Lys Lys Lys Lys Lys Cys
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(6)
<223> OTHER INFORMATION: This region may encompass 0 to 5 residues
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: misc_feature
<222> LOCATION: (2)..(12)
<223> OTHER INFORMATION: This region may or may not be present in its
      entirety
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: misc_feature
<222> LOCATION: (19)..(23)
<223> OTHER INFORMATION: This region may encompass 0 to 5 residues
<220> FEATURE:
<221> NAME/KEY: misc_feature
<222> LOCATION: (13)..(23)
<223> OTHER INFORMATION: This region may or may not be present in its
      entirety
<220> FEATURE:
<221> NAME/KEY: misc_feature
<222> LOCATION: (24)..(28)
<223> OTHER INFORMATION: This region may encompass 0 to 5 residues
<220> FEATURE:
<221> NAME/KEY: misc_feature
<222> LOCATION: (30)..(34)
<223> OTHER INFORMATION: This region may encompass 0 to 5 residues
<220> FEATURE:
<221> NAME/KEY: misc_feature
```

```
<222> LOCATION: (24)..(34)
<223> OTHER INFORMATION: This region may or may not be present in its
      entirety
<220> FEATURE:
<221> NAME/KEY: misc_feature
<222> LOCATION: (35)..(39)
<223> OTHER INFORMATION: This region may encompass 0 to 5 residues
<220> FEATURE:
<221> NAME/KEY: misc_feature
<222> LOCATION: (41)..(45)
<223> OTHER INFORMATION: This region may encompass 0 to 5 residues
<220> FEATURE:
<221> NAME/KEY: misc_feature
<222> LOCATION: (35)..(45)
<223> OTHER INFORMATION: This region may or may not be present in its
      entirety
<220> FEATURE:
<221> NAME/KEY: misc_feature
<222> LOCATION: (46)..(50)
<223> OTHER INFORMATION: This region may encompass 0 to 5 residues
<220> FEATURE:
<221> NAME/KEY: misc_feature
<222> LOCATION: (52)..(56)
<223> OTHER INFORMATION: This region may encompass 0 to 5 residues
<220> FEATURE:
<221> NAME/KEY: misc_feature
<222> LOCATION: (46)..(56)
<223> OTHER INFORMATION: This region may or may not be present in its
      entirety
<220> FEATURE:
<221> NAME/KEY: misc_feature
<222> LOCATION: (57)..(61)
<223> OTHER INFORMATION: This region may encompass 0 to 5 residues
<220> FEATURE:
<221> NAME/KEY: misc_feature
<222> LOCATION: (63)..(67)
<223> OTHER INFORMATION: This region may encompass 0 to 5 residues
<220> FEATURE:
<221> NAME/KEY: misc_feature
<222> LOCATION: (57)..(67)
<223> OTHER INFORMATION: This region may or may not be present in its
      entirety
<220> FEATURE:
<221> NAME/KEY: misc_feature
<222> LOCATION: (68)..(72)
<223> OTHER INFORMATION: This region may encompass 0 to 5 residues
<220> FEATURE:
<221> NAME/KEY: misc_feature
<222> LOCATION: (74)..(78)
<223> OTHER INFORMATION: This region may encompass 0 to 5 residues
<220> FEATURE:
<221> NAME/KEY: misc_feature
<222> LOCATION: (68)..(78)
<223> OTHER INFORMATION: This region may or may not be present in its
      entirety
<220> FEATURE:
<221> NAME/KEY: misc_feature
<222> LOCATION: (79)..(83)
<223> OTHER INFORMATION: This region may encompass 0 to 5 residues
<220> FEATURE:
<221> NAME/KEY: misc_feature
<222> LOCATION: (85)..(89)
<223> OTHER INFORMATION: This region may encompass 0 to 5 residues
<220> FEATURE:
<221> NAME/KEY: misc_feature
<222> LOCATION: (79)..(89)
<223> OTHER INFORMATION: This region may or may not be present in its
      entirety
<220> FEATURE:
<221> NAME/KEY: misc_feature
<222> LOCATION: (90)..(94)
<223> OTHER INFORMATION: This region may encompass 0 to 5 residues
<220> FEATURE:
<221> NAME/KEY: misc_feature
<222> LOCATION: (96)..(100)
<223> OTHER INFORMATION: This region may encompass 0 to 5 residues
<220> FEATURE:
<221> NAME/KEY: misc_feature
<222> LOCATION: (90)..(100)
```

<223> OTHER INFORMATION: This region may or may not be present in its
      entirety
<220> FEATURE:
<221> NAME/KEY: misc_feature
<222> LOCATION: (101)..(105)
<223> OTHER INFORMATION: This region may encompass 0 to 5 residues
<220> FEATURE:
<221> NAME/KEY: misc_feature
<222> LOCATION: (107)..(111)
<223> OTHER INFORMATION: This region may encompass 0 to 5 residues
<220> FEATURE:
<221> NAME/KEY: misc_feature
<222> LOCATION: (101)..(111)
<223> OTHER INFORMATION: This region may or may not be present in its
      entirety
<220> FEATURE:
<221> NAME/KEY: DISULFID
<222> LOCATION: (1)..(112)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 4

Cys Arg Arg Arg Arg His Arg Arg Arg Arg Arg Arg Arg Arg Arg
1               5                   10                  15

Arg His Arg Arg Arg Arg Arg Arg Arg Arg Arg Arg His Arg Arg Arg
            20                  25                  30

Arg Arg Arg Arg Arg Arg Arg His Arg Arg Arg Arg Arg Arg Arg
        35                  40                  45

Arg His Arg Arg Arg Arg Arg Arg Arg Arg Arg Arg His Arg Arg
    50                  55                  60

Arg Arg Arg Arg Arg Arg Arg His Arg Arg Arg Arg Arg Arg Arg
65                  70                  75                  80

Arg Arg Arg His Arg Arg Arg Arg Arg Arg Arg Arg Arg His Arg
                85                  90                  95

Arg Arg Arg Arg Arg Arg Arg Arg Arg His Arg Arg Arg Arg Arg Cys
                100                 105                 110

<210> SEQ ID NO 5
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(6)
<223> OTHER INFORMATION: This region may encompass 0 to 5 residues
<220> FEATURE:
<221> NAME/KEY: MOD_RES
<222> LOCATION: (7)..(7)
<223> OTHER INFORMATION: Any amino acid except Lys
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: MOD_RES
<222> LOCATION: (13)..(13)
<223> OTHER INFORMATION: Any amino acid except Lys
<220> FEATURE:
<221> NAME/KEY: misc_feature
<222> LOCATION: (14)..(18)
<223> OTHER INFORMATION: This region may encompass 0 to 5 residues
<220> FEATURE:
<221> NAME/KEY: MOD_RES
<222> LOCATION: (19)..(19)
<223> OTHER INFORMATION: Any amino acid except Lys
<220> FEATURE:

```
<221> NAME/KEY: misc_feature
<222> LOCATION: (2)..(19)
<223> OTHER INFORMATION: This region may or may not be present in its
      entirety
<220> FEATURE:
<221> NAME/KEY: misc_feature
<222> LOCATION: (20)..(24)
<223> OTHER INFORMATION: This region may encompass 0 to 5 residues
<220> FEATURE:
<221> NAME/KEY: MOD_RES
<222> LOCATION: (25)..(25)
<223> OTHER INFORMATION: Any amino acid except Lys
<220> FEATURE:
<221> NAME/KEY: misc_feature
<222> LOCATION: (26)..(30)
<223> OTHER INFORMATION: This region may encompass 0 to 5 residues
<220> FEATURE:
<221> NAME/KEY: MOD_RES
<222> LOCATION: (31)..(31)
<223> OTHER INFORMATION: Any amino acid except Lys
<220> FEATURE:
<221> NAME/KEY: misc_feature
<222> LOCATION: (32)..(36)
<223> OTHER INFORMATION: This region may encompass 0 to 5 residues
<220> FEATURE:
<221> NAME/KEY: MOD_RES
<222> LOCATION: (37)..(37)
<223> OTHER INFORMATION: Any amino acid except Lys
<220> FEATURE:
<221> NAME/KEY: misc_feature
<222> LOCATION: (20)..(37)
<223> OTHER INFORMATION: This region may or may not be present in its
      entirety
<220> FEATURE:
<221> NAME/KEY: misc_feature
<222> LOCATION: (38)..(42)
<223> OTHER INFORMATION: This region may encompass 0 to 5 residues
<220> FEATURE:
<221> NAME/KEY: MOD_RES
<222> LOCATION: (43)..(43)
<223> OTHER INFORMATION: Any amino acid except Lys
<220> FEATURE:
<221> NAME/KEY: misc_feature
<222> LOCATION: (44)..(48)
<223> OTHER INFORMATION: This region may encompass 0 to 5 residues
<220> FEATURE:
<221> NAME/KEY: MOD_RES
<222> LOCATION: (49)..(49)
<223> OTHER INFORMATION: Any amino acid except Lys
<220> FEATURE:
<221> NAME/KEY: misc_feature
<222> LOCATION: (50)..(54)
<223> OTHER INFORMATION: This region may encompass 0 to 5 residues
<220> FEATURE:
<221> NAME/KEY: MOD_RES
<222> LOCATION: (55)..(55)
<223> OTHER INFORMATION: Any amino acid except Lys
<220> FEATURE:
<221> NAME/KEY: misc_feature
<222> LOCATION: (38)..(55)
<223> OTHER INFORMATION: This region may or may not be present in its
      entirety
<220> FEATURE:
<221> NAME/KEY: misc_feature
<222> LOCATION: (56)..(60)
<223> OTHER INFORMATION: This region may encompass 0 to 5 residues
<220> FEATURE:
<221> NAME/KEY: MOD_RES
<222> LOCATION: (61)..(61)
<223> OTHER INFORMATION: Any amino acid except Lys
<220> FEATURE:
<221> NAME/KEY: misc_feature
<222> LOCATION: (62)..(66)
<223> OTHER INFORMATION: This region may encompass 0 to 5 residues
<220> FEATURE:
<221> NAME/KEY: MOD_RES
<222> LOCATION: (67)..(67)
<223> OTHER INFORMATION: Any amino acid except Lys
<220> FEATURE:
```

<221> NAME/KEY: misc_feature
<222> LOCATION: (68)..(72)
<223> OTHER INFORMATION: This region may encompass 0 to 5 residues
<220> FEATURE:
<221> NAME/KEY: MOD_RES
<222> LOCATION: (73)..(73)
<223> OTHER INFORMATION: Any amino acid except Lys
<220> FEATURE:
<221> NAME/KEY: misc_feature
<222> LOCATION: (56)..(73)
<223> OTHER INFORMATION: This region may or may not be present in its
      entirety
<220> FEATURE:
<221> NAME/KEY: misc_feature
<222> LOCATION: (74)..(78)
<223> OTHER INFORMATION: This region may encompass 0 to 5 residues
<220> FEATURE:
<221> NAME/KEY: MOD_RES
<222> LOCATION: (79)..(79)
<223> OTHER INFORMATION: Any amino acid except Lys
<220> FEATURE:
<221> NAME/KEY: misc_feature
<222> LOCATION: (80)..(84)
<223> OTHER INFORMATION: This region may encompass 0 to 5 residues
<220> FEATURE:
<221> NAME/KEY: MOD_RES
<222> LOCATION: (85)..(85)
<223> OTHER INFORMATION: Any amino acid except Lys
<220> FEATURE:
<221> NAME/KEY: misc_feature
<222> LOCATION: (86)..(90)
<223> OTHER INFORMATION: This region may encompass 0 to 5 residues
<220> FEATURE:
<221> NAME/KEY: MOD_RES
<222> LOCATION: (91)..(91)
<223> OTHER INFORMATION: Any amino acid except Lys
<220> FEATURE:
<221> NAME/KEY: misc_feature
<222> LOCATION: (74)..(91)
<223> OTHER INFORMATION: This region may or may not be present in its
      entirety
<220> FEATURE:
<221> NAME/KEY: DISULFID
<222> LOCATION: (1)..(92)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 5

Cys Lys Lys Lys Lys Lys Xaa Lys Lys Lys Lys Xaa Lys Lys Lys
1               5                   10                  15

Lys Lys Xaa Lys Lys Lys Lys Xaa Lys Lys Lys Lys Xaa Lys
            20                  25                  30

Lys Lys Lys Lys Xaa Lys Lys Lys Lys Xaa Lys Lys Lys Lys
            35                  40                  45

Xaa Lys Lys Lys Lys Xaa Lys Lys Lys Lys Xaa Lys Lys Lys
    50                  55                  60

Lys Lys Xaa Lys Lys Lys Lys Xaa Lys Lys Lys Lys Xaa Lys
65                  70                  75                  80

Lys Lys Lys Lys Xaa Lys Lys Lys Lys Xaa Cys
            85                  90

<210> SEQ ID NO 6
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature

```
<222> LOCATION: (2)..(6)
<223> OTHER INFORMATION: This region may encompass 0 to 5 residues
<220> FEATURE:
<221> NAME/KEY: MOD_RES
<222> LOCATION: (7)..(7)
<223> OTHER INFORMATION: Any amino acid except Arg
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: MOD_RES
<222> LOCATION: (13)..(13)
<223> OTHER INFORMATION: Any amino acid except Arg
<220> FEATURE:
<221> NAME/KEY: misc_feature
<222> LOCATION: (14)..(18)
<223> OTHER INFORMATION: This region may encompass 0 to 5 residues
<220> FEATURE:
<221> NAME/KEY: MOD_RES
<222> LOCATION: (19)..(19)
<223> OTHER INFORMATION: Any amino acid except Arg
<220> FEATURE:
<221> NAME/KEY: misc_feature
<222> LOCATION: (2)..(19)
<223> OTHER INFORMATION: This region may or may not be present in its
      entirety
<220> FEATURE:
<221> NAME/KEY: misc_feature
<222> LOCATION: (20)..(24)
<223> OTHER INFORMATION: This region may encompass 0 to 5 residues
<220> FEATURE:
<221> NAME/KEY: MOD_RES
<222> LOCATION: (25)..(25)
<223> OTHER INFORMATION: Any amino acid except Arg
<220> FEATURE:
<221> NAME/KEY: misc_feature
<222> LOCATION: (26)..(30)
<223> OTHER INFORMATION: This region may encompass 0 to 5 residues
<220> FEATURE:
<221> NAME/KEY: MOD_RES
<222> LOCATION: (31)..(31)
<223> OTHER INFORMATION: Any amino acid except Arg
<220> FEATURE:
<221> NAME/KEY: misc_feature
<222> LOCATION: (32)..(36)
<223> OTHER INFORMATION: This region may encompass 0 to 5 residues
<220> FEATURE:
<221> NAME/KEY: MOD_RES
<222> LOCATION: (37)..(37)
<223> OTHER INFORMATION: Any amino acid except Arg
<220> FEATURE:
<221> NAME/KEY: misc_feature
<222> LOCATION: (20)..(37)
<223> OTHER INFORMATION: This region may or may not be present in its
      entirety
<220> FEATURE:
<221> NAME/KEY: misc_feature
<222> LOCATION: (38)..(42)
<223> OTHER INFORMATION: This region may encompass 0 to 5 residues
<220> FEATURE:
<221> NAME/KEY: MOD_RES
<222> LOCATION: (43)..(43)
<223> OTHER INFORMATION: Any amino acid except Arg
<220> FEATURE:
<221> NAME/KEY: misc_feature
<222> LOCATION: (44)..(48)
<223> OTHER INFORMATION: This region may encompass 0 to 5 residues
<220> FEATURE:
<221> NAME/KEY: MOD_RES
<222> LOCATION: (49)..(49)
<223> OTHER INFORMATION: Any amino acid except Arg
<220> FEATURE:
<221> NAME/KEY: misc_feature
<222> LOCATION: (50)..(54)
<223> OTHER INFORMATION: This region may encompass 0 to 5 residues
<220> FEATURE:
<221> NAME/KEY: MOD_RES
<222> LOCATION: (55)..(55)
```

```
<223> OTHER INFORMATION: Any amino acid except Arg
<220> FEATURE:
<221> NAME/KEY: misc_feature
<222> LOCATION: (38)..(55)
<223> OTHER INFORMATION: This region may or may not be present in its
      entirety
<220> FEATURE:
<221> NAME/KEY: misc_feature
<222> LOCATION: (56)..(60)
<223> OTHER INFORMATION: This region may encompass 0 to 5 residues
<220> FEATURE:
<221> NAME/KEY: MOD_RES
<222> LOCATION: (61)..(61)
<223> OTHER INFORMATION: Any amino acid except Arg
<220> FEATURE:
<221> NAME/KEY: misc_feature
<222> LOCATION: (62)..(66)
<223> OTHER INFORMATION: This region may encompass 0 to 5 residues
<220> FEATURE:
<221> NAME/KEY: MOD_RES
<222> LOCATION: (67)..(67)
<223> OTHER INFORMATION: Any amino acid except Arg
<220> FEATURE:
<221> NAME/KEY: misc_feature
<222> LOCATION: (68)..(72)
<223> OTHER INFORMATION: This region may encompass 0 to 5 residues
<220> FEATURE:
<221> NAME/KEY: MOD_RES
<222> LOCATION: (73)..(73)
<223> OTHER INFORMATION: Any amino acid except Arg
<220> FEATURE:
<221> NAME/KEY: misc_feature
<222> LOCATION: (56)..(73)
<223> OTHER INFORMATION: This region may or may not be present in its
      entirety
<220> FEATURE:
<221> NAME/KEY: misc_feature
<222> LOCATION: (74)..(78)
<223> OTHER INFORMATION: This region may encompass 0 to 5 residues
<220> FEATURE:
<221> NAME/KEY: MOD_RES
<222> LOCATION: (79)..(79)
<223> OTHER INFORMATION: Any amino acid except Arg
<220> FEATURE:
<221> NAME/KEY: misc_feature
<222> LOCATION: (80)..(84)
<223> OTHER INFORMATION: This region may encompass 0 to 5 residues
<220> FEATURE:
<221> NAME/KEY: MOD_RES
<222> LOCATION: (85)..(85)
<223> OTHER INFORMATION: Any amino acid except Arg
<220> FEATURE:
<221> NAME/KEY: misc_feature
<222> LOCATION: (86)..(90)
<223> OTHER INFORMATION: This region may encompass 0 to 5 residues
<220> FEATURE:
<221> NAME/KEY: MOD_RES
<222> LOCATION: (91)..(91)
<223> OTHER INFORMATION: Any amino acid except Arg
<220> FEATURE:
<221> NAME/KEY: misc_feature
<222> LOCATION: (74)..(91)
<223> OTHER INFORMATION: This region may or may not be present in its
      entirety
<220> FEATURE:
<221> NAME/KEY: DISULFID
<222> LOCATION: (1)..(92)
<223> OTHER INFORMATION: Disulfide bond between residues
<220> FEATURE:
<223> OTHER INFORMATION: See specification as filed for detailed
      description of substitutions and preferred embodiments

<400> SEQUENCE: 6

Cys Arg Arg Arg Arg Arg Xaa Arg Arg Arg Arg Xaa Arg Arg Arg
1               5                   10                  15

Arg Arg Xaa Arg Arg Arg Arg Arg Xaa Arg Arg Arg Arg Arg Xaa Arg
            20                  25                  30
```

```
Arg Arg Arg Arg Xaa Arg Arg Arg Xaa Arg Arg Arg Arg
        35                  40              45

Xaa Arg Arg Arg Arg Xaa Arg Arg Arg Arg Xaa Arg Arg Arg
    50                  55                  60

Arg Arg Xaa Arg Arg Arg Xaa Arg Arg Arg Arg Xaa Arg
65              70                  75              80

Arg Arg Arg Arg Xaa Arg Arg Arg Arg Xaa Cys
                85                  90

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(13)
<223> OTHER INFORMATION: Disulfide bond between residues

<400> SEQUENCE: 7

Cys Gly Arg Arg Arg Arg Arg Arg Arg Arg Arg Ser Cys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(13)
<223> OTHER INFORMATION: Disulfide bond between residues

<400> SEQUENCE: 8

Cys Gly Arg His Arg His Arg His Arg His Arg Ser Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(13)
<223> OTHER INFORMATION: Disulfide bond between residues

<400> SEQUENCE: 9

Cys Gly Arg His Asp Arg His Asp Arg His Asp Ser Cys
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(16)
<223> OTHER INFORMATION: Disulfide bond between residues
```

```
<400> SEQUENCE: 10

Cys Gly Arg Lys Lys Arg Arg Gln Arg Arg Pro Pro Gln Ser Cys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(16)
<223> OTHER INFORMATION: Disulfide bond between residues

<400> SEQUENCE: 11

Cys Gly Arg His Lys His Arg Gln Arg His Arg Pro Pro Gln Ser Cys
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 12

Cys Lys Gly Arg Arg Arg Arg Arg Arg Arg Arg Arg Ser Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 13

Cys Gly Lys Arg Arg Arg Arg Arg Arg Arg Arg Ser Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 14

Cys Gly Arg Lys Arg Arg Arg Arg Arg Arg Arg Ser Cys
1               5                   10
```

```
<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 15

Cys Gly Arg Arg Lys Arg Arg Arg Arg Arg Arg Arg Ser Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 16

Cys Gly Arg Arg Arg Lys Arg Arg Arg Arg Arg Arg Ser Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 17

Cys Gly Arg Arg Arg Arg Lys Arg Arg Arg Arg Arg Ser Cys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 18

Cys Gly Arg Arg Arg Arg Arg Lys Arg Arg Arg Arg Ser Cys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: DISULFID
<222> LOCATION: (1)..(14)
<223> OTHER INFORMATION: Disulfide bond between residues

<400> SEQUENCE: 19

Cys Gly Arg Arg Arg Arg Arg Lys Arg Arg Arg Arg Ser Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 20

Cys Gly Arg Arg Arg Arg Arg Arg Lys Arg Arg Arg Ser Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 21

Cys Gly Arg Arg Arg Arg Arg Arg Arg Lys Arg Ser Cys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 22

Cys Gly Arg Arg Arg Arg Arg Arg Arg Arg Arg Lys Ser Cys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 23
```

```
Cys Gly Arg Arg Arg Arg Arg Arg Arg Arg Ser Lys Cys
1               5                   10
```

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 24

```
Cys Lys Gly Arg His Arg His Arg His Arg His Arg Ser Cys
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 25

```
Cys Gly Lys Arg His Arg His Arg His Arg His Arg Ser Cys
1               5                   10
```

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 26

```
Cys Gly Arg Lys His Arg His Arg His Arg His Arg Ser Cys
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 27

```
Cys Gly Arg His Lys Arg His Arg His Arg His Arg Ser Cys
1               5                   10
```

<210> SEQ ID NO 28
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 28

Cys Gly Arg His Arg Lys His Arg His Arg His Arg Ser Cys
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 29

Cys Gly Arg His Arg His Lys Arg His Arg His Arg Ser Cys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 30

Cys Gly Arg His Arg His Arg Lys His Arg His Arg Ser Cys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 31

Cys Gly Arg His Arg His Arg His Lys Arg His Arg Ser Cys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
```

<223> OTHER INFORMATION: Disulfide bond between residues

<400> SEQUENCE: 32

Cys Gly Arg His Arg His Arg His Arg Lys His Arg Ser Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 33

Cys Gly Arg His Arg His Arg His Arg His Lys Arg Ser Cys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 34

Cys Gly Arg His Arg His Arg His Arg His Arg Lys Ser Cys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 35

Cys Gly Arg His Arg His Arg His Arg His Arg Ser Lys Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 36

Cys Lys Gly Arg His Asp Arg His Asp Arg His Asp Ser Cys
1               5                   10

```
<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 37

Cys Gly Lys Arg His Asp Arg His Asp Arg His Asp Ser Cys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 38

Cys Gly Arg Lys His Asp Arg His Asp Arg His Asp Ser Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 39

Cys Gly Arg His Lys Asp Arg His Asp Arg His Asp Ser Cys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 40

Cys Gly Arg His Asp Lys Arg His Asp Arg His Asp Ser Cys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: DISULFID
<222> LOCATION: (1)..(14)
<223> OTHER INFORMATION: Disulfide bond between residues

<400> SEQUENCE: 41

Cys Gly Arg His Asp Arg Lys His Asp Arg His Asp Ser Cys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 42

Cys Gly Arg His Asp Arg His Lys Asp Arg His Asp Ser Cys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 43

Cys Gly Arg His Asp Arg His Asp Lys Arg His Asp Ser Cys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 44

Cys Gly Arg His Asp Arg His Asp Arg Lys His Asp Ser Cys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 45
```

Cys Gly Arg His Asp Arg His Asp Arg His Lys Asp Ser Cys
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 46

Cys Gly Arg His Asp Arg His Asp Arg His Asp Lys Ser Cys
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(14)
<223> OTHER INFORMATION: Disulfide bond between residues

<400> SEQUENCE: 47

Cys Gly Arg His Asp Arg His Asp Arg His Asp Ser Lys Cys
1               5                   10

<210> SEQ ID NO 48
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(6)
<223> OTHER INFORMATION: This region may encompass 0 to 5 residues
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: misc_feature
<222> LOCATION: (2)..(12)
<223> OTHER INFORMATION: This region may or may not be present in its
      entirety
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: misc_feature
<222> LOCATION: (19)..(23)
<223> OTHER INFORMATION: This region may encompass 0 to 5 residues
<220> FEATURE:
<221> NAME/KEY: misc_feature
<222> LOCATION: (13)..(23)
<223> OTHER INFORMATION: This region may or may not be present in its
      entirety
<220> FEATURE:
<221> NAME/KEY: misc_feature
<222> LOCATION: (24)..(28)
<223> OTHER INFORMATION: This region may encompass 0 to 5 residues
<220> FEATURE:

```
<221> NAME/KEY: misc_feature
<222> LOCATION: (30)..(34)
<223> OTHER INFORMATION: This region may encompass 0 to 5 residues
<220> FEATURE:
<221> NAME/KEY: misc_feature
<222> LOCATION: (24)..(34)
<223> OTHER INFORMATION: This region may or may not be present in its
      entirety
<220> FEATURE:
<221> NAME/KEY: misc_feature
<222> LOCATION: (35)..(39)
<223> OTHER INFORMATION: This region may encompass 0 to 5 residues
<220> FEATURE:
<221> NAME/KEY: misc_feature
<222> LOCATION: (41)..(45)
<223> OTHER INFORMATION: This region may encompass 0 to 5 residues
<220> FEATURE:
<221> NAME/KEY: misc_feature
<222> LOCATION: (35)..(45)
<223> OTHER INFORMATION: This region may or may not be present in its
      entirety
<220> FEATURE:
<221> NAME/KEY: misc_feature
<222> LOCATION: (46)..(50)
<223> OTHER INFORMATION: This region may encompass 0 to 5 residues
<220> FEATURE:
<221> NAME/KEY: misc_feature
<222> LOCATION: (52)..(56)
<223> OTHER INFORMATION: This region may encompass 0 to 5 residues
<220> FEATURE:
<221> NAME/KEY: misc_feature
<222> LOCATION: (46)..(56)
<223> OTHER INFORMATION: This region may or may not be present in its
      entirety
<220> FEATURE:
<221> NAME/KEY: misc_feature
<222> LOCATION: (57)..(61)
<223> OTHER INFORMATION: This region may encompass 0 to 5 residues
<220> FEATURE:
<221> NAME/KEY: misc_feature
<222> LOCATION: (63)..(67)
<223> OTHER INFORMATION: This region may encompass 0 to 5 residues
<220> FEATURE:
<221> NAME/KEY: misc_feature
<222> LOCATION: (1)..(67)
<223> OTHER INFORMATION: Cyclic peptide
<220> FEATURE:
<223> OTHER INFORMATION: See specification as filed for detailed
      description of substitutions and preferred embodiments

<400> SEQUENCE: 48

Lys Lys Lys Lys Lys Lys His Lys Lys Lys Lys Lys Lys Lys Lys Lys
1               5                   10                  15

Lys His Lys Lys Lys Lys Lys Lys Lys Lys Lys His Lys Lys Lys
            20                  25                  30

Lys Lys Lys Lys Lys Lys His Lys Lys Lys Lys Lys Lys Lys Lys
        35                  40                  45

Lys Lys His Lys Lys Lys Lys Lys Lys Lys Lys Lys His Lys Lys
    50                  55                  60

Lys Lys Lys
65

<210> SEQ ID NO 49
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(6)
<223> OTHER INFORMATION: This region may encompass 0 to 5 residues
```

```
<220> FEATURE:
<221> NAME/KEY: misc_feature
<222> LOCATION: (8)..(12)
<223> OTHER INFORMATION: This region may encompass 0 to 5 residues
<220> FEATURE:
<221> NAME/KEY: misc_feature
<222> LOCATION: (2)..(12)
<223> OTHER INFORMATION: This region may or may not be present in its
      entirety
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: misc_feature
<222> LOCATION: (19)..(23)
<223> OTHER INFORMATION: This region may encompass 0 to 5 residues
<220> FEATURE:
<221> NAME/KEY: misc_feature
<222> LOCATION: (13)..(23)
<223> OTHER INFORMATION: This region may or may not be present in its
      entirety
<220> FEATURE:
<221> NAME/KEY: misc_feature
<222> LOCATION: (24)..(28)
<223> OTHER INFORMATION: This region may encompass 0 to 5 residues
<220> FEATURE:
<221> NAME/KEY: misc_feature
<222> LOCATION: (30)..(34)
<223> OTHER INFORMATION: This region may encompass 0 to 5 residues
<220> FEATURE:
<221> NAME/KEY: misc_feature
<222> LOCATION: (24)..(34)
<223> OTHER INFORMATION: This region may or may not be present in its
      entirety
<220> FEATURE:
<221> NAME/KEY: misc_feature
<222> LOCATION: (35)..(39)
<223> OTHER INFORMATION: This region may encompass 0 to 5 residues
<220> FEATURE:
<221> NAME/KEY: misc_feature
<222> LOCATION: (41)..(45)
<223> OTHER INFORMATION: This region may encompass 0 to 5 residues
<220> FEATURE:
<221> NAME/KEY: misc_feature
<222> LOCATION: (35)..(45)
<223> OTHER INFORMATION: This region may or may not be present in its
      entirety
<220> FEATURE:
<221> NAME/KEY: misc_feature
<222> LOCATION: (46)..(50)
<223> OTHER INFORMATION: This region may encompass 0 to 5 residues
<220> FEATURE:
<221> NAME/KEY: misc_feature
<222> LOCATION: (52)..(56)
<223> OTHER INFORMATION: This region may encompass 0 to 5 residues
<220> FEATURE:
<221> NAME/KEY: misc_feature
<222> LOCATION: (46)..(56)
<223> OTHER INFORMATION: This region may or may not be present in its
      entirety
<220> FEATURE:
<221> NAME/KEY: misc_feature
<222> LOCATION: (57)..(61)
<223> OTHER INFORMATION: This region may encompass 0 to 5 residues
<220> FEATURE:
<221> NAME/KEY: misc_feature
<222> LOCATION: (63)..(67)
<223> OTHER INFORMATION: This region may encompass 0 to 5 residues
<220> FEATURE:
<221> NAME/KEY: misc_feature
<222> LOCATION: (1)..(67)
<223> OTHER INFORMATION: Cyclic peptide
<220> FEATURE:
<223> OTHER INFORMATION: See specification as filed for detailed
      description of substitutions and preferred embodiments

<400> SEQUENCE: 49
```

```
Arg Arg Arg Arg Arg His Arg Arg Arg Arg Arg Arg Arg Arg Arg
1               5                   10                  15

Arg His Arg Arg Arg Arg Arg Arg Arg Arg Arg His Arg Arg Arg
            20                  25                  30

Arg Arg Arg Arg Arg Arg His Arg Arg Arg Arg Arg Arg Arg Arg
        35                  40                  45

Arg Arg His Arg Arg Arg Arg Arg Arg Arg Arg Arg His Arg Arg
    50                  55                  60

Arg Arg Arg
65

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(5)
<223> OTHER INFORMATION: This region may encompass 0 to 5 residues
<220> FEATURE:
<221> NAME/KEY: misc_feature
<222> LOCATION: (7)..(11)
<223> OTHER INFORMATION: This region may encompass 0 to 5 residues
<220> FEATURE:
<221> NAME/KEY: misc_feature
<222> LOCATION: (1)..(11)
<223> OTHER INFORMATION: This region may or may not be present in its
      entirety
<220> FEATURE:
<221> NAME/KEY: misc_feature
<222> LOCATION: (12)..(16)
<223> OTHER INFORMATION: This region may encompass 0 to 5 residues
<220> FEATURE:
<221> NAME/KEY: misc_feature
<222> LOCATION: (18)..(22)
<223> OTHER INFORMATION: This region may encompass 0 to 5 residues
<220> FEATURE:
<221> NAME/KEY: misc_feature
<222> LOCATION: (12)..(22)
<223> OTHER INFORMATION: This region may or may not be present in its
      entirety
<220> FEATURE:
<221> NAME/KEY: misc_feature
<222> LOCATION: (23)..(27)
<223> OTHER INFORMATION: This region may encompass 0 to 5 residues
<220> FEATURE:
<221> NAME/KEY: misc_feature
<222> LOCATION: (29)..(33)
<223> OTHER INFORMATION: This region may encompass 0 to 5 residues
<220> FEATURE:
<221> NAME/KEY: misc_feature
<222> LOCATION: (23)..(33)
<223> OTHER INFORMATION: This region may or may not be present in its
      entirety
<220> FEATURE:
<221> NAME/KEY: misc_feature
<222> LOCATION: (34)..(38)
<223> OTHER INFORMATION: This region may encompass 0 to 5 residues
<220> FEATURE:
<221> NAME/KEY: misc_feature
<222> LOCATION: (40)..(44)
<223> OTHER INFORMATION: This region may encompass 0 to 5 residues
<220> FEATURE:
<221> NAME/KEY: misc_feature
<222> LOCATION: (34)..(44)
<223> OTHER INFORMATION: This region may or may not be present in its
      entirety
<220> FEATURE:
<221> NAME/KEY: misc_feature
<222> LOCATION: (45)..(49)
<223> OTHER INFORMATION: This region may encompass 0 to 5 residues
```

```
<220> FEATURE:
<221> NAME/KEY: misc_feature
<222> LOCATION: (51)..(55)
<223> OTHER INFORMATION: This region may encompass 0 to 5 residues
<220> FEATURE:
<221> NAME/KEY: misc_feature
<222> LOCATION: (45)..(55)
<223> OTHER INFORMATION: This region may or may not be present in its
      entirety
<220> FEATURE:
<221> NAME/KEY: misc_feature
<222> LOCATION: (56)..(60)
<223> OTHER INFORMATION: This region may encompass 0 to 5 residues
<220> FEATURE:
<221> NAME/KEY: misc_feature
<222> LOCATION: (62)..(66)
<223> OTHER INFORMATION: This region may encompass 0 to 5 residues
<220> FEATURE:
<221> NAME/KEY: misc_feature
<222> LOCATION: (56)..(66)
<223> OTHER INFORMATION: This region may or may not be present in its
      entirety
<220> FEATURE:
<221> NAME/KEY: misc_feature
<222> LOCATION: (67)..(71)
<223> OTHER INFORMATION: This region may encompass 0 to 5 residues
<220> FEATURE:
<221> NAME/KEY: misc_feature
<222> LOCATION: (73)..(77)
<223> OTHER INFORMATION: This region may encompass 0 to 5 residues
<220> FEATURE:
<221> NAME/KEY: misc_feature
<222> LOCATION: (67)..(77)
<223> OTHER INFORMATION: This region may or may not be present in its
      entirety
<220> FEATURE:
<221> NAME/KEY: misc_feature
<222> LOCATION: (78)..(82)
<223> OTHER INFORMATION: This region may encompass 0 to 5 residues
<220> FEATURE:
<221> NAME/KEY: misc_feature
<222> LOCATION: (84)..(88)
<223> OTHER INFORMATION: This region may encompass 0 to 5 residues
<220> FEATURE:
<221> NAME/KEY: misc_feature
<222> LOCATION: (78)..(88)
<223> OTHER INFORMATION: This region may or may not be present in its
      entirety
<220> FEATURE:
<221> NAME/KEY: misc_feature
<222> LOCATION: (89)..(93)
<223> OTHER INFORMATION: This region may encompass 0 to 5 residues
<220> FEATURE:
<221> NAME/KEY: misc_feature
<222> LOCATION: (95)..(99)
<223> OTHER INFORMATION: This region may encompass 0 to 5 residues
<220> FEATURE:
<221> NAME/KEY: misc_feature
<222> LOCATION: (89)..(99)
<223> OTHER INFORMATION: This region may or may not be present in its
       entirety
<220> FEATURE:
<221> NAME/KEY: misc_feature
<222> LOCATION: (100)..(104)
<223> OTHER INFORMATION: This region may encompass 0 to 5 residues
<220> FEATURE:
<221> NAME/KEY: misc_feature
<222> LOCATION: (106)..(110)
<223> OTHER INFORMATION: This region may encompass 0 to 5 residues
<220> FEATURE:
<221> NAME/KEY: misc_feature
<222> LOCATION: (100)..(110)
<223> OTHER INFORMATION: This region may or may not be present in its
      entirety
<220> FEATURE:
<221> NAME/KEY: misc_feature
<222> LOCATION: (1)..(110)
<223> OTHER INFORMATION: Cyclic peptide
<220> FEATURE:
```

<223> OTHER INFORMATION: See specification as filed for detailed
      description of substitutions and preferred embodiments

<400> SEQUENCE: 50

```
Lys Lys Lys Lys Lys His Lys Lys Lys Lys Lys Lys Lys Lys Lys
1               5                   10                  15

His Lys Lys Lys Lys Lys Lys Lys Lys Lys His Lys Lys Lys Lys
            20                  25                  30

Lys Lys Lys Lys Lys His Lys Lys Lys Lys Lys Lys Lys Lys Lys
        35                  40                  45

Lys His Lys Lys Lys Lys Lys Lys Lys Lys His Lys Lys Lys Lys
    50                  55                  60

Lys Lys Lys Lys Lys Lys His Lys Lys Lys Lys Lys Lys Lys Lys
65                  70                  75                  80

Lys Lys His Lys Lys Lys Lys Lys Lys Lys Lys His Lys Lys Lys
            85                  90                  95

Lys Lys Lys Lys Lys Lys Lys His Lys Lys Lys Lys
                100                 105             110
```

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(5)
<223> OTHER INFORMATION: This region may encompass 0 to 5 residues
<220> FEATURE:
<221> NAME/KEY: misc_feature
<222> LOCATION: (7)..(11)
<223> OTHER INFORMATION: This region may encompass 0 to 5 residues
<220> FEATURE:
<221> NAME/KEY: misc_feature
<222> LOCATION: (1)..(11)
<223> OTHER INFORMATION: This region may or may not be present in its
      entirety
<220> FEATURE:
<221> NAME/KEY: misc_feature
<222> LOCATION: (12)..(16)
<223> OTHER INFORMATION: This region may encompass 0 to 5 residues
<220> FEATURE:
<221> NAME/KEY: misc_feature
<222> LOCATION: (18)..(22)
<223> OTHER INFORMATION: This region may encompass 0 to 5 residues
<220> FEATURE:
<221> NAME/KEY: misc_feature
<222> LOCATION: (12)..(22)
<223> OTHER INFORMATION: This region may or may not be present in its
      entirety
<220> FEATURE:
<221> NAME/KEY: misc_feature
<222> LOCATION: (23)..(27)
<223> OTHER INFORMATION: This region may encompass 0 to 5 residues
<220> FEATURE:
<221> NAME/KEY: misc_feature
<222> LOCATION: (29)..(33)
<223> OTHER INFORMATION: This region may encompass 0 to 5 residues
<220> FEATURE:
<221> NAME/KEY: misc_feature
<222> LOCATION: (23)..(33)
<223> OTHER INFORMATION: This region may or may not be present in its
      entirety
<220> FEATURE:
<221> NAME/KEY: misc_feature
<222> LOCATION: (34)..(38)
<223> OTHER INFORMATION: This region may encompass 0 to 5 residues
<220> FEATURE:
<221> NAME/KEY: misc_feature

```
<222> LOCATION: (40)..(44)
<223> OTHER INFORMATION: This region may encompass 0 to 5 residues
<220> FEATURE:
<221> NAME/KEY: misc_feature
<222> LOCATION: (34)..(44)
<223> OTHER INFORMATION: This region may or may not be present in its
      entirety
<220> FEATURE:
<221> NAME/KEY: misc_feature
<222> LOCATION: (45)..(49)
<223> OTHER INFORMATION: This region may encompass 0 to 5 residues
<220> FEATURE:
<221> NAME/KEY: misc_feature
<222> LOCATION: (51)..(55)
<223> OTHER INFORMATION: This region may encompass 0 to 5 residues
<220> FEATURE:
<221> NAME/KEY: misc_feature
<222> LOCATION: (45)..(55)
<223> OTHER INFORMATION: This region may or may not be present in its
      entirety
<220> FEATURE:
<221> NAME/KEY: misc_feature
<222> LOCATION: (56)..(60)
<223> OTHER INFORMATION: This region may encompass 0 to 5 residues
<220> FEATURE:
<221> NAME/KEY: misc_feature
<222> LOCATION: (62)..(66)
<223> OTHER INFORMATION: This region may encompass 0 to 5 residues
<220> FEATURE:
<221> NAME/KEY: misc_feature
<222> LOCATION: (56)..(66)
<223> OTHER INFORMATION: This region may or may not be present in its
      entirety
<220> FEATURE:
<221> NAME/KEY: misc_feature
<222> LOCATION: (67)..(71)
<223> OTHER INFORMATION: This region may encompass 0 to 5 residues
<220> FEATURE:
<221> NAME/KEY: misc_feature
<222> LOCATION: (73)..(77)
<223> OTHER INFORMATION: This region may encompass 0 to 5 residues
<220> FEATURE:
<221> NAME/KEY: misc_feature
<222> LOCATION: (67)..(77)
<223> OTHER INFORMATION: This region may or may not be present in its
      entirety
<220> FEATURE:
<221> NAME/KEY: misc_feature
<222> LOCATION: (78)..(82)
<223> OTHER INFORMATION: This region may encompass 0 to 5 residues
<220> FEATURE:
<221> NAME/KEY: misc_feature
<222> LOCATION: (84)..(88)
<223> OTHER INFORMATION: This region may encompass 0 to 5 residues
<220> FEATURE:
<221> NAME/KEY: misc_feature
<222> LOCATION: (78)..(88)
<223> OTHER INFORMATION: This region may or may not be present in its
      entirety
<220> FEATURE:
<221> NAME/KEY: misc_feature
<222> LOCATION: (89)..(93)
<223> OTHER INFORMATION: This region may encompass 0 to 5 residues
<220> FEATURE:
<221> NAME/KEY: misc_feature
<222> LOCATION: (95)..(99)
<223> OTHER INFORMATION: This region may encompass 0 to 5 residues
<220> FEATURE:
<221> NAME/KEY: misc_feature
<222> LOCATION: (89)..(99)
<223> OTHER INFORMATION: This region may or may not be present in its
      entirety
<220> FEATURE:
<221> NAME/KEY: misc_feature
<222> LOCATION: (100)..(104)
<223> OTHER INFORMATION: This region may encompass 0 to 5 residues
<220> FEATURE:
<221> NAME/KEY: misc_feature
<222> LOCATION: (106)..(110)
```

```
<223> OTHER INFORMATION: This region may encompass 0 to 5 residues
<220> FEATURE:
<221> NAME/KEY: misc_feature
<222> LOCATION: (100)..(110)
<223> OTHER INFORMATION: This region may or may not be present in its
      entirety
<220> FEATURE:
<221> NAME/KEY: misc_feature
<222> LOCATION: (1)..(110)
<223> OTHER INFORMATION: Cyclic peptide
<220> FEATURE:
<223> OTHER INFORMATION: See specification as filed for detailed
      description of substitutions and preferred embodiments

<400> SEQUENCE: 51

Arg Arg Arg Arg Arg His Arg Arg Arg Arg Arg Arg Arg Arg Arg
1               5                   10                  15

His Arg Arg Arg Arg Arg Arg Arg Arg Arg His Arg Arg Arg Arg
            20                  25                  30

Arg Arg Arg Arg Arg His Arg Arg Arg Arg Arg Arg Arg Arg Arg
        35                  40                  45

Arg His Arg Arg Arg Arg Arg Arg Arg Arg Arg His Arg Arg Arg
    50                  55                  60

Arg Arg Arg Arg Arg Arg Arg His Arg Arg Arg Arg Arg Arg Arg
65                  70                  75                  80

Arg Arg His Arg Arg Arg Arg Arg Arg Arg Arg His Arg Arg
            85                  90                  95

Arg Arg Arg Arg Arg Arg Arg Arg His Arg Arg Arg Arg
            100                 105                 110

<210> SEQ ID NO 52
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(5)
<223> OTHER INFORMATION: This region may encompass 0 to 5 residues
<220> FEATURE:
<221> NAME/KEY: MOD_RES
<222> LOCATION: (6)..(6)
<223> OTHER INFORMATION: Any amino acid except Lys
<220> FEATURE:
<221> NAME/KEY: misc_feature
<222> LOCATION: (7)..(11)
<223> OTHER INFORMATION: This region may encompass 0 to 5 residues
<220> FEATURE:
<221> NAME/KEY: MOD_RES
<222> LOCATION: (12)..(12)
<223> OTHER INFORMATION: Any amino acid except Lys
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: MOD_RES
<222> LOCATION: (18)..(18)
<223> OTHER INFORMATION: Any amino acid except Lys
<220> FEATURE:
<221> NAME/KEY: misc_feature
<222> LOCATION: (1)..(18)
<223> OTHER INFORMATION: This region may or may not be present in its
      entirety
<220> FEATURE:
<221> NAME/KEY: misc_feature
<222> LOCATION: (19)..(23)
<223> OTHER INFORMATION: This region may encompass 0 to 5 residues
<220> FEATURE:
```

```
<221> NAME/KEY: MOD_RES
<222> LOCATION: (24)..(24)
<223> OTHER INFORMATION: Any amino acid except Lys
<220> FEATURE:
<221> NAME/KEY: misc_feature
<222> LOCATION: (25)..(29)
<223> OTHER INFORMATION: This region may encompass 0 to 5 residues
<220> FEATURE:
<221> NAME/KEY: MOD_RES
<222> LOCATION: (30)..(30)
<223> OTHER INFORMATION: Any amino acid except Lys
<220> FEATURE:
<221> NAME/KEY: misc_feature
<222> LOCATION: (31)..(35)
<223> OTHER INFORMATION: This region may encompass 0 to 5 residues
<220> FEATURE:
<221> NAME/KEY: MOD_RES
<222> LOCATION: (36)..(36)
<223> OTHER INFORMATION: Any amino acid except Lys
<220> FEATURE:
<221> NAME/KEY: misc_feature
<222> LOCATION: (19)..(36)
<223> OTHER INFORMATION: This region may or may not be present in its
      entirety
<220> FEATURE:
<221> NAME/KEY: misc_feature
<222> LOCATION: (37)..(41)
<223> OTHER INFORMATION: This region may encompass 0 to 5 residues
<220> FEATURE:
<221> NAME/KEY: MOD_RES
<222> LOCATION: (42)..(42)
<223> OTHER INFORMATION: Any amino acid except Lys
<220> FEATURE:
<221> NAME/KEY: misc_feature
<222> LOCATION: (43)..(47)
<223> OTHER INFORMATION: This region may encompass 0 to 5 residues
<220> FEATURE:
<221> NAME/KEY: MOD_RES
<222> LOCATION: (48)..(48)
<223> OTHER INFORMATION: Any amino acid except Lys
<220> FEATURE:
<221> NAME/KEY: misc_feature
<222> LOCATION: (49)..(53)
<223> OTHER INFORMATION: This region may encompass 0 to 5 residues
<220> FEATURE:
<221> NAME/KEY: MOD_RES
<222> LOCATION: (54)..(54)
<223> OTHER INFORMATION: Any amino acid except Lys
<220> FEATURE:
<221> NAME/KEY: misc_feature
<222> LOCATION: (37)..(54)
<223> OTHER INFORMATION: This region may or may not be present in its
      entirety
<220> FEATURE:
<221> NAME/KEY: misc_feature
<222> LOCATION: (55)..(59)
<223> OTHER INFORMATION: This region may encompass 0 to 5 residues
<220> FEATURE:
<221> NAME/KEY: MOD_RES
<222> LOCATION: (60)..(60)
<223> OTHER INFORMATION: Any amino acid except Lys
<220> FEATURE:
<221> NAME/KEY: misc_feature
<222> LOCATION: (61)..(65)
<223> OTHER INFORMATION: This region may encompass 0 to 5 residues
<220> FEATURE:
<221> NAME/KEY: MOD_RES
<222> LOCATION: (66)..(66)
<223> OTHER INFORMATION: Any amino acid except Lys
<220> FEATURE:
<221> NAME/KEY: misc_feature
<222> LOCATION: (67)..(71)
<223> OTHER INFORMATION: This region may encompass 0 to 5 residues
<220> FEATURE:
<221> NAME/KEY: MOD_RES
<222> LOCATION: (72)..(72)
<223> OTHER INFORMATION: Any amino acid except Lys
<220> FEATURE:
<221> NAME/KEY: misc_feature
```

```
<222> LOCATION: (55)..(72)
<223> OTHER INFORMATION: This region may or may not be present in its
      entirety
<220> FEATURE:
<221> NAME/KEY: misc_feature
<222> LOCATION: (73)..(77)
<223> OTHER INFORMATION: This region may encompass 0 to 5 residues
<220> FEATURE:
<221> NAME/KEY: MOD_RES
<222> LOCATION: (78)..(78)
<223> OTHER INFORMATION: Any amino acid except Lys
<220> FEATURE:
<221> NAME/KEY: misc_feature
<222> LOCATION: (79)..(83)
<223> OTHER INFORMATION: This region may encompass 0 to 5 residues
<220> FEATURE:
<221> NAME/KEY: MOD_RES
<222> LOCATION: (84)..(84)
<223> OTHER INFORMATION: Any amino acid except Lys
<220> FEATURE:
<221> NAME/KEY: misc_feature
<222> LOCATION: (85)..(89)
<223> OTHER INFORMATION: This region may encompass 0 to 5 residues
<220> FEATURE:
<221> NAME/KEY: MOD_RES
<222> LOCATION: (90)..(90)
<223> OTHER INFORMATION: Any amino acid except Lys
<220> FEATURE:
<221> NAME/KEY: misc_feature
<222> LOCATION: (73)..(90)
<223> OTHER INFORMATION: This region may or may not be present in its
      entirety
<220> FEATURE:
<221> NAME/KEY: misc_feature
<222> LOCATION: (1)..(90)
<223> OTHER INFORMATION: Cyclic peptide
<220> FEATURE:
<223> OTHER INFORMATION: See specification as filed for detailed
      description of substitutions and preferred embodiments

<400> SEQUENCE: 52

Lys Lys Lys Lys Lys Xaa Lys Lys Lys Lys Xaa Lys Lys Lys Lys
1               5                   10                  15

Lys Xaa Lys Lys Lys Lys Lys Xaa Lys Lys Lys Lys Lys Xaa Lys Lys
            20                  25                  30

Lys Lys Lys Xaa Lys Lys Lys Lys Lys Xaa Lys Lys Lys Lys Lys Xaa
        35                  40                  45

Lys Lys Lys Lys Lys Xaa Lys Lys Lys Lys Lys Xaa Lys Lys Lys Lys
    50                  55                  60

Lys Xaa Lys Lys Lys Lys Lys Xaa Lys Lys Lys Lys Lys Xaa Lys Lys
65                  70                  75                  80

Lys Lys Lys Xaa Lys Lys Lys Lys Lys Xaa
        85                  90

<210> SEQ ID NO 53
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(5)
<223> OTHER INFORMATION: This region may encompass 0 to 5 residues
<220> FEATURE:
<221> NAME/KEY: MOD_RES
<222> LOCATION: (6)..(6)
<223> OTHER INFORMATION: Any amino acid except Arg
<220> FEATURE:
<221> NAME/KEY: misc_feature
<222> LOCATION: (7)..(11)
```

```
<223> OTHER INFORMATION: This region may encompass 0 to 5 residues
<220> FEATURE:
<221> NAME/KEY: MOD_RES
<222> LOCATION: (12)..(12)
<223> OTHER INFORMATION: Any amino acid except Arg
<220> FEATURE:
<221> NAME/KEY: misc_feature
<222> LOCATION: (13)..(17)
<223> OTHER INFORMATION: This region may encompass 0 to 5 residues
<220> FEATURE:
<221> NAME/KEY: MOD_RES
<222> LOCATION: (18)..(18)
<223> OTHER INFORMATION: Any amino acid except Arg
<220> FEATURE:
<221> NAME/KEY: misc_feature
<222> LOCATION: (1)..(18)
<223> OTHER INFORMATION: This region may or may not be present in its
      entirety
<220> FEATURE:
<221> NAME/KEY: misc_feature
<222> LOCATION: (19)..(23)
<223> OTHER INFORMATION: This region may encompass 0 to 5 residues
<220> FEATURE:
<221> NAME/KEY: MOD_RES
<222> LOCATION: (24)..(24)
<223> OTHER INFORMATION: Any amino acid except Arg
<220> FEATURE:
<221> NAME/KEY: misc_feature
<222> LOCATION: (25)..(29)
<223> OTHER INFORMATION: This region may encompass 0 to 5 residues
<220> FEATURE:
<221> NAME/KEY: MOD_RES
<222> LOCATION: (30)..(30)
<223> OTHER INFORMATION: Any amino acid except Arg
<220> FEATURE:
<221> NAME/KEY: misc_feature
<222> LOCATION: (31)..(35)
<223> OTHER INFORMATION: This region may encompass 0 to 5 residues
<220> FEATURE:
<221> NAME/KEY: MOD_RES
<222> LOCATION: (36)..(36)
<223> OTHER INFORMATION: Any amino acid except Arg
<220> FEATURE:
<221> NAME/KEY: misc_feature
<222> LOCATION: (19)..(36)
<223> OTHER INFORMATION: This region may or may not be present in its
      entirety
<220> FEATURE:
<221> NAME/KEY: misc_feature
<222> LOCATION: (37)..(41)
<223> OTHER INFORMATION: This region may encompass 0 to 5 residues
<220> FEATURE:
<221> NAME/KEY: MOD_RES
<222> LOCATION: (42)..(42)
<223> OTHER INFORMATION: Any amino acid except Arg
<220> FEATURE:
<221> NAME/KEY: misc_feature
<222> LOCATION: (43)..(47)
<223> OTHER INFORMATION: This region may encompass 0 to 5 residues
<220> FEATURE:
<221> NAME/KEY: MOD_RES
<222> LOCATION: (48)..(48)
<223> OTHER INFORMATION: Any amino acid except Arg
<220> FEATURE:
<221> NAME/KEY: misc_feature
<222> LOCATION: (49)..(53)
<223> OTHER INFORMATION: This region may encompass 0 to 5 residues
<220> FEATURE:
<221> NAME/KEY: MOD_RES
<222> LOCATION: (54)..(54)
<223> OTHER INFORMATION: Any amino acid except Arg
<220> FEATURE:
<221> NAME/KEY: misc_feature
<222> LOCATION: (37)..(54)
<223> OTHER INFORMATION: This region may or may not be present in its
      entirety
<220> FEATURE:
<221> NAME/KEY: misc_feature
<222> LOCATION: (55)..(59)
```

```
<223> OTHER INFORMATION: This region may encompass 0 to 5 residues
<220> FEATURE:
<221> NAME/KEY: MOD_RES
<222> LOCATION: (60)..(60)
<223> OTHER INFORMATION: Any amino acid except Arg
<220> FEATURE:
<221> NAME/KEY: misc_feature
<222> LOCATION: (61)..(65)
<223> OTHER INFORMATION: This region may encompass 0 to 5 residues
<220> FEATURE:
<221> NAME/KEY: MOD_RES
<222> LOCATION: (66)..(66)
<223> OTHER INFORMATION: Any amino acid except Arg
<220> FEATURE:
<221> NAME/KEY: misc_feature
<222> LOCATION: (67)..(71)
<223> OTHER INFORMATION: This region may encompass 0 to 5 residues
<220> FEATURE:
<221> NAME/KEY: MOD_RES
<222> LOCATION: (72)..(72)
<223> OTHER INFORMATION: Any amino acid except Arg
<220> FEATURE:
<221> NAME/KEY: misc_feature
<222> LOCATION: (55)..(72)
<223> OTHER INFORMATION: This region may or may not be present in its
      entirety
<220> FEATURE:
<221> NAME/KEY: misc_feature
<222> LOCATION: (73)..(77)
<223> OTHER INFORMATION: This region may encompass 0 to 5 residues
<220> FEATURE:
<221> NAME/KEY: MOD_RES
<222> LOCATION: (78)..(78)
<223> OTHER INFORMATION: Any amino acid except Arg
<220> FEATURE:
<221> NAME/KEY: misc_feature
<222> LOCATION: (79)..(83)
<223> OTHER INFORMATION: This region may encompass 0 to 5 residues
<220> FEATURE:
<221> NAME/KEY: MOD_RES
<222> LOCATION: (84)..(84)
<223> OTHER INFORMATION: Any amino acid except Arg
<220> FEATURE:
<221> NAME/KEY: misc_feature
<222> LOCATION: (85)..(89)
<223> OTHER INFORMATION: This region may encompass 0 to 5 residues
<220> FEATURE:
<221> NAME/KEY: MOD_RES
<222> LOCATION: (90)..(90)
<223> OTHER INFORMATION: Any amino acid except Arg
<220> FEATURE:
<221> NAME/KEY: misc_feature
<222> LOCATION: (73)..(90)
<223> OTHER INFORMATION: This region may or may not be present in its
      entirety
<220> FEATURE:
<221> NAME/KEY: misc_feature
<222> LOCATION: (1)..(90)
<223> OTHER INFORMATION: Cyclic peptide
<220> FEATURE:
<223> OTHER INFORMATION: See specification as filed for detailed
      description of substitutions and preferred embodiments

<400> SEQUENCE: 53

Arg Arg Arg Arg Arg Xaa Arg Arg Arg Arg Xaa Arg Arg Arg Arg
1               5                   10                  15

Arg Xaa Arg Arg Arg Arg Arg Xaa Arg Arg Arg Arg Xaa Arg Arg
                20                  25                  30

Arg Arg Arg Xaa Arg Arg Arg Arg Xaa Arg Arg Arg Arg Arg Xaa
            35                  40                  45

Arg Arg Arg Arg Arg Xaa Arg Arg Arg Arg Xaa Arg Arg Arg Arg
    50                  55                  60

Arg Xaa Arg Arg Arg Arg Arg Xaa Arg Arg Arg Arg Xaa Arg Arg
65                  70                  75                  80
```

```
Arg Arg Arg Xaa Arg Arg Arg Arg Xaa
            85                  90

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic peptide

<400> SEQUENCE: 54

Gly Arg Arg Arg Arg Arg Arg Arg Arg Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic peptide

<400> SEQUENCE: 55

Gly Arg His Arg His Arg His Arg His Arg Ser
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic peptide

<400> SEQUENCE: 56

Gly Arg His Asp Arg His Asp Arg His Asp Ser
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: Cyclic peptide

<400> SEQUENCE: 57

Gly Arg Lys Lys Arg Arg Gln Arg Arg Pro Pro Gln Ser
1               5                   10

<210> SEQ ID NO 58
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: Cyclic peptide

<400> SEQUENCE: 58

Gly Arg His Lys His Arg Gln Arg His Arg Pro Pro Gln Ser
1               5                  10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 59

Lys Gly Arg Arg Arg Arg Arg Arg Arg Arg Arg Ser
1               5                  10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 60

Gly Lys Arg Arg Arg Arg Arg Arg Arg Arg Arg Ser
1               5                  10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 61

Gly Arg Lys Arg Arg Arg Arg Arg Arg Arg Arg Ser
1               5                  10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (1)..(12)
<223> OTHER INFORMATION: Cyclic peptide

<400> SEQUENCE: 62

Gly Arg Arg Lys Arg Arg Arg Arg Arg Arg Arg Ser
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 63

Gly Arg Arg Arg Lys Arg Arg Arg Arg Arg Arg Ser
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 64

Gly Arg Arg Arg Arg Lys Arg Arg Arg Arg Arg Ser
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 65

Gly Arg Arg Arg Arg Arg Lys Arg Arg Arg Arg Ser
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 66

Gly Arg Arg Arg Arg Arg Arg Lys Arg Arg Arg Ser
1               5                   10
```

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 67

Gly Arg Arg Arg Arg Arg Arg Arg Lys Arg Arg Ser
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 68

Gly Arg Arg Arg Arg Arg Arg Arg Arg Lys Arg Ser
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 69

Gly Arg Arg Arg Arg Arg Arg Arg Arg Arg Lys Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 70

Gly Arg Arg Arg Arg Arg Arg Arg Arg Arg Ser Lys
1               5                   10

<210> SEQ ID NO 71
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 71

Lys Gly Arg His Arg His Arg His Arg His Arg Ser
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 72

Gly Lys Arg His Arg His Arg His Arg His Arg Ser
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 73

Gly Arg Lys His Arg His Arg His Arg His Arg Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 74

Gly Arg His Lys Arg His Arg His Arg His Arg Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide
```

```
<400> SEQUENCE: 75

Gly Arg His Arg Lys His Arg His Arg His Arg Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 76

Gly Arg His Arg His Lys Arg His Arg His Arg Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 77

Gly Arg His Arg His Arg Lys His Arg His Arg Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 78

Gly Arg His Arg His Arg His Lys Arg His Arg Ser
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 79

Gly Arg His Arg His Arg His Arg Lys His Arg Ser
1               5                   10

<210> SEQ ID NO 80
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 80

Gly Arg His Arg His Arg His Arg His Lys Arg Ser
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 81

Gly Arg His Arg His Arg His Arg His Arg Lys Ser
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 82

Gly Arg His Arg His Arg His Arg His Arg Ser Lys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 83

Lys Gly Arg His Asp Arg His Asp Arg His Asp Ser
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (1)..(12)
<223> OTHER INFORMATION: Cyclic peptide

<400> SEQUENCE: 84

Gly Lys Arg His Asp Arg His Asp Arg His Asp Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 85

Gly Arg Lys His Asp Arg His Asp Arg His Asp Ser
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 86

Gly Arg His Lys Asp Arg His Asp Arg His Asp Ser
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 87

Gly Arg His Asp Lys Arg His Asp Arg His Asp Ser
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 88

Gly Arg His Asp Arg Lys His Asp Arg His Asp Ser
```

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 89

Gly Arg His Asp Arg His Lys Asp Arg His Asp Ser
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 90

Gly Arg His Asp Arg His Asp Lys Arg His Asp Ser
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 91

Gly Arg His Asp Arg His Asp Arg Lys His Asp Ser
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 92

Gly Arg His Asp Arg His Asp Arg His Lys Asp Ser
1               5                   10

<210> SEQ ID NO 93
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 93

Gly Arg His Asp Arg His Asp Arg His Asp Lys Ser
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclic peptide

<400> SEQUENCE: 94

Gly Arg His Asp Arg His Asp Arg His Asp Ser Lys
1               5                   10

<210> SEQ ID NO 95
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(26)
<223> OTHER INFORMATION: Cyclic peptide

<400> SEQUENCE: 95

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 96
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: Cyclic peptide

<400> SEQUENCE: 96

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40

<210> SEQ ID NO 97
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(38)
<223> OTHER INFORMATION: Cyclic peptide

<400> SEQUENCE: 97

Gly Phe Gly Cys Pro Leu Asn Gln Gly Ala Cys His Arg His Cys Arg
1               5                   10                  15

Ser Ile Arg Arg Arg Gly Gly Tyr Cys Ala Gly Phe Phe Lys Gln Thr
            20                  25                  30

Cys Thr Cys Tyr Arg Asn
        35

<210> SEQ ID NO 98
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(56)
<223> OTHER INFORMATION: Cyclic peptide

<400> SEQUENCE: 98

Gly Leu Gly Ser Val Phe Gly Arg Leu Ala Arg Ile Leu Gly Arg Val
1               5                   10                  15

Ile Pro Lys Val Ala Lys Lys Leu Gly Pro Lys Val Ala Lys Val Leu
            20                  25                  30

Pro Lys Val Met Lys Glu Ala Ile Pro Met Ala Val Glu Met Ala Lys
        35                  40                  45

Ser Gln Glu Glu Gln Gln Pro Gln
    50                  55

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(23)
<223> OTHER INFORMATION: Cyclic peptide

<400> SEQUENCE: 99

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (1)..(27)
<223> OTHER INFORMATION: Cyclic peptide

<400> SEQUENCE: 100

Lys Ile Lys Trp Phe Lys Thr Met Lys Ser Ile Ala Lys Phe Ile Ala
1               5                   10                  15

Lys Glu Gln Met Lys Lys His Leu Gly Gly Glu
            20                  25

<210> SEQ ID NO 101
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(78)
<223> OTHER INFORMATION: Cyclic peptide

<400> SEQUENCE: 101

Gly Tyr Phe Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
            20                  25                  30

Gln Val Cys Asp Lys Leu Lys Ile Leu Arg Gly Leu Cys Lys Lys Ile
        35                  40                  45

Met Arg Ser Phe Leu Arg Arg Ile Ser Trp Asp Ile Leu Thr Gly Lys
    50                  55                  60

Lys Pro Gln Ala Ile Cys Val Asp Ile Lys Ile Cys Lys Glu
65                  70                  75

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(21)
<223> OTHER INFORMATION: Cyclic peptide

<400> SEQUENCE: 102

Lys Thr Asn Met Lys His Met Ala Gly Ala Ala Ala Ala Gly Ala Val
1               5                   10                  15

Val Gly Gly Leu Gly
            20

<210> SEQ ID NO 103
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: Cyclic peptide

<400> SEQUENCE: 103

Asp Ala Glu Phe Arg His Asp Ser Gly Tyr Glu Val His His Gln Lys
1               5                   10                  15
```

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 104
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(37)
<223> OTHER INFORMATION: Cyclic peptide

<400> SEQUENCE: 104

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(22)
<223> OTHER INFORMATION: Cyclic peptide

<400> SEQUENCE: 105

Lys Leu Leu Lys Leu Leu Leu Lys Leu Leu Lys Leu Leu Leu Lys Leu
1               5                   10                  15

Leu Leu Lys Leu Leu Lys
            20

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
gccagacuuu guuggauuug aaatt                                        25

<210> SEQ ID NO 107
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)

```
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 107
aauuucaaau ccaacaaagu cuggcuu                                          27

<210> SEQ ID NO 108
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-(CH2)6-NH2
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 108
```
aauuucaaau ccaacaaagu cuggcuu                                              27

<210> SEQ ID NO 109
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-(CH2)6-SH
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 109
aauuucaaau ccaacaaagu cuggcuu                                              27

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ggagggcuuu cuuuguguau uugcc                                                25

<210> SEQ ID NO 111
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:

```
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 111
ggcaaauaca caaagaaagc ccucccc                                            27

<210> SEQ ID NO 112
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-(CH2)6-NH2
<220> FEATURE:
<221> NAME/KEY: modified_base
<222> LOCATION: (1)..(4)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 112
ggcaaauaca caaagaaagc ccucccc                                            27

<210> SEQ ID NO 113
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
```

```
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 113
ggcaaauaca caaagaaagc ccucccc                                           27

<210> SEQ ID NO 114
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-(CH2)6-NH2
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified
<220> FEATURE:
<221> NAME/KEY: modified_base
<222> LOCATION: (23)..(23)
<223> OTHER INFORMATION: 2'-O-methyl modified
<220> FEATURE:
<221> NAME/KEY: modified_base
<222> LOCATION: (25)..(27)
<223> OTHER INFORMATION: 2'-O-methyl modified

<400> SEQUENCE: 114
ggcaaauaca caaagaaagc ccucccc                                           27
```